(12) United States Patent
Castro Pineiro et al.

(10) Patent No.: US 7,468,393 B2
(45) Date of Patent: Dec. 23, 2008

(54) DIARYLSULFONES AS 5-HT2A ANTAGONISTS

(75) Inventors: Jose Luis Castro Pineiro, Bishops Stortford (GB); Laura Catherine Cooper, Bishops Stortford (GB); Myra Gilligan, Bishops Stortford (GB); Alexander Charles Humphries, Stevenage (GB); Peter Alan Hunt, Saffron Walden (GB); Tamara Ladduwahetty, London (GB); Angus Murray MacLeod, Bishops Stortford (GB); Kevin John Merchant, Ware (GB); Monique Bodil Van Niel, Welwyn (GB); Kevin Wilson, Boston, MA (US)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 0 days.

(21) Appl. No.: 11/796,389

(22) Filed: Apr. 27, 2007

(65) Prior Publication Data
US 2007/0203205 A1 Aug. 30, 2007

Related U.S. Application Data

(62) Division of application No. 11/212,789, filed on Aug. 26, 2005, now Pat. No. 7,217,740.

(30) Foreign Application Priority Data
Aug. 27, 2004 (GB) ................................. 0419192.0

(51) Int. Cl.
*A61K 31/10* (2006.01)
*C07C 317/24* (2006.01)
*C07C 317/32* (2006.01)

(52) U.S. Cl. ............................ 514/710; 568/32; 568/34
(58) Field of Classification Search ................ 514/710; 568/32, 34
See application file for complete search history.

(56) References Cited

U.S. PATENT DOCUMENTS

| | | | |
|---|---|---|---|
| 2,784,184 | A | 3/1957 | Zweidler et al. |
| 3,256,340 | A | 6/1966 | Russell |
| 4,128,552 | A | 12/1978 | Wise et al. |
| 4,218,455 | A | 8/1980 | Wise et al. |
| 4,812,461 | A | 3/1989 | Antoku et al. |
| 4,977,165 | A | 12/1990 | Oinuma et al. |
| 6,479,479 | B2 | 11/2002 | Achard et al. |
| 6,559,166 | B1 | 5/2003 | Blurton et al. |
| 6,872,717 | B2 | 3/2005 | Achard et al. |
| 2003/0130287 | A1 | 7/2003 | Ackermann et al. |
| 2003/0181464 | A1 | 9/2003 | Burkamp et al. |

FOREIGN PATENT DOCUMENTS

| | | |
|---|---|---|
| WO | WO 96/02509 | 2/1996 |
| WO | WO 96/35666 | 11/1996 |
| WO | WO 97/21680 | 6/1997 |
| WO | WO 00/31037 | 6/2000 |
| WO | WO 01/40230 | 6/2001 |
| WO | WO 02/083645 | 10/2002 |
| WO | WO 2002/088113 | 11/2002 |
| WO | WO 02/100864 | 12/2002 |
| WO | WO 2005/016920 | 2/2005 |
| WO | WO 2005/082343 | 9/2005 |

OTHER PUBLICATIONS

Abstarct of Simalty-Siemiatycki et al., Bulletin de la Societe Chimique de France (1962), p. 125-8.*
Stephen R. Fletcher, et al: "4-(Phenylsulfonyl)piperidines: Novel, Selective, and Bioavailable 5-HT2A Receptor Antagonist". Journal of Medicinal Chemistry, 2002, vol. 45, No. 2, pp. 492-503.
Fukami, Jiichi et al: "Preparation of Hydantoin Derivatives as Cardiovascular Agents", XP002356147, Database Caplus Chemical Abstracts Service, Database accession No. 1997:189919.
Zhi Chen, et al., "Preparation of New Anti-Tubulin Ligands through a Dual-Mode, Addition-Elimination Reaction to a Bromo-Substituted alpha, beta-Unsaturated Sulfoxide", Journal of Organic Chemistry, vol. 65, No. 25, 2000, pp. 8811-8815.
Franc C. et al: "A General Synthesis of 2-Formyl-3-Arylpyrroles" Tetrahedrono Letters, pp. 4555-4558, Jun. 11, 1999.
Masquelin T. et al: "A New Approach to the Synthesis of N-Protected 2- and 5-Substitituted 3-Halopyrroles" 1995. Synthesis pp. 276-784.
Shafiee A. et al: "Syntheses of 2-(2-Arylethyl)Imidazoles" 1998, Journal of Heterocyclic Chemistry, pp. 607-610.
Garcia Ruano J. L. et al: "Synthesis of chiral ortho-(p-tolylsulfinyl) benzyl ketones", Oct. 25, 2004, Tetrahedron, pp. 10067-10075.
Alberola A. et al: "The reaction of beta-aminoenones with substituted acetonitriles. Regiospecific synthesis of 2(1H)-pyridones", 1987, Journal of Heterocyclic Chemistry, Heterocorporation. pp. 709-713.
Ayambem A. et al: "Endgroup substituent effects on the rate/extent of network formation and adhesion for phenylethynyl-terminated poly(arylene ether sulfone) oligomers", Jun. 1000, Polymer, pp. 5109-5124.
Mokhtar Hassan et al: "Synthesis of some substituted pyrazole-3-carboxylic acids with possible hypoglycemic and antimicrobial activity. Part 1" 1978, Pharmazie, pp. 649-651.

(Continued)

*Primary Examiner*—Kamal A Saeed
*Assistant Examiner*—Yong Chu
(74) *Attorney, Agent, or Firm*—J. Eric Thies; William Krovatin

(57) ABSTRACT

Compounds of formula I:

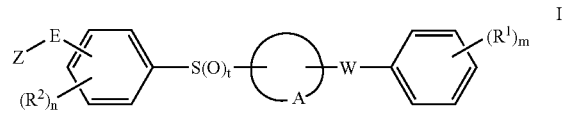

are potent and selective antagonists of the human 5-HT$_{2A}$ receptor, and hence useful in treatment of a variety of adverse conditions of the CNS.

17 Claims, No Drawings

OTHER PUBLICATIONS

Database Beilstein, Beilstein Institut zur Forderung der Chemischen Wissenschaft, Frankfurt am Main, DE: XP00235619, retrieved from XFIRE Database accession No. 3062620, 3100377, 3101626, 3099644, 3101535; J of Org Chem., vol. 33, No. 6, 1968, pp. 2228-2233.

Ghosez L. et al: "Studies of palladium-catalyzed coupling reactions for preparation of hindered 3-arylpyrroles relevant to (−)-rhazinilam and its analogues", 2001, Canadian Journal of Chemistry National Research Council. pp. 1827-1840.

Database Beilstein, Databas accession No. 2599161, 2537238, 7117539, 2541627, 2541951; Bull. Soc. Chim. Fr., 1962, pp. 129-131.

Zachary P. Demiko and K. Barry Sharpless: "A Click Chemistry Approach to Tetrazoles by Huigsen 1, 3-Dipolar Cycloaddition: Synthesis of 5-Sulfonyl Tetrazoles from Azides and Sulfonyl Cyanides" Angew. Chem. Int. Ed, vol. 41, No. 12, 2002, pp. 2110-2113.

Michael E. Wright and Edward G. Toplikar: "A preliminary study of poly(p-phenylene) based nonlinea optical materials" Macromol. Chem. Phys., vol. 196, 1995, pp. 3563-3575.

Mitsuhiro Yoshimatsu et al: "A Convenient Synthesis of Alkynlpyrazoles" J. Chem. Soc. Perkin Trans. I. 1997, pgaes. 695-700.

Matthew D. Cliff and Stephen G. Pyne: "Palladium Catalysed Coupling of Imidazoles to Alkynyl and Vinyl Sustrates" Tetrahedron, vol. 52, No. 43, 1996, pp. 13703-13712.

Werner Hinz et al: "Pyrrole Studies 34, Synthesis of 1,2-Di(2-pyroolyl)ethenes and Related Compounds" Synthesis, 1986, pp. 620-623.

Matthew S. Addie and Richard J. K. Taylor: "New routes to 5-substituted oxazoles", J. Chem. Soc. Perkin I, 2000, pp. 527-531.

Jose L. Garcia Ruano et al: "Remote Sterocontrol by Sulfinyl Groups: Reduction of delta-Ketosulfoxides", J. Org. Chem., vol. 70, May 2, 2005, pp. 1796-1801, XP002356128.

Jose L. Garcia Ruano et : "Highly Stereoselective vinylogous Pummerer Reaction Mediated by ME3SIX", Org. Lett., vol. 7, No. 1, Dec. 14, 2004, pp. 19-22.

S. Wakabayashi et al: Ligand coupling of 2-Pyridyl Sulfoxides Having an sp2 Stereocenter at the alpha-Position: A novel Preparation of alpha-stilbazoles, Heteroatom Chemistry, vol. 1, No. 3, 1990, pp. 225-232.

Shafiee, A. et al: "Synthesis of substituted, 1, 2, 4-triazoles", XP002356151, Database Caplus Database accession No. 1993-191644: Journal of Heterocyclic Chemistry, 29(7), 1863-5, 1992.

Murata, Yasue et al: "Syntheses of 3, 4-disubstituted 2-tosylpyrroles and 5-tosyl-1, 5-dihydro-2H-pyrrol-2-ones starting from ethyl, 3, 4-disbustituted 2-pyrrolecarboxylates" XP002356152, Database Caplus, Database accession No. 1996: 717134; Bulletin of The Chemical Society of Japan, 69(11), 3339-3344, 1996.

Najera, Carmen et al: "Dilithiated (E)-N-isoprypyl-3-tosylacrylamide: a new beta-acylvinyl anion equivalent in organic synthesis", XP002356153, Database Caplus, Database accession No. 1990:118553; Journal of The Chemical Society, Perkin Transactions 1: Organic and Bio-Organic Chemistry, (8) 1387-91, 1989.

Van Nispen, Simon P. J. M. et al: "Chemistry of sulfonylmethyl isocyanides. 21. Use of dilithio(tolysulfonyl)methy isocyanide in the synthesis of oxazoles and imidazoles", XP002356154. Datbase Caplus, Database accession No. 1981:103454; Tetrahedron Letters, 21(38), 3723-6, 1980.

Settambolo, Roberta et al: "Synthesis of 3-vinylpyrrole", XP002356155, Database Caplus, Database accession No. 1994:77125; Journal of Organic Chemistry, 58(27), 7899-902, 1993.

Kinoshita, Hideki et al: "A new and effective aminomethylation of the use of N-(p-toluenesulfonylmethyl)-p-toluenesulfonamide as an equievalent of methanimine. A convenient perparatio of pyrrole compounds", XP002356156. Database Caplus,Database accession No. 1987:84319; Chemistry Letters, (6) 1033-6, 1986, 1033-6, 1986.

Shafiee, A. et al: "Syntheses of 2-(2-arylethyl)imidazoels" XP002356157, Database Caplus, Database accession No. 1998:516917; Journal of Heterocyclic Chemistry, 35(3), 607-610, 1998.

Hinz, Werner et al: "Pyrrole studies: 34, Synthesis of 1, 2-di(2-pyrrolyl)ethenes and related compounds", XP00235618, Database Caplus, Database accession No. 1987:176094; Synthesis, (8), 620-3, 1986.

Greenhouse, Robert et al: Synthesis of alkylpyrroles by the sodium borohydride reduction of acylpyrroles, XP002356159, Database Caplus, Database accession No. 1985:471148; Journal of Organic Chemistry, 50(16), 2961-5, 1985.

Kinoshita, Hideki et al: "Convenient and regioselective syntheses of 3,4-disubstituted .DELTA. 3-pyrrolin-2-one derivatives starting from 2-tosyl-3, 4-disubstituted pyrroles", XP002356160, Database Caplus, Database accession No. 1994-134181; Chemistry Letters, (8), 1437-40, 1993.

Hopman, Johan C. P. et al: "Chirality preservatin in pyrolinone iron tetracarbonyl complexes—a route to enantiopure 5-substituted pyrrolinones", XP002356161, Database Caplus, Database accession No. 1995-488644; Journal of the Chemical Society, Chemical Communications, (6), 617-18, 1995.

Heinisch, Gottfired et al: "Pyrazoles II. The chemistry of pyrazolylalkynes", XP002356162, Database Caplus, Database accesssion No. 1988:510317; Monatshefte Fuer Chemie, 119(2), 253-62, 1988.

Moylan, Christopher R. et al: "The hyperpolarizabilities of tolanes and pyridyl analogues", XP002356163, Database Caplus, Database accession No. 1995:386546; MCLC S&T, Section B: Nonlinear Optics, 6(2), 113-21, 1993.

* cited by examiner

DIARYLSULFONES AS 5-HT2A ANTAGONISTS

CROSS REFERENCE TO RELATED APPLICATIONS

This application is a division of application Ser. No. 11/212,789, filed Aug. 26, 2005 now U.S. Pat. No. 7,217,740, which claims priority under 35 U.S.C. § 119 from GB Application No. 0419192.0, filed Aug. 27, 2004.

The present invention relates to a class of sulfonyl derivatives which act on serotonin receptors (also known as 5-hydroxytryptamine or 5-HT receptors). More particularly, the invention concerns arylsulfonylstilbenes and derivatives thereof. These compounds are potent and selective antagonists of the human 5-HT$_{2A}$ receptor and are therefore useful as pharmaceutical agents, especially in the treatment and/or prevention of adverse conditions of the central nervous system, including sleep disorders such as insomnia, psychotic disorders such as schizophrenia and psychiatric disorders such as anxiety.

Compounds of the invention typically display more effective binding to the human 5-HT$_{2A}$ receptor than to other human receptors such as D$_2$, 5H$_{2C}$ and IKr receptors. They can therefore be expected to manifest fewer side-effects than compounds which do not discriminate in their binding affinity between such receptors. In particular these compounds have lower effects on the IKr receptors and there is a separation of the desired effect from side effects such as cardiac effects.

By virtue of their potent human 5-HT$_{2A}$ receptor antagonist activity, the compounds of the present invention are effective in the treatment of neurological conditions including sleep disorders such as insomnia, psychotic disorders such as schizophrenia, and also depression, anxiety, panic disorder, obsessive-compulsive disorder, pain, eating disorders such as anorexia nervosa, and dependency or acute toxicity associated with narcotic agents such as LSD or MDMA; and moreover are beneficial in controlling the extrapyramidal symptoms associated with the administration of neuroleptic agents. They may further be effective in the lowering of intraocular pressure, and may also be effective in treating menopausal symptoms, in particular hot flushes (see Waldinger et al, *Maturitas*, 2000, 36, 165-8).

Various classes of compounds containing inter alia a sulfonyl moiety are described in WO 00/43362, WO 96/35666, EP-A-0261688, EP-A-0304888, and U.S. Pat. Nos. 4,218,455 and 4,128,552, DE-A-3901735 and Fletcher et al, *J. Med. Chem.*, 2002, 45, 492-503. None of these publications, however, discloses or suggests the particular class of compounds provided by the present invention.

Certain phenylsulfonylstilbene derivatives have been disclosed in a non-pharmaceutical context (U.S. Pat. No. 3,256,340; *J. Am. Chem. Soc.*, 1962, 84, 2652-3).

The compounds according to the present invention are potent and selective 5-HT$_{2A}$ receptor antagonists, suitably having a human 5-HT$_{2A}$ receptor binding affinity (K$_i$) of 100 nM or less, typically of 50 nM or less and preferably of 10 nM or less. The compounds of the invention may possess at least a 10-fold selective affinity, suitably at least a 20-fold selective affinity and preferably at least a 50-fold selective affinity, for the human 5-HT$_{2A}$ receptor relative to the human dopamine D$_2$ receptor and/or the human IKr and/or 5-HT$_{2C}$ receptors. Preferred compounds show selectivities of at least 100-fold relative to the human 5-HT$_{2C}$ receptor.

The present invention provides a pharmaceutical composition comprising, in a pharmaceutically acceptable carrier, a compound of formula I:

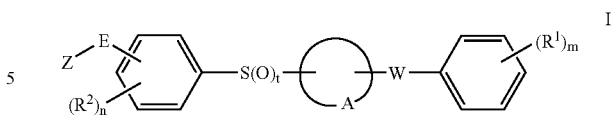

or a pharmaceutically acceptable salt or hydrate thereof; wherein:
m is 0, 1, 2 or 3;
n is 0, 1 or 2;
t is 1 or 2;

A represents the residue of a phenyl or 5- or 6-membered heteroaromatic ring optionally bearing up to 2 additional substituents selected from halogen, CN, CF$_3$, OR$^a$, CO$_2$R$^a$, CONR$^a$R$^b$, NR$^a$R$^b$ and C$_{1-4}$alkyl which is optionally substituted with halogen, CN, CF$_3$, OR$^a$, CO$_2$R$^a$, CONR$^a$R$^b$ or NR$^a$R$^b$;

W represents —CR$^3$R$^4$—CR$^5$R$^6$, —CR$^3$=CR$^5$— or —C≡C— where R$^3$, R$^4$, R$^5$, and R$^6$ are selected from H, OH and F but not more than one of R$^3$, R$^4$, R$^5$, and R$^6$ is other than H; or R$^3$ and R$^4$ together or R$^5$ and R$^6$ together complete a keto group; or R$^4$ and R$^6$ together complete a cyclopropyl ring;

E represents a chemical bond or a straight or branched alkylene chain containing from 1, to 4 carbon atoms, optionally incorporating an oxygen atom to form an ether linkage and optionally comprising a hydroxy substituent;

Z is selected from H, halogen, CN, nitro, CF$_3$, OCF$_3$, —R$^a$, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —NR$^a$CONR$^a$R$^b$, NR$^a$SOR$^b$, NR$^a$SO$_2$R$^b$, CONHCOR$^a$, NHCH$_2$CO$_2$R$^a$, NHCH$_2$CONR$^a$R$^b$, —NR$^a$SO$_2$NR$^a$R$^b$, —COR$^a$, —CO$_2$R$^a$, —CONR$^a$R$^b$, —CH=NOR$^a$ or a five- or six-membered heteroaromatic ring optionally bearing up to 2 substituents selected from halogen, CN, CF$_3$, C$_{1-6}$alkyl, C$_{1-6}$alkoxy, C$_{1-6}$alkylthio, amino, C$_{1-6}$alkylamino and di(C$_{1-6}$)alkylamino;

or the moiety -E-Z may combine with an adjacent R$^2$ group as defined below;

R$^a$ and R$^b$ independently represent H or a hydrocarbon group of up to 7 carbon atoms which is optionally substituted with up to 3 halogen atoms or with CN, OH, C$_{1-4}$alkoxy, C$_{1-4}$alkylthio, amino, C$_{1-4}$alkylamino or di(C$_{1-4}$)alkylamino; or R$^a$ and R$^b$, when linked through a nitrogen atom, together represent the residue of a heterocyclic ring of 4, 5 or 6 members, optionally bearing up to 3 substituents selected from halogen, CN, CF$_3$, oxo, OH, C$_{1-4}$alkyl and C$_{1-4}$alkoxy;

each R$^1$ independently represents halogen, CN, CF$_3$, OCF$_3$, C$_{1-6}$ alkyl, OH, benzylthio, C$_{1-6}$ alkoxy or hydroxymethyl; and each R$^2$ independently represents halogen, CN, CONH$_2$, C$_{1-4}$alkyl or C$_{1-4}$alkoxy; or an R$^2$ group and the moiety -E-Z when attached to adjacent ring positions may complete a fused 5- or 6-membered carbocyclic or heterocyclic ring optionally bearing up to 3 substituents selected from halogen, CN, CF$_3$, oxo, R$^a$ and amino.

In a particular embodiment, E represents a chemical bond or a straight or branched alkylene chain containing from 1 to 4 carbon atoms, optionally incorporating an oxygen atom to form an ether linkage; and Z is selected from halogen, CN, nitro, CF$_3$, OCF$_3$, —R$_a$, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —NR$^a$CO$_2$NR$^a$R$^b$, —NR$^a$SO$_2$NR$^a$R$^b$, —COR$^a$, —CO$_2$R$^a$, —CONR$^a$R$^b$, —CH=NOR$^a$ or a five- or six-membered heteroaromatic ring optionally bearing up to 2 substituents selected from halogen, CN, $CF_3$, $C_{1-6}$alkyl, $C_{1-6}$alkoxy, $C_{1-6}$alkylthio, amino, $C_{1-6}$alkylamino and di($C_{1-6}$)alkylamino.

In a further aspect, the invention provides a compound of formula I or a pharmaceutically acceptable salt or hydrate thereof as defined above, with the proviso that when A represents the residue of a phenyl ring and W represents —CH=CH— or —C≡C—, m is not zero and at least one $R^1$ represents F.

Where a variable occurs more than once in formula I or in a substituent group thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits unless otherwise indicated.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The term "halogen" as used herein includes fluorine, chlorine, bromine and iodine, of which fluorine and chlorine are preferred and fluorine particularly preferred.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The term "heteroaromatic" as used herein refers to aromatic rings having the indicated number of atoms of which at least one is N, O or S, the remainder being carbon atoms. In the case of 6-membered heteroaromatic rings, one, two or three (preferably one or two) of the ring atoms are nitrogen atoms. In the case of 5-membered heteroaromatic rings, one, two, three or four of the ring atoms are selected from N, O and S with the proviso that not more than one ring atom is O or S.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, benzenesulfonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

When the compounds according to the invention have one or more asymmetric centres, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, t is 1 or 2. In a preferred embodiment t is 2.

A represents the residue of a phenyl or a 5- or 6-membered heteroaromatic ring, any of which rings optionally bearing additional substitution as defined previously. Suitable 5-membered heteroaromatic rings typically comprise not more than 2 heteroatoms (selected from N, O and S), such as furan, thiophene, pyrrole, oxazole, thiazole, isoxazole, isothiazole, imidazole and pyrazole. Suitable 6-membered heteroaromatic rings typically comprise up to 3 nitrogen atoms, such as pyridine, pyrimidine, pyridazine, pyrazine and triazine. A preferably represents the residue of a phenyl or 6-membered heteroaromatic ring, most preferably phenyl or pyridyl. The ring completed by A preferably bears not more than one additional substituent. Typical substituents include halogen (such as Br and Cl), CN, $CONR^aR^b$ (such as $CONH_2$), $NR^aR^b$ (such as dimethylamino) and $C_{1-6}$alkyl which is optionally substituted with $OR^a$ or $NR^aR^b$ (such as hydroxymethyl, 1-hydroxyethyl or dimethylaminomethyl).

When the ring completed by A is 6-membered, W and E are preferably in the 1,4-configuration, and when the ring completed by A is 5-membered, W and E are preferably in the 1,3-configuration.

W represents —$CR^3R^4$—$CR^5R^6$—, —$CR^3$=$CR^5$— or —C≡C— where $R^3$, $R^4$, $R^5$, and $R^6$ are as defined previously. Suitable identities of W include —$CH_2CH_2$—, —$CHFCH_2$—, —$CH_2CHF$—, —$CH(OH)CH_2$—, —$CH_2CH(OH)$—, —$COCH_2$—, —$CH_2CO$—, —CH=CH—, —C≡C—, —CF=CH—, —CH=CF—, —C(OH)=CH—, —CH=C(OH)— and cyclopropane-1,2-diyl. It will be readily apparent that compounds of formula I in which W is —$COCH_2$— or —$CH_2CO$— are tautomeric with the corresponding compounds of formula I in which W is (respectively)-C(OH)=CH— or —CH=C(OH)—. Both forms, singly or in mixtures of any proportion, are within the scope of the invention. In one preferred embodiment, W represents —$CH_2CH_2$—. In another preferred embodiment, W represents —CH=CH—. When W represents —CH=CH—, the olefin double bond may be in either of the geometrical configurations, but is preferably in the E-configuration.

Where E represents a straight or branched alkylene chain, this may be, for example, methylene, ethylene, 1-methylethylene, propylene, 2-methylpropylene or butylene. The alkylene chain E may optionally incorporate an oxygen atom, thereby forming an ether linkage such as —$CH_2O$— or —$CH_2CH_2CH_2O$—. An alkylene chain represented by E may optionally comprise a hydroxyl substituent, i.e. it may incorporate a —CH(OH)— moiety. Moreover, E may represent a chemical bond such that the moiety Z is attached directly to the relevant phenyl ring depicted in formula I above.

Preferably, E represents a chemical bond or a methylene linkage.

In a specific embodiment, E represents a chemical bond.

In another specific embodiment, E represents a methylene linkage.

Z preferably represents halogen, CN, $CF_3$, $R^a$, $OR^a$, $SR^a$, $SO_2R^a$, $SO_2NR^aR^b$, $NR^aR^b$, $NR^aCOR^b$, $NR^aCONR^aR^b$, $NR^aSO_2NR^aR^b$, $COR^a$, $CO_2R^a$, $CONR^aR^b$, CH=$NOR^a$ or a five- or six-membered heteroaromatic ring optionally bearing up to 2 substituents as defined previously; or the moiety -E-Z combines with an adjacent $R^2$ group to complete a fused ring as defined previously. Further suitable identities for Z include $NR^aSOR^b$, $NR^aSO_2R^b$, $CONHCOR^a$, $NHCH_2CO_2R^a$, and $NHCH_2CONR^aR^b$.

Where the group Z represents an optionally substituted five-membered heteroaromatic ring, this is suitably a nitrogen-containing ring such as a pyrrole, imidazole, pyrazole, oxazole, thiazole, 1,3,4-oxadiazole, 1,2,4-oxadiazole, 1,3,4-thiadiazole, 1,2,4-thiadiazole, 1,2,3-triazole, 1,2,4-triazole or tetrazole ring, any of which optionally is substituted, typically by methyl. Such rings may be attached via a carbon atom or a nitrogen atom. Specific examples include pyrazol-1-yl, imidazol-1-yl, imidazol-2-yl and 2-methyl-1,2,4-triazol-3-yl.

Where the group Z represents an optionally substituted six-membered heteroaromatic ring, this is suitably a pyridine, pyrazine, pyrimidine, pyridazine or triazine ring, any of which optionally is substituted, typically by methyl or halogen. A specific example is 2-pyridyl.

$R^a$ and $R^b$ typically independently represent H, optionally substituted $C_{1-6}$alkyl (such as methyl, ethyl, propyl, 2,2,2-trifluoroethyl, 2-cyanoethyl, 1-hydroxyethyl and 2-hydroxyethyl), $C_{3-6}$cycloalkyl (such as cyclopropyl) or $C_{3-6}$cycloalkyl$C_{1-4}$alkyl (such as cyclopropylmethyl); or $R^a$ and $R^b$, when linked through a nitrogen atom, may together represent the residue of a heterocyclic ring of 4, 5 or 6 members optionally bearing up to 3 substituents as defined previously. Such rings typically comprise at most two heteroatoms selected from N, O and S, inclusive of the nitrogen atom connecting $R^a$ and $R^b$, for example azetidine, pyrrolidine, piperidine, tetrahydropyridine, piperazine, morpholine and thiomorpholine. Typical examples of cyclic groups represented by $NR^aR^b$ include azetidin-1-yl, 3,3-difluoroazetidin-1-yl, 3-hydroxyazetidin-1-yl, pyrrolidin-1-yl, 3-hydroxypyrrolidin-1-yl, 3-fluoropyrrolidin-1-yl, 2-trifluoromethylpyrrolidin-1-yl, piperidin-1-yl, 4-trifluoromethylpiperidin-1-yl, 3-trifluoromethylpiperidin-1-yl, 3-fluoropiperidin-1-yl, 3,3,-difluoropiperidin-1-yl, 4,4-difluoropiperidin-1-yl, 4-trifluoromethyl-1,2,3,6-tetrahydropyridin-1-yl, 4-methylpiperazin-1-yl, 3-oxo-piperazin-1-yl, morpholin-4-yl, 2,6-dimethylmorpholin-4-yl and 1,1-dioxo-thiomorpholin-4-yl.

When Z represents $R^a$, $R^a$ very suitably represents substituted $C_{1-6}$ alkyl, in particular hydroxy$C_{1-6}$alkyl such as hydroxymethyl or 1-hydroxyethyl, and E suitably represents a chemical bond.

When Z represents $OR^a$ or $SR^a$, $R^a$ typically represents $C_{1-6}$alkyl or phenyl which optionally bears a halogen substituent.

When Z represents $SOR^a$, $SO_2R^a$, $CONHCOR^a$, $NHCH^2CO_2R^a$ or $CO_2R^a$, $R^a$ typically represents $C_{1-6}$alkyl, such as methyl, ethyl, n-propyl, isopropyl or t-butyl.

When Z represents $COR^a$ or $CH=NOR^a$, $R^a$ typically represents H or $C_{1-6}$alkyl such as methyl or ethyl.

When Z represents $NR^aCOR^b$, $NR^aCO_2R^a$, $NR^aSOR^b$ or $NR^aSO_2R^b$, typically $R^a$ represents H and $R^b$ represents $C_{1-6}$alkyl, especially methyl.

When Z represents $SO_2NR^aR^b$, $NR^aCONR^aR^b$, $NHCH_2CONR^aR^b$, $NR^aSO_2NR^aR^b$ or $CONR^aR^b$, typically $R^a$ represents H and $R^b$ represents H or $C_{1-6}$alkyl, and preferably $R^a$ and $R^b$ both represent H.

The moiety -E-Z may be attached at any of the available ring positions, but is preferably in an ortho- or meta-position relative to the sulfone moiety, most preferably in an ortho-position.

The phenyl ring to which the moiety -E-Z is attached optionally bears up to two additional substituents $R^2$ as defined previously. Typically, n is 0 or 1 and hence not more than one $R^2$ group is present. When present, preferred identities for $R^2$ include halogen (especially F), CN and $CONH_2$.

In a particular embodiment, the moiety -E-Z and an R substituent are attached at adjacent ring positions and combine to complete a fused ring of 5 or 6 members. Said ring may be carbocyclic or heterocyclic and optionally bears up to 3 substituents selected from halogen, CN, $CF_3$, oxo, $R^a$ and amino. Heterocyclic embodiments typically comprise up to two ring atoms selected from N, O and S, the remainder being carbon. Fused rings of both types may be saturated or unsaturated, including aromatic. Preferred substituents, when present, include oxo and $C_{1-4}$alkyl (such as methyl). Examples of suitable rings include phenyl (completing a naphthalene system), cyclohexanone (completing an α-tetralone or β-tetralone system), cyclopentanone (completing an indan-1-one or indan-2-one system), δ-valerolactam (completing a tetrahydroquinolone or tetrahydroisoquinolone system), pyrrolidone (completing an indolinone or isoindolinone system), succinimide (completing a phthalimide system), imidazole (completing a benzimidazole system), pyrazole (completing an indazole system) and 1,4-dioxan.

In formula I, m represents 0, 1, 2 or 3, but preferably represents 1 or 2. Each $R^1$ is preferably selected from halogen (preferably F or Cl, most preferably F), CN, $C_{1-4}$alkyl (especially methyl), hydroxymethyl, OH and $C_{1-4}$alkoxy (e.g. methoxy). Specific embodiments of $(R^1)_m$ include H, 2-fluoro, 3-fluoro, 4-fluoro, 2,4-difluoro, 3-cyano, 4-cyano, 2-chloro-4-fluoro, 4-fluoro-2-methyl, 4-fluoro-2-hydroxy, 4-chloro, 2-hydroxy, 2-cyano-4-fluoro, 4-fluoro-2-methoxy, 4-fluoro-2-hydroxymethyl and 2-methyl. In a particular embodiment, $(R^1)_m$ represents 4-fluoro or 2,4-difluoro substitution of the phenyl ring.

In a particular aspect, the invention provides a compound of formula II:

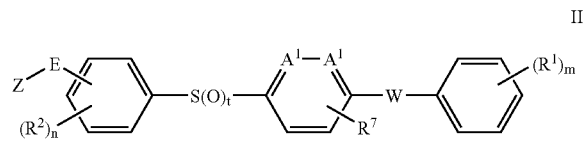

II or a pharmaceutically acceptable salt or hydrate thereof;

wherein each $A^1$ represents CH or N provided at least one $A^1$ is CH;

$R^7$ represents H, halogen, CN, $CF_3$, $OR^a$, $CO_2R^a$, $CONR^aR^b$, $NR^aR^b$ or $C_{1-4}$alkyl which is optionally substituted with halogen, CN, $CF_3$, $OR^a$, $CO_2R^a$, $CONR^aR^b$ or $NR^aR^b$;

and all other variables have the same definitions and preferred identities as before.

Preferably $R^7$ represents H, halogen (such as Br or Cl), CN, $CONR^aR^b$ (such as $CONH_2$), $NR^aR^b$ (such as dimethylamino) or $C_{1-6}$alkyl which is optionally substituted with $OR^a$ or $NR^aR^b$ (such as hydroxymethyl, 1-hydroxyethyl or dimethylaminomethyl).

In a subset of the compounds of formula II, both $A^1$ groups are CH. Within this subset, $R^7$ is preferably H. In the same subset, W is preferably CH=CH, —$CH_2CH_2$— or —$CH_2CO$—. In the same subset, the moiety Z-E very suitably represents hydroxy$C_{1-6}$alkyl.

In a further aspect, the invention provides a compound of formula III:

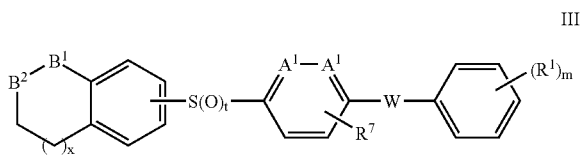

or a pharmaceutically acceptable salt or hydrate thereof;
wherein x is 0 or 1;
one of $B^1$ and $B^2$ is C=O and the other is N—$R^a$;
and all other variables have the same definitions and preferred identities as before.

Within this aspect, $R^a$ is preferably H or $C_{1-4}$alkyl (such as methyl).

In a particular embodiment, $B^1$ is C=O and $B^2$ is N—$R^a$.

In a further aspect, the invention provides a compound of formula IV:

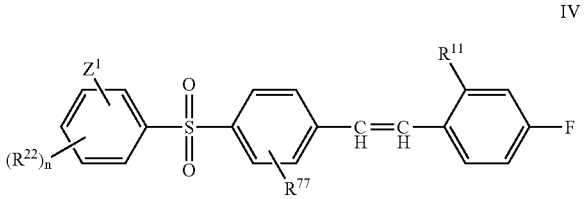

or a pharmaceutically acceptable salt or hydrate thereof;
wherein:
n is 0 or 1;
$R^{11}$ represents H or F;
$R^{22}$ represents halogen, CN, $CONH_2$, $C_{1-4}$alkyl or $C_{1-4}$alkoxy;
$R^{77}$ represents H or $C_{1-4}$alkyl; and
$Z^1$ represents hydroxy$C_{1-6}$alkyl, or $C_{1-6}$alkoxycarbonyl, or a 5- or 6-membered heteroaromatic ring which optionally bears a methyl substituent.

In formula IV, $R^{11}$ represents H or F. In a particular embodiment, $R^{11}$ represents H.

In formula IV, n is 0 or 1. In a particular embodiment, n is 0. When present, $R^{22}$ may be attached at any of the available ring positions, but is preferably in an ortho- or meta-position relative to the sulfone moiety, most preferably in an ortho-position. Suitable identities for $R^{22}$ include halogen (especially fluorine), $C_{1-4}$alkyl (especially methyl), $C_{1-4}$alkoxy (such as methoxy), CN and $CONH_2$. In a preferred embodiment, $R^{22}$ is either absent or represents methyl.

In formula IV, $R^{77}$ represents H or $C_{1-4}$alkyl, and when $R^{77}$ represents $C_{1-4}$alkyl said alkyl group may be attached at any of the available ring positions, but is most suitably attached in the ortho-position relative to the olefinic moiety. Preferably, $R^{77}$ represents H or methyl, most preferably H.

The olefinic double bond in formula IV may be in either of the geometrical configurations, but is preferably in the E-configuration.

The group $Z^1$ may be attached at any of the available ring positions, but is preferably in an ortho- or meta-position relative to the sulfone moiety, most preferably in an ortho-position.

In one embodiment of this aspect of the invention, $Z^1$ represents a hydroxy$C_{1-6}$alkyl group. In this embodiment, the alkyl group may be linear or branched, and preferably contains up to 4 carbon atoms. The hydroxyl group may be attached at any available position on said alkyl group, to form a primary, secondary or tertiary alkanol. Examples of suitable hydroxy$C_{1-6}$alkyl groups include hydroxymethyl, 1-hydroxyethyl, 2-hydroxyethyl and 2-hydroxy-2-propyl, of which 1-hydroxyethyl is particularly suitable. Said 1-hydroxyethyl group is very aptly in the S-configuration. Specific examples of compounds within this embodiment of the invention include:

(1S)-1-[2-({4-[(E)-2-(4-fluorophenyl)vinyl]phenyl}sulfonyl)phenyl]ethanol;

(1S)-1-[2-({4-[(E)-2-(2,4-difluorophenyl)vinyl]phenyl}sulfonyl)phenyl]ethanol;

(1S)-1-[2-({4-[(E)-2-(4-fluorophenyl)vinyl]-3-methylphenyl}sulfonyl)phenyl]ethanol;

[2-({4-[(E)-2-(4-fluorophenyl)vinyl]phenyl}sulfonyl)phenyl]methanol;

[2-({4-[(E)-2-(2,4-difluorophenyl)vinyl]phenyl}sulfonyl)phenyl]methanol;

2-[2-({4-[(E)-2-(4-fluorophenyl)vinyl]phenyl}sulfonyl)phenyl]propan-2-ol;

2-[2-({4-[(E)-2-(2,4-difluorophenyl)vinyl]phenyl}sulfonyl)phenyl]propan-2-ol; and 2-[2-({4-[(E)-2-(4-fluorophenyl)vinyl]phenyl}sulfonyl)phenyl]ethanol.

In a second embodiment of this aspect of the invention, $Z^1$ represents $C_{1-6}$alkoxycarbonyl, in particular $C_{1-4}$alkoxycarbonyl, such as $CO_2Me$, $CO_2Et$ and $CO_2{}^iPr$. Specific examples of compounds within this embodiment of the invention include:

methyl 2-({4-[(E)-2-(2,4-difluorophenyl)vinyl]phenyl}sulfonyl)benzoate;

methyl 2-({4-[(E)-2-(4-fluorophenyl)vinyl]phenyl}sulfonyl)benzoate;

methyl 3-({4-[(E)-2-(4-fluorophenyl)vinyl]phenyl}sulfonyl)benzoate; and methyl 2-({4-[(E)-2-(4-fluorophenyl)vinyl]phenyl}sulfonyl)-3-methylbenzoate.

In a third embodiment of this aspect of the invention, $Z^1$ represents a 5- or 6-membered heteroaromatic ring which optionally bears a methyl substituent. Where the group $Z^1$ represents an optionally substituted five-membered heteroaromatic ring, this is preferably a nitrogen-containing ring such as a pyrrole, imidazole, pyrazole, oxazole, thiazole, 1,3,4-oxadiazole, 1,2,4-oxadiazole, 1,3,4-thiadiazole, 1,2,4-thiadiazole, 1,2,3-triazole, 1,2,4-triazole or tetrazole ring, any of which optionally is substituted by methyl. Such rings may be attached via a carbon atom or (when chemically-feasible) a nitrogen atom, but attachment via carbon is preferred. Suitable examples include pyrazol-1-yl, imidazol-1-yl, 2-methyl-1,2,4-triazol-3-yl, oxazol-2-yl, thiazol-2-yl, imidazol-2-yl, 1-methylimidazol-2-yl, pyrazol-3-yl, 1,2,3-triazol-4-yl and 1,3,4-oxadiazol-2-yl, of which imidazol-2-yl and 1,3,4-oxadiazol-2-yl are particularly suitable.

Where the group $Z^1$ represents an optionally substituted six-membered heteroaromatic ring, this is suitably a pyridine, pyrazine, pyrimidine, pyridazine or triazine ring, any of which optionally is substituted by methyl. Preferably, a 6-membered heteroaromatic ring represented by $Z^1$ contains at most 2 nitrogen atoms, and most preferably is pyridyl. Specific examples of 6-membered heteroaromatic ring represented by $Z^1$ include 2-pyridyl and 3-pyridyl.

Specific examples of compounds within this embodiment of the invention include:

2-[2-({4-[(E)-2-(2,4-difluorophenyl)vinyl]phenyl}sulfonyl)
phenyl]-1H-imidazole;
2-[2-({4-[(E)-2-(4-fluorophenyl)vinyl]phenyl}sulfonyl)phenyl]-1H-imidazole;
2-[2-({4-[(E)-2-(2,4-difluorophenyl)vinyl]phenyl}sulfonyl)
phenyl]-1,3,4-oxadiazole; and
2-[2-({4-[(E)-2-(4-fluorophenyl)vinyl]phenyl}sulfonyl)phenyl]-1,3,4-oxadiazole.

Specific compounds of this invention include those compounds exemplified hereinafter and their pharmaceutically acceptable salts.

The compounds of the present invention have an activity as antagonists of the human $5\text{-HT}_{2A}$ receptor and hence find use in the treatment or prevention of disorders mediated by $5\text{-HT}_{2A}$ receptor activity.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly (ethylene glycol), poly(vinylpyrrolidone) or gelatin.

The present invention also provides a compound of formula I or a pharmaceutically acceptable salt or hydrate thereof for use in a method of treatment of the human body. Preferably the treatment is for a condition mediated by $5\text{-HT}_{2A}$ receptor activity.

The present invention further provides the use of a compound of formula I or a pharmaceutically acceptable salt or hydrate thereof in the manufacture of a medicament for treating or preventing a condition mediated by $5\text{-HT}_{2A}$ receptor activity.

Also disclosed is a method of treatment of a subject suffering from or prone to a condition mediated by $5\text{-HT}_{2A}$ receptor activity which comprises administering to that subject an effective amount of a compound according to formula I or a pharmaceutically acceptable salt or hydrate thereof.

In one aspect of the invention, the condition mediated by $5\text{-HT}_{2A}$ receptor activity is sleep disorder, in particular insomnia. In a further aspect of the invention, the condition mediated by $5\text{-HT}_{2A}$ receptor activity is selected from psychotic disorders (such as schizophrenia), depression, anxiety, panic disorder, obsessive-compulsive disorder, pain, eating disorders (such as anorexia nervosa), dependency or acute toxicity associated with narcotic agents such as LSD or MDMA, and hot flushes associated with the menopause.

In the treatment envisaged herein, for example of insomnia or schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day but preferably once per day, for example before going to bed.

If desired, the compounds according to this invention may be co-administered with another sleep inducing or anti-schizophrenic or anxiolytic medicament. Such co-administration may be desirable where a patient is already established on sleep inducing or anti-schizophrenic or anxiolytic treatment regime involving other conventional medicaments. In particular, for the treatment of sleep disorders, the compounds of the invention may be co-administered with a $GABA_A$ receptor agonist such as gaboxadol, or with a short term and/or rapid-onset hypnotic such as zolpidem, or a benzodiazepine, a barbiturate, a prokineticin modulator, an antihistamine, trazodone, or derivative of trazodone as disclosed in WO 03/068148.

According to a further aspect of the invention, there is provided the combination of a compound of formula I or a pharmaceutically acceptable salt or hydrate thereof and gaboxadol for use in treatment or prevention of sleep disorders, schizophrenia or depression.

Also according to the invention, there is provided a method of treatment or prevention of sleep disorders, schizophrenia or depression comprising administering to a subject in need thereof a compound of formula I or a pharmaceutically acceptable salt or hydrate thereof in combination with gaboxadol.

As used herein, the expression "in combination with" requires that therapeutically effective amounts of both a compound of formula I or a pharmaceutically acceptable salt or hydrate thereof and gaboxadol are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible.

According to a further aspect of the invention there is provided a pharmaceutical composition comprising, in a pharmaceutically acceptable carrier, a compound of formula I or a pharmaceutically acceptable salt or hydrate thereof and gaboxadol.

The invention further provides the use, for the manufacture of a medicament for treatment or prevention of sleep disorders, schizophrenia or depression, of a compound of formula I or a pharmaceutically acceptable salt or hydrate thereof and gaboxadol.

The invention further provides a kit comprising a first medicament comprising a compound of formula I or a pharmaceutically acceptable salt or hydrate thereof and a second medicament comprising gaboxadol together with instructions for administering said medicaments sequentially or simultaneously to a patient suffering from a sleep disorder, schizophrenia or depression.

As used herein, the term "gaboxadol" is inclusive of 4,5,6,7-tetrahydroisoxazolo[5,4-c]pyridin-3-ol in free base or zwitterionic form and also of pharmaceutically acceptable acid addition salts thereof such as the hydrochloride salt. Most suitably, gaboxadol is in the form of a crystalline monohydrate of the zwitterionic form, as disclosed in GB 2,410,434, the contents of which is incorporated herein in its entirety.

Compounds of formula I in which W is —CH═CH— may be obtained by reacting a compound of formula (1a) with a styrene of formula (2a):

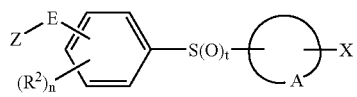

(1)

(a) X = Hal
(b) X = CHO

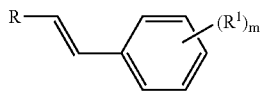

(2)

(a) R = H
(b) R = B(OH)$_2$ where Hal represents Cl or Br or I and all other variables have the same meanings as before. The reaction takes place at elevated temperature (e.g. 130° C.) in 1-methylpyrrolidone in the presence of palladium acetate and sodium acetate. "Hal" is preferably Br.

Alternatively, the compound of formula (1a) may be reacted with a boronic acid derivative (2b), typically in THF solution in the presence of (PPh$_3$)$_4$Pd[0] and a base such as sodium carbonate with heating (e.g. to 150° C. via microwave irradiation).

In a further alternative, an aldehyde of formula (1b) is coupled with a benzylphosphonate such as (3a) or a benzylphosphonium salt such as (3b):

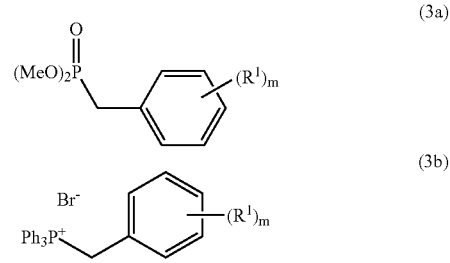

where $R^1$ and m have the same meanings as before. The reaction may be carried out in THF in the presence of strong base such as BuLi or the combination of sodium hydride with a crown ether.

In a further alternative, a compound of formula (1a) may be treated with tributyl(vinyl)tin to provide an alkene (4) which may be coupled with a bromobenzene (or iodobenzene) (5):

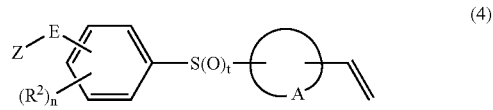

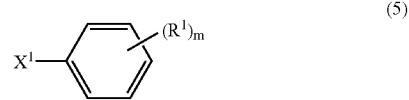

where $X^1$ represents Br or I and all other variables have the same meanings as before. The coupling takes place under similar conditions to the coupling of (1a) with (2a).

Compounds of formula (1a) and (1b) are obtainable by reaction of compounds (6) with compounds (7) followed by oxidation of the resulting thioether (8):

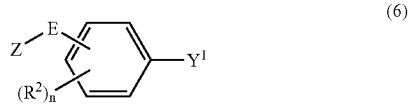

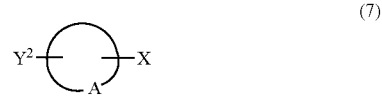

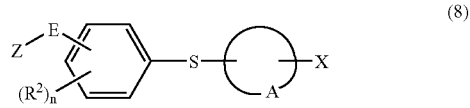

where either $Y^1$ is I and $Y^2$ is SH or $Y^1$ is SH and $Y^2$ is I, and all other variables have the same meanings as before. Formation of thioethers (8) takes place in the presence of CuI and ethylene glycol and a base such as potassium carbonate in a solvent such as isopropanol. Oxidation of thioethers (8) with one equivalent of oxidant (e.g. m-chloroperoxybenzoic acid) provides sulfoxides (1a) in which t=1. Use of excess oxidant, or a more vigorous oxidant such as oxone, provides sulfones (1a) in which t=2.

The aforementioned sulfones may also be obtained directly by the reaction between a compound of formula (6) and a compound of formula (7) wherein one of $Y^1$ and $Y^2$ is I or Br (preferably I) and the other is SO$_2^-$Na$^+$. This reaction may be carried out in a polar aprotic solvent such as DMSO at elevated temperature (eg. at about 110° C.) in the presence of a Cu(I) salt such as the iodide or triflate. Preferably, about 3 molar equivalents of the Cu(I) salt are used.

Compounds of formula I in which W is —CH$_2$CO— or its tautomeric form —CH═C(OH)— are obtainable by reaction of a compound of formula (1a) with an acetophenone (9):

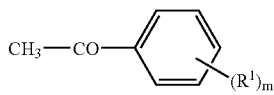
(9)

where R$^1$ and m have the same meaning as before. The reaction may be carried out in refluxing THF under N$_2$ in the presence of strong base such as sodium hydride.

Compounds of formula I in which W is —C≡C— may be obtained by reacting an aldehyde (1b) with diethyl(1-diazo-2-oxopropyl)phosphonate and coupling the resulting alkyne with the appropriate iodobenzene. The first step takes place in the presence of potassium carbonate in an alkanol, and the coupling reaction takes place in the presence of CuI and a Pd(II) catalyst such as (Ph$_3$P)$_2$PdCl$_2$.

Compounds of formula I in which W is —CH(OH)CH$_2$— may be obtained by reaction of an aldehyde (1b) with the appropriate benzylzinc halide. The reaction may be carried out in THF at −78° C. in the presence of a Cu(I) salt and BF$_3$ etherate.

Compounds of formula I in which W is —CH$_2$CH$_2$— may be obtained by hydrogenation of the corresponding compounds in which W is —CH═CH—, e.g. over Pd/C or PtO$_2$.

It will be readily apparent that it is possible to vary the order in which the reaction steps outlined above are carried out. For example, it is possible to couple a compound of formula (9), (2a), (2b), (3a) or (3b) with a compound of formula (7) (X═Hal or CHO as appropriate) and to react the product with a compound of formula (6) under similar conditions to those outlined above. Thus, a preferred synthesis of the compounds of formula IV comprises reaction of a bromo- or iodobenzene derivative (10) with a stilbenesulfinic acid salt (11):

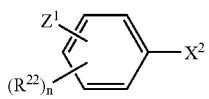
(10)

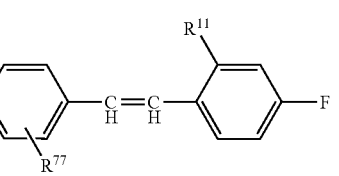
(11)

where X$^2$ represents Br or I and all other variables have the same meanings as before. Preferably, X$^2$ represents I and the reaction is carried out in DMSO at about 110° C. in the presence of CuI. The stilbene derivatives (11) may be prepared by coupling of compounds (2a), (2b), (3a) or (3b) with compounds of formula (7) wherein Y$^2$ represents SO$_2^-$Na$^+$ and X represents Hal or CHO as appropriate. During said coupling, the SO$_2^-$Na$^+$ group is preferably protected as the adduct with acrylonitrile. This may be achieved by reacting the relevant compound of formula (7) (Y$^2$═SO$_2^-$Na$^+$) with 2 equivalents of acrylonitrile in a mixture of acetic acid and water at 100° C. to form the corresponding arylsulfonylpropanenitrile. After coupling, the SO$_2^-$Na$^+$ functionality may be regenerated by treatment with alkoxide, e.g. sodium methoxide, at ambient temperature in an alcohol solvent, e.g. a methanol/THF mixture.

Where they are not themselves commercially available, the starting materials and reagents described above may be obtained from commercially available precursors by means of well known synthetic procedures and/or the methods disclosed in the Examples section herein.

It will be appreciated that any compound of formula I initially obtained from any of the above processes may, where appropriate, subsequently be elaborated into a further desired compound of formula I using techniques known from the art. For example, a compound of formula I initially obtained wherein the moiety Z-E- represents bromo may be converted into the corresponding compound of formula I wherein the moiety Z-E- represents cyano by treatment with copper(I) cyanide in the presence of 1-methyl-2-pyrrolidinone (NMP), or with zinc cyanide in the presence of tetrakis(triphenylphosphine)palladium(0). The resulting compound of formula I wherein the moiety Z-E- represents cyano thereby obtained may in turn be converted into the corresponding compound of formula I wherein the moiety Z-E- represents carboxamido by heating in mineral acid, e.g. 85% sulfuric acid at 100° C., or by treatment with potassium trimethylsilanolate, typically in tetrahydrofuran at reflux. Alternatively, a compound of formula I initially obtained wherein the moiety Z-E- represents bromo may be converted directly into the corresponding compound of formula I wherein the moiety Z-E- represents carboxamido by heating under a carbon monoxide atmosphere in the presence of 1,1,1,3,3,3-hexamethyldisilazane, diisopropylamine, palladium(II) acetate and 1,3-bis(diphenylphosphino)propane. Where, for example, the moiety Z-E- in the compounds of formula I represents an optionally substituted N-linked heterocyclic moiety, e.g. imidazol-1-yl, pyrazol-1-yl, 1,2,3-triazol-1-yl, 1,2,4-triazol-1-yl, pyrrolidin-1-yl, piperidin-1-yl or azetidin-1-yl, these compounds may be prepared by treating the corresponding compound of formula I wherein Z-E- represents fluoro with the appropriate optionally substituted N-heterocycle, typically with heating in DMSO. Where, for example, the moiety Z-E- in the compounds of formula I represents an optionally substituted C-linked five-membered heteroaromatic ring, e.g. 2-methyltetrazol-5-yl or 1-methyl-1,2,4-triazol-5-yl, these compounds may be prepared by reacting the corresponding compound of formula I wherein Z-E- represents bromo with a tributylstannyl derivative of the appropriate heteroaromatic compound, e.g. 2-methyl-5-tributylstannyltetrazole or 1-methyl-5-tributylstannyl-1,2,4-triazole, in the presence of a transition metal catalyst such as tetrakis(triphenylphosphine)palladium(0), typically with heating in a solvent such as N,N-dimethylformamide. Alternatively, a 5- or 6-membered heteroaromatic ring represented by Z may be constructed using conventional techniques of heterocyclic synthesis. For example, a methoxycarbonyl or ethoxycarbonyl group represented by Z may be converted to a 1,3,4-oxadiazol-2-yl group by sequential treatment with hydrazine hydrate and triethylorthoformate. Similarly, compounds in which Z represents 1,2,3-triazol-4-yl may be obtained by treatment of corresponding compounds in which Z is ethynyl with azidotrimethylsilane (e.g. in a sealed tube at 150° C. overnight). Similarly, compounds in which Z represents 1,2,4-triazol-3-yl may be obtained by treatment of corresponding compounds in which Z is CN with 4H-1,2,4-triazol-4-amine and sodium ethoxide in refluxing ethanol, followed by reaction of the resulting N'-4H-1,2,4-triazol-4-yl carboximidamide with ethyl chloroformate (e.g. in refluxing acetonitrile). Similarly, compounds in which Z represents thiazol-2-yl may be obtained by treatment of corresponding compounds in which Z is C(S)NH$_2$ with bromoacetaldehyde or its diethyl acetal (e.g. in refluxing ethanol). Similarly, compounds in which Z-E- represents 2-pyridyl may be obtained by diazotisation of corresponding compounds in which Z-E- is $NH_2$ and treatment of the resulting diazonium salts with excess pyridine (e.g. at 80° C.). Compounds of formula I in which Z-E- represents hydroxy$C_{1-6}$alkyl may be prepared by reduction of the corresponding aldehydes or ketones with sodium borohydride, or by reaction of the appropriate aldehyde or ketone with the appropriate alkyl Grignard reagent. A compound of formula I wherein, for example, Z represents $NR^aR^b$ and E is methylene may be prepared from the corresponding compound of formula I wherein the moiety Z-E- represents CHO, by treatment with $HNR^aR^b$ and sodium triacetyloxyborohydride or sodium cyanoborohydride; the compound of formula I wherein Z-E- represents CHO may suitably be prepared by diisobutylaluminium hydride (DIBAL-H) reduction and hydrolysis of the corresponding compound of formula I wherein Z-E- represents CN. Compounds in which Z-E- take the form Z-$(CH_2)_y$—O— where y is 1, 2, 3, or 4 may be formed by treating the corresponding compounds in which Z-E- is F with Z-$(CH_2)_y$OH in the presence of strong base.

Such processes may also be used to prepare appropriately-substituted precursors of the compounds of Formula I such as (6) or (10) and/or to introduce substituents to the ring A.

Similarly, compounds wherein W comprises CO may be reduced to provide corresponding compounds wherein W comprises CH(OH), e.g. using $NaBH_4$. These in turn may be treated with (diethylamino)sulfur trifluoride to provide compounds wherein W comprises CHF.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Compounds were tested for their binding to the $5\text{-HT}_{2A}$ receptor and to other receptors such as $5\text{-HT}_{2C}$ and IKr using the methodology described in Fletcher et al, *J. Med. Chem.*, 2002, 45, 492-503.

EXAMPLES

Intermediate 1

Sodium 4-[(E)-2-(4-fluorophenyl)vinyl]benzenesulfinate

Step 1

To a suspension of sodium 4-bromophenylsulfinate dihydrate (130 g, 0.53 mol) in water (600 mL) was added acrylonitrile (70 mL, 1.07 mol) and acetic acid (62 mL, 1.07 mol). The reaction was stirred for 1.5 h at 100° C. then cooled to room temperature. The solid was filtered off, washed thoroughly with water and dried over $P_2O_5$ to give 3-[(4-bromophenyl)sulfonyl]propanenitrile (125 g). $\delta_H$ (400, $CDCl_3$): 7.27-7.22 (4H, m), 2.85 (2H, t, J 7.6), 2.30 (2H, t, J 7.6).

Step 2

To a suspension of sodium acetate (54 g, 0.66 mol) and 4-fluorostyrene (90 g, 0.74 mol) in 1-methyl-2-pyrrolidinone (500 mL) was added 3-[(4-bromophenyl)sulfonyl]propanenitrile (Step 1, 90 g, 0.33 mol) and palladium (II) acetate (1.4 g, 6.2 mmol). The mixture was plunged into an oil-bath at 100° C. and heated to 135° C. for 20 minutes. The cooled reaction mixture was diluted with water and EtOAc and filtered through Hyflo®. The organic layer of the filtrate was washed with water (×3) then concentrated in vacuo. The residue was triturated with isohexane to give 3-({4-[(E)-2-(4-fluorophenyl)vinyl]phenyl}sulfonyl)propanenitrile (73 g). $\delta_H$ (360 MHz, $CDCl_3$): 7.88 (2H, d, J 8.0), 7.69 (2H, d, J 8.3), 7.51 (2H, dd, J 5.6, 8.3), 7.22 (1H, d, J 15.0), 7.10-7.02 (3H, m), 3.39 (2H, t, J 7.7), 2.83 (2H, t, J 7.7).

Step 3

To a mixture of 3-({4-[(E)-2-(4-fluorophenyl)vinyl]phenyl}sulfonyl)propanenitrile (Step 2, 75 g, 0.24 mol) in THF (1 L) and MeOH (500 mL) was added sodium methoxide (13 g, 0.24 mol). The mixture was stirred for 1 h at room temperature then diluted with isohexane and $Et_2O$. The solid was filtered off, triturated with isohexane and dried under vacuum to give sodium 4-[(E)-2-(4-fluorophenyl)vinyl]benzenesulfinate (66 g). $\delta_H$ (500 MHz, $d^6$ DMSO): 7.65 (2H, t, J 6.8), 7.53 (2H, d, J 7.8), 7.45 (2H, d, J 7.7), 7.26-7.18 (4H, m). m/z ($ES^-$) 261 [$(M-Na)^-$].

Intermediate 2

Sodium 4-[(E)-2-(2,4-difluorophenyl)vinyl]benzenesulfinate

Prepared in the same manner as Intermediate 1 using 2,4-difluorostyrene in place of 4-fluorostyrene in Step 2. $\delta_H$ (400 MHz, $d^6$ DMSO): 7.84 (1H, q, J 8.1), 7.55 (2H, d, J 8.0), 7.47 (2H, d, J 8.0), 7.32-7.20 (3H, m), 7.15-7.11 (1H, m). m/z ($ES^-$) 279 [$(M-Na)^-$].

Example 1

2-[(E)-2-(2,4-difluorophenyl)vinyl]-5-[(2-fluorophenyl)sulfonyl]pyridine

Step 1

2-chloro-5-iodopyridine (3.0 g, 12.5 mmol), 2-fluorobenzenethiol (1.6 g, 12.5 mmol), potassium carbonate (3.45 g, 25.0 mmol), ethylene glycol (1.55 g, 25.0 mmol) and copper (I) iodide (0.12 g, 0.63 mmol) were stirred in refluxing iso-propyl alcohol (50 mL) for 40 hours. Room temperature was attained, water was added and the products extracted into ethyl acetate (×2). The combined organic extracts were washed with brine, dried over $MgSO_4$ and concentrated in vacuo while loading onto silica. Dry flash column chromatography using isohexane-2% ethyl acetate/isohexane gave 2-chloro-5-[(2-fluorophenyl)thio]pyridine as a pale yellow oil (2.0 g, 67%). $\delta_H$ (500 MHz, $d^6$ DMSO): 7.25-7.29 (1H, m), 7.34-7.39 (1H, m), 7.44-7.51 (2H, m), 7.53 (1H, d, J=8.4 Hz), 7.75 (1H, dd, J=2.6, 8.4 Hz), 8.36 (1H, d, J=2.6 Hz); m/z ($ES^+$) 240, 242 [$MH^+$].

Step 2

The product from Step 1 (2.0 g, 8.3 mmol) and OXONE® (7.7 g, 12.5 mmol) were stirred in methanol (50 mL) at room temperature for 6 days. Saturated sodium bicarbonate was added and the suspension stirred for 15 minutes before diluting with water and extracting into ethyl acetate (×2). The combined organic extracts were washed with brine, dried over $MgSO_4$ and concentrated in vacuo while loading onto silica. Dry flash column chromatography using 10-30% ethyl acetate/isohexane gave 2-chloro-5-[(2-fluorophenyl)sulfonyl]pyridine as a white solid (1.95 g, 86%). $\delta_H$ (500 MHz, $d^6$ DMSO): 7.45-7.56 (2H, m), 7.81-7.88 (2H, m), 8.10 (1H, td, J=1.6, 7.6 Hz), 8.37-8.41 (1H, m), 8.98 (1H, d, J=2.6 Hz); m/z ($ES^+$) 272, 274 [$MH^+$].

Step 3

1-Ethynyl-2,4-difluorobenzene (9.6 g, 69.5 mmol) was warmed to 40° C. and catechol borane (8.3 g, 69.2 mmol) was added. The dark reaction mixture was stirred at 40° C. for 3 hours before stirring at 80° C. for 24 hours. Room temperature was attained and the mixture left to stand for 2 days. Water was added and the resulting dark solid collected by filtration. The solid was washed on the sinter with toluene to leave a beige solid, identified as [(E)-2-(2,4-difluorophenyl)vinyl]boronic acid and a mixture of anhydrides (3.8 g).

Step 4

The product from Step 3 (0.33 g), 2-chloro-5-[(2-fluorophenyl)sulfonyl]pyridine (Step 2, 0.41 g, 1.5 mmol) and tetrakis(triphenylphosphine)palladium(0) (40 mg) were dissolved in tetrahydrofuran/2N sodium carbonate (3 mL/1 mL) in a 5 mL microwave vial. The vial was heated to 150° C. for 10 minutes in a Smith synthesiser microwave reactor. Saturated ammonium chloride was added and the products extracted into ethyl acetate (×2). The combined organic extracts were washed with brine, dried over $MgSO_4$ and concentrated in vacuo while loading onto silica. Dry flash column chromatography using 10-25% ethyl acetate/isohexane gave the title compound as a beige solid (0.37 g, 66%). $\delta_H$ (500 MHz, $d^6$ DMSO): 7.20 (1H, td, J=2.2, 8.6 Hz), 7.36 (1H, m), 7.44-7.48 (1H, m), 7.50 (1H, d, J=16.1 Hz), 7.51-7.55 (1H, m), 7.80 (1H, d, J=8.6 Hz), 7.81-7.85 (1H, m), 7.91 (1H, d, J=16.1 Hz), 7.94-7.99 (1H, m), 8.11 (1H, td, J=1.5, 7.6 Hz), 8.33 (1H, dd, J=2.0, 8.3 Hz), 9.08 (1H, d, J=2.0 Hz); m/z ($ES^+$) 376 [$MH^+$].

Examples 2-5

The following 4 examples were prepared according to the method of Example 1 using 1-ethynyl-4-fluorobenzene in step 3. ([1,4-bis(diphenylphosphino)butane]-palladium(II) dichloride was used instead of $Pd(PPh_3)_4$ in Example 5 Step 4):

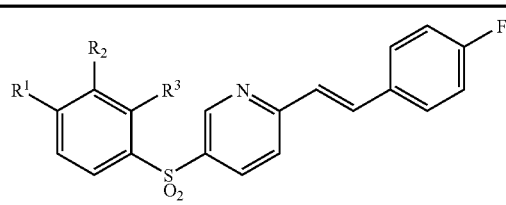

| Example | $R^1$ | $R^2$ | $R^3$ | m/z ($ES^+$) [$MH^+$] |
|---|---|---|---|---|
| 2 | F | H | H | 358 |
| 3 | H | H | H | 340 |

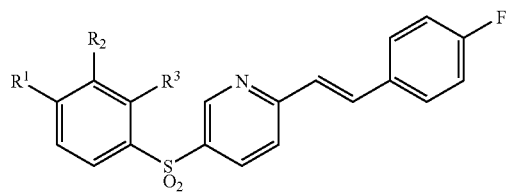

| Example | $R^1$ | $R^2$ | $R^3$ | m/z ($ES^+$) [$MH^+$] |
|---|---|---|---|---|
| 4 | H | H | F | 358 |
| 5 | H | F | H | 358 |

Example 6

2-[(E)-2-(2-fluorophenyl)vinyl]-5-[(2-fluorophenyl)sulfonyl]pyridine

Step 1

2-Chloro-5-[(2-fluorophenyl)sulfonyl]pyridine (Example 1 Steps 1 and 2, 410 mg, 1.52 mmol), tributyl(vinyl)tin (535 mg, 1.69 mmol) and tetrakis-(triphenylphosphine)palladium (0) (87 mg) were combined in tetrahydrofuran (10 mL) in three batches in 5 mL microwave vials. The vials were heated to 150° C. for 10 minutes in a Smith synthesiser microwave reactor. The combined reactions were diluted with ethyl acetate and washed with saturated aqueous ammonium chloride solution. The organic layers were dried over $MgSO_4$ and concentrated in vacuo while loading onto silica. Dry flash column chromatography using 10-20% ethyl acetate/isohexane gave 2-vinyl-5-[(2-fluorophenyl)sulfonyl]pyridine as a colourless solid (265 mg, 66%). $\delta_H$ (500 MHz, $d^6$ DMSO): 9.03 (1H, s), 8.30 (1H, dd, J=1.4, 8.3 Hz), 7.51 (1H, td, J=7.9, 0.85 Hz), 7.43 (1H, dd, J=9.1, 10.6 Hz), 6.92 (1H, dd, J=10.7, 17.4 Hz), 6.43 (1H, dd, J=1.2, 17.4 Hz), 5.70 (1H, dd, J=1.2, 10.7 Hz); m/z ($ES^+$) 364 [$MH^+$].

Step 2

2-Vinyl-5-[(2-fluorophenyl)sulfonyl]pyridine (Step 1, 50 mg, 0.19 mmol), 2-fluoroiodobenzene (46 mg, 0.207 mmol), palladium(II) acetate (2 mg, 0.01 mmol) and tri-o-tolylphosphine (12 mg, 0.039 mmol) were taken up in acetonitrile/triethylamine (0.5 mL/0.5 mL) and the reaction heated to 170° C. for 20 minutes in a Smith synthesiser microwave reactor. The reaction was diluted with ethyl acetate and washed with saturated aqueous ammonium chloride solution. The organic layers were dried over $MgSO_4$ and concentrated in vacuo. The residue was purified by mass-triggered preparative HPLC (Nebula) to give the title compound as a beige solid (39 mg, 57%). $\delta_H$ (500 MHz, $d^6$ DMSO): 9.03 (1H, d, J=2.2 Hz), 8.28 (1H, dd, J=1.6, 8.3 Hz), 8.05 (1H, td, J=7.6, 1.6 Hz), 7.92 (1H, d, I=16.1 Hz), 7.84 (1H, td, J=8.0, 1.4 Hz), 7.80-7.74 (2H, m), 7.47 (1H, d, J=16.1 Hz), 7.47 (1H, d, =0.7 Hz), 7.42-7.36 (2H, m), 7.27-7.21 (2H, m); m/z ($ES^+$) 358 [$MH^+$].

Examples 7-12

The following 6 examples were prepared according to the method of Example 6 using the appropriate iodobenzene in step 2:

| Example | $R^1$ | $R^2$ | m/z (ES$^+$) [MH$^+$] |
|---|---|---|---|
| 7 | Cl | F | 374 |
| 8 | Me | F | 372 |
| 9 | OH | F | 374 |
| 10 | OH | H | 356 |
| 11 | CN | F | 383 |
| 12 | OMe | F | 388 |

Example 13

(Z)-1-(2-benzylthio-4-fluorophenyl)-2-[5-(2-fluorophenylsulfonyl)pyridin-2-yl]ethylenol Step 1

Potassium tert-butoxide (7.3 g, 65.1 mmol) was dissolved in tetrahydrofuran (250 mL) and benzylthiol (7.52 mL, 64.1 mmol) in tetrahydrofuran (40 mL) was added via syringe over 10 minutes. The thick suspension was stirred for 15 minutes before adding 2,4-difluoroacetophenone (10 g, 64.1 mmol). The reaction was stirred for 1 hour to give a deep red solution. Saturated aqueous ammonium chloride was added and the products extracted into ethyl acetate (×2). The combined organic layers were dried over MgSO$_4$ and concentrated in vacuo. The residue was triturated with methanol to give 1-[2-(benzylthio)-4-fluorophenyl]ethanone (10.13 g, 61%).

Step 2

1-[2-(Benzylthio)-4-fluorophenyl]ethanone (Step 1, 0.84 g, 3.23 mmol) was dissolved in tetrahydrofuran (10 mL) and sodium hydride (60% dispersion in mineral oil; 0.28 g, 7.00 mmol) was added. The suspension was stirred at room temperature for 5 minutes then warmed to 60° C. and a suspension of 2-chloro-5-[(2-fluorophenyl)sulfonyl]pyridine (Example 1 Steps 1 and 2, 0.8 g, 2.94 mmol) in tetrahydrofuran (4 mL) was added. The reaction was stirred at 60° C. under nitrogen for 3 hours. The cooled reaction mixture was poured into saturated ammonium chloride solution and extracted with ethyl acetate. The combined organic extracts were washed with brine, dried over MgSO$_4$ and concentrated in vacuo. Recrystallisation from ethanol gave the title compound as a yellow solid (0.41 g, 28%). m/z (ES$^+$) 496 [MH$^+$].

Examples 14-15

The following 2 examples were prepared according to the method of Example 13 Step 2 using 2,4-difluoroacetophenone and the relevant 5-arylsulfonyl-2-chloropyridine:

| Example | $R^1$ | m/z (ES$^+$) [MH$^+$] |
|---|---|---|
| 14 | H | 374 |
| 15 | F | 392 |

Example 16

2-[(E)-2-(2,4-difluorophenyl)vinyl]-5-[(2-fluorophenyl)sulfinyl]pyridine

Step 1

2-Chloro-5-[(2-fluorophenyl)thio]pyridine (Example 1 Step 1, 1.0 g, 4.17 mmol) was taken up in dichloromethane (20 mL) and 3-chloroperoxybenzoic acid (50%; 1.44 g, 4.17 mmol). The reaction was stirred at room temperature under nitrogen for 1 hour. 4N sodium hydroxide solution was added and the products extracted into dichloromethane (×2). The combined organic layers were washed with brine, dried over MgSO$_4$ and concentrated in vacuo while loading onto silica. Dry flash column chromatography using toluene followed by 10% ethyl acetate/toluene gave 2-chloro-5-[(2-fluorophenyl)sulfinyl]pyridine (0.65 g, 61%). δ$_H$ (500 MHz, d$_6$ DMSO) 8.71 (1H, s), 8.07 (1H, d, J 8.2), 7.83 (1H, t, J 6.7), 7.68 (1H, d, J 8.2), 7.63-7.59 (1H, m), 7.46 (1H, t, J 7.3), 7.33 (1H, t, J 9.1); m/z (ES$^+$) 256, 258 [MH$^+$].

Step 2

As for Example 1 Step 4, using 2-chloro-5-[(2-fluorophenyl)sulfinyl]pyridine from Step 1 followed by recrystallisation from isopropyl alcohol. m/z (ES$^+$) 360 [MH$^+$].

Examples 17-20

The following 4 examples were prepared by analogy with Example 16:

| Example | $R^1$ | $R^2$ | $R^3$ | m/z (ES$^+$) [MH$^+$] |
|---|---|---|---|---|
| 17 | F | H | F | 342 |
| 18 | F | H | H | 324 |
| 19 | H | F | F | 342 |
| 20 | H | H | F | 324 |

Examples 21 and 22

(R)- and (S)-2-[(E)-2-(2,4-difluorophenyl)vinyl]-5-(phenylsulfinyl)pyridine

2-[(E)-2-(2,4-Difluorophenyl)vinyl]-5-(phenylsulfinyl)pyridine (Example 19) was separated into its enantiomers by chiral SFC: Chiracel OJ-H column (250×10 mm, 5 micron), mobile phase $CO_2$/MeOH 55/45, flow rate 10 ml/min. Peak 1 retention time 3.04 min (Example 21). Peak 2 retention time 3.61 min (Example 22). Example 21 m/z (ES$^+$) 342 [MH$^+$]. Example 22 m/z (ES$^+$) 342 [MH$^+$].

Example 23

2-[(E)-2-(2,4-difluorophenyl)vinyl]-5-[(2-(4-methylpiperazin-1-yl)phenyl)sulfonyl]pyridine 2-[(E)-2-(2,4-Difluorophenyl)vinyl]-5-[(2-fluorophenyl)sulfonyl]pyridine (Example 1, 30 mg, 0.08 mmol) and 1-methylpiperazine (22 µL, 0.20 mmol) were combined in acetonitrile (0.5 mL) and heated to 100° C. for 5 minutes in a Smith synthesiser microwave reactor. Further 1-methylpiperazine (44 µL, 0.40 mmol) was added and the reaction heated to 150° C. for 10 minutes, then to 170° C. for 10 minutes. The reaction mixture was diluted with ethyl acetate, washed with 1N aqueous hydrochloric acid and brine, dried over $MgSO_4$ and evaporated in vacuo to give the title compound which was dissolved in ethyl acetate and treated with ethereal HCl to give the hydrochloride salt (10 mg, 25%). $\delta_H$ (500 MHz, MeOD) 9.15 (1H, d, J 2.1), 8.30 (1H, dd, J=1.5, 7.9), 8.25 (1H, dd, J=2.3, 8.4 Hz), 7.96 (1H, d, J=16.3 Hz), 7.84-7.76 (3H, m), 7.56 (1H, td, J=1.1, 7.6 Hz), 7.50 (1H, d, J=7.9 Hz), 7.37 (1H, d, J=16.2 Hz), 7.07-7.03 (2H, m), 3.53 (2H, d, J=12.2 Hz), 3.21-3.14 (2H, m), 3.10 (4H, d, J=6.6 Hz), 3.03 (3H, s); m/z (ES$^+$) 456 [MH$^+$].

Examples 24-25

The following 2 examples were prepared by analogy with Example 23:

| Example | R$^1$ | m/z (ES$^+$) [MH$^+$] |
|---|---|---|
| 24 | pyrrolidinyl | 427 |
| 25 | dimethylamino | 401 |

Examples 26-28

The following 3 examples were prepared according to the methods of, sequentially, Example 1 Step 1 (using the appropriate thiophenol), Example 16 Step 1 (using 2-2.5 equivalents of 3-chloroperoxybenzoic acid) and Example 1 Step 4.

| Example | R$^1$ | R$^2$ | m/z (ES$^+$) [MH$^+$] |
|---|---|---|---|
| 26 | H | H | 358 |
| 27 | Br | H | 436, 438 |
| 28 | H | CN | 383 |

Example 29

2-[(E)-2-(2,4-difluorophenyl)vinyl]-5-[(2-fluorophenyl)sulfonyl]-6-chloropyridine Step 1

Urea-hydrogen peroxide (0.36 g, 3.83 mmol) was suspended in dichloromethane (3 mL) and trifluoroacetic anhydride (0.77 g, 3.67 mmol) was added to form a clear solution. 2-Chloro-5-[(2-fluorophenyl)sulfonyl]pyridine (Example 1 Steps 1 and 2, 0.5 g, 1.84 mmol) in dichloromethane (1 mL) was added and the reaction stirred at room temperature under nitrogen for 7 hours. The mixture was poured into water and extracted with ethyl acetate. The organic phase was washed with saturated aqueous sodium thiosulfate (×3). The combined aqueous layers were extracted once with ethyl acetate, then the combined organic layers washed again with sodium thiosulfate then with brine, dried over $MgSO_4$ and concentrated in vacuo to give 2-chloro-5-[(2-fluorophenyl)sulfonyl]pyridine 1-oxide as a pale yellow solid (0.53 g, quant.). $\delta_H$ (500 MHz, d$^6$ DMSO): 8.84 (1H, d, J=1.5 Hz), 8.08 (1H, td, J=7.5, 1.5 Hz), 8.03 (1H, d, J=8.6 Hz), 7.87-7.77 (2H, m), 7.51 (1H, q, J=8 Hz), 7.47 (1H, d, J=8.6 Hz); m/z (ES$^+$) 288[MH$^+$].

Step 2

2-Chloro-5-[(2-fluorophenyl)sulfonyl]pyridine 1-oxide from Step 1 (0.27 g, 0.938 mmol) was suspended in phosphorus oxychloride (10 mL) and stirred at 120° C. overnight. The cooled solution was poured into water and extracted with ethyl acetate (×2). The combined organic layers were washed with brine, dried over $MgSO_4$ and concentrated in vacuo while loading onto silica. Dry flash column chromatography using 10-20% ethyl acetate/isohexane gave the product 2,6-dichloro-5-[(2-fluorophenyl)sulfonyl]pyridine (115 mg) and impure product (100 mg). The latter material was recrystallised from ethanol to give further clean product (42 mg, total yield 55%). $\delta_H$ (400 MHz, d$_6$ DMSO): 8.68 (1H, dd, J=1.1, 8.3 Hz), 8.15 (1H, td, J=7.6, 1.7 Hz), 7.93 (1H, d, J=8.2 Hz), 7.89-7.85 (1H, m), 7.55 (1H, td, J=7.6, 0.9 Hz), 7.48-7.44 (1H, m); m/z (ES$^+$) 306, 308 [MH$^+$].

Step 3

As for Example 1 Step 4, followed by mass-triggered preparative HPLC (Nebula) to give the title compound as a white solid (18 mg, 45%). $\delta_H$ (500, CDCl$_3$): 8.64 (1H, dd, J=1.1, 8.1), 8.25 (1H, td, J=7.5, 1.7 Hz), 7.86 (1H, d, J=16.1), 7.68-7.64 (1H, m), 7.62-7.56 (1H, m), 7.49 (1H, d, J 8.1), 7.42-7.40 (1H, m), 7.17 (1H, d, J=16.0), 7.12 (1H, t, J=9.2), 6.95-6.91 (1H, m), 6.90-6.86 (1H, m); m/z (ES$^+$) 410, 412 [MH$^+$].

Example 30

2-[(E)-2-(2,4-difluorophenyl)vinyl]-5-({2-[(1-methyl-1H-1,2,4-triazol-5-yl)methoxy]phenyl}sulfonyl)pyridine 2-[(E)-2-(2,4-Difluorophenyl)vinyl]-5-[(2-fluorophenyl)sulfonyl]pyridine (Example 1, 50 mg, 0.13 mmol), 1-methyl-1H-1,2,4-triazol-5-yl)methanol (15 mg, 0.13 mmol), tetra-n-butylammonium sulfate (4 mg, 0.013 mmol) and 1M aqueous sodium hydroxide solution (0.52 mL) were combined in dichloromethane (0.52 mL) and stirred vigorously at room temperature for 4 hours then at 50° C. for 3 hours. Further reagents were added (until a total of 4 equivalents 1-methyl-1H-1,2,4-triazol-5-yl)methanol and 0.3 equivalents tetra-n-butylammonium sulfate) and heating continued for a further 21 hours at 50° C. The cooled reaction mixture was diluted with ethyl acetate, washed with 1M aqueous hydrochloric acid and brine, and dried over $MgSO_4$. The solvent was removed in vacuo and the residue purified by flash column chromatography on silica eluting with ethyl acetate to give the title compound (8 mg, 13%). $\delta_H$ (400 MHz, $CDCl_3$): 8.96 (1H, s), 8.17 (1H, dd, J=1.7, 7.9 Hz), 7.93-7.88 (2H, m), 7.82 (1H, d, J=16.2 Hz), 7.61-7.55 (2H, m), 7.30 (1H, s), 7.21-7.13 (3H, m), 6.93-6.83 (2H, m), 5.22 (2H, s), 4.00 (3H, s); m/z ($ES^+$) 469 [$MH^+$].

Example 31

2-[(E)-2-(2,4-difluorophenyl)vinyl]-5-(2-[3-(dimethylamino)-1-propoxy]phenylsulfonyl)pyridine 3-(dimethylamino)-1-propanol (17 µL, 0.14 mmol) was dissolved in N,N-dimethylformamide (1 mL) and sodium hydride (60% dispersion in mineral oil; 6 mg, 0.14 mmol) added. After stirring at room temperature under nitrogen for 10 minutes, a solution of 2-[(E)-2-(2,4-difluorophenyl)vinyl]-5-[(2-fluorophenyl)sulfonyl]pyridine (Example 1, 50 mg, 0.13 mmol) in N,N-dimethylformamide (1 mL) was added and the reaction stirred at room temperature under nitrogen for 3.5 days. The reaction was diluted with ethyl acetate and washed with water (×4) and brine, dried over $MgSO_4$ and evaporated in vacuo. The residue was purified by flash column chromatography on silica, eluting with 5% methanol/0.5% ammonia/dichloromethane, to give the title compound which was dissolved in ethyl acetate and treated with ethereal HCl to give the hydrochloride salt (42 mg, 66%). $\delta_H$ (400 MHz, MeOD): 9.10 (1H, d, J=2.2 Hz), 8.29 (1H, dd, J=2.3, 8.4 Hz), 8.12 (1H, dd, J=1.6, 7.9 Hz), 7.98 (1H, d, J=16.2 Hz), 7.83 (2H, q, J=7.9 Hz), 7.75-7.67 (1H, m), 7.38 (1H, d, J=16.3 Hz), 7.23 (1H, t, J=7.7 Hz), 7.18 (1H, d, J=8.3 Hz), 7.08-7.02 (2H, m), 4.22 (2H, t, J=5.7 Hz), 3.40 (2H, t, J=7.8 Hz), 2.97 (6H, s), 2.28-2.22 (2H, m); m/z ($ES^+$) 459 [$MH^+$].

Example 32

2-[(E)-2-(2,4-difluorophenyl)vinyl]-5-[(4-carboxamidophenyl)sulfonyl]pyridine

2-[(E)-2-(2,4-Difluorophenyl)vinyl]-5-[(4-cyanophenyl)sulfonyl]pyridine (Example 28, 100 mg, 0.26 mmol) and potassium trimethylsilanolate (67 mg, 0.52 mmol) were combined in toluene (5 mL) and heated to reflux under nitrogen for 2.5 hours. The resulting precipitate was collected by filtration and partitioned between water and dichloromethane. The aqueous layer was extracted with dichloromethane and the combined organic layers were dried over $MgSO_4$ and concentrated in vacuo. The residue was purified by trituration with isopropyl alcohol followed by dry flash column chromatography eluting with 3% methanol/dichloromethane to give the title compound as a beige solid (20 mg, 19%). $\delta_H$ (500 MHz, $d^6$ DMSO): 9.12 (1H, d, J=2.2 Hz), 8.35 (1H, dd, J=2.4, 8.3 Hz), 8.16 (1H, s), 8.10 (2H, d, J=8.5 Hz), 8.05 (2H, d, J=8.5 Hz), 7.93 (1H, q, J=8.0 Hz), 7.87 (1H, d, J=16.1 Hz), 7.75 (1H, d, J=8.3 Hz), 7.62 (1H, s), 7.45 (1H, d, J=16.1 Hz), 7.35-7.31 (1H, m), 7.17 (1H, td, J=2.0, 8.5 Hz).

Example 33

2-[(E)-2-(2,4-difluorophenyl)vinyl]-5-[(3-cyanophenyl)sulfonyl]pyridine

2-[(E)-2-(2,4-Difluorophenyl)vinyl]-5-[(3-bromophenyl)sulfonyl]pyridine (Example 27, 340 mg, 0.779 mmol) and zinc cyanide (110 mg, 0.93 mmol) were combined in N,N-dimethylformamide (5 mL) and degassed. Tetrakis-(triphenylphosphine)palladium(0) (68 mg, 0.059 mmol) was added and the reaction heated at 100° C. under nitrogen for 6 hours. Further tetrakis(triphenylphosphine)palladium(0) (60 mg) was added and heating continued for 18 hours. The cooled reaction mixture was partitioned between ethyl acetate and water. The aqueous layer was extracted with ethyl acetate and the combined organic layers dried over $MgSO_4$ and concentrated in vacuo. The residue was purified by mass-triggered preparative HPLC (Nebula) to give the title compound as a beige solid (56 mg, 19%). This was purified further by recrystallisation from isopropyl alcohol/dichloromethane. $\delta_H$ (500 MHz, $d^6$ DMSO): 9.16 (1H, s), 8.57 (1H, s), 8.40 (1H, dd, J=2.2, 8.4 Hz), 8.33 (1H, d, J=8.2 Hz), 8.18 (1H, d, J=78 Hz), 7.96-7.82 (3H, m), 7.76 (1H, d, J=8.3 Hz), 7.46 (1H, d, J=16.1 Hz), 7.36-7.31 (1H, m), 7.20-7.16 (1H, m); m/z ($ES^+$) 383 [$MH^+$].

Example 34

2-[(E)-2-(2,4-difluorophenyl)vinyl]-5-[(3-carboxamidophenyl)sulfonyl]pyridine

Prepared according to the method of Example 32 using the product of Example 33. m/z ($ES^+$) 401[$MH^+$].

Example 35

2-[(E)-2-(2,4-difluorophenyl)vinyl]-5-[(3-(morpholinomethyl)phenyl)sulfonyl]pyridine Step 1

A suspension of 2-[(E)-2-(2,4-difluorophenyl)vinyl]-5-[(3-cyanophenyl)-sulfonyl]pyridine (Example 33, 200 mg, 0.52 mmol) in dichloromethane (2 mL) and toluene (2 mL) was cooled in an ice-bath while stirring under nitrogen. Diisobutylaluminium hydride (1.5M in toluene, 0.38 mL, 0.57 mmol) was added and the reaction stirred at 0° C. then allowed to warm to room temperature over 3 hours. Methanol was added then 1N aqueous hydrochloric acid and the mixture left to stand overnight. The products were extracted into dichloromethane, dried over $MgSO_4$ and concentrated in vacuo. Dry flash column chromatography using 3% methanol/dichloromethane followed by recrystallisation from methanol gave 3-({6-[(E)-2-(2,4-difluorophenyl)vinyl]pyridin-3-yl}sulfonyl)benzaldehyde (93 mg, 46%). $\delta_H$ (400 MHz, $CDCl_3$): 9.07 (1H, d, J=2.2 Hz), 8.23-8.09 (3H, m), 7.89-7.81 (2H, m), 7.74-7.66 (1H, m), 7.61-7.55 (1H, m), 7.48-7.44 (1H, m), 7.25-7.16 (2H, m), 6.93-6.83 (2H, m); m/z (ES$^+$) 386 [MH$^+$].

Step 2

3-({6-[(E)-2-(2,4-Difluorophenyl)vinyl]pyridin-3-yl}sulfonyl)benzaldehyde (Step 1, 95 mg, 0.25 mmol) was suspended in methanol (1 mL) and acetic acid (70 μL). Morpholine (28 μL, 0.34 mmol) was added and the reaction stirred at room temperature under nitrogen for 30 minutes. Sodium cyanoborohydride (15 mg, 0.25 mmol) was added and stirring continued for 2 days. 5N sodium hydroxide was added and the products extracted into dichloromethane, washed with brine, dried over MgSO$_4$ and concentrated in vacuo. Purification by flash column chromatography (90% ethyl acetate/isohexane) gave the title compound as a yellow foam which was treated with ethereal HCl to give the hydrochloride salt (8 mg, 7%). $\delta_H$ (500 MHz, d$^6$ DMSO): 11.24 (1H, s), 9.11 (1H, d, J=2.1 Hz), 8.38 (1H, dd, J=2.1, 8.2 Hz), 8.33 (1H, s), 8.08 (1H, d, J=7.8 Hz), 7.93 (2H, q, J=8.0 Hz), 7.87 (1H, d, J=16.1 Hz), 7.76-7.70 (2H, m), 7.46 (1H, d, J=16.1 Hz), 7.37-7.31 (1H, m), 7.18 (1H, td, J=2.1, 8.4 Hz), 4.43 (2H, s), 3.91 (2H, d, J=11.8 Hz), 3.74 (2H, t, J=11.8 Hz), 3.20 (2H, d, J=11.6 Hz), 3.12-3.06 (2H, m); m/z (ES$^+$) 457 [MH$^+$].

Examples 36 and 37

2-[(4-fluorophenyl)sulfinyl]-5-[(E)-2-(4-fluorophenyl)vinyl]pyridine and 2-[(4-fluorophenyl)sulfonyl]-5-[(E)-2-(4-fluorophenyl)vinyl]pyridine Step 1

4-fluorobenzenethiol (0.32 g, 2.5 mmol) was taken up in acetonitrile (15 mL) and degassed for 15 minutes. 2-Chloro-5-iodopyridine (0.6 g, 2.51 mmol) and potassium carbonate (0.52 g, 3.76 mmol) were added and the reaction heated to reflux for 18 hours. The cooled reaction mixture was diluted with water and extracted with ethyl acetate (×2). The combined organic layers were washed with brine, dried over MgSO$_4$ and concentrated in vacuo while loading onto silica. Dry flash column chromatography using isohexane-2% ethyl acetate/isohexane gave a 3:1 mixture of 2-[(4-fluorophenyl)thio]-5-iodopyridine:2-chloro-5-iodopyridine (0.7 g). This was taken up in methanol (10 mL) and treated portionwise with OXONE® (1.04 g, 1.69 mmol). The suspension was stirred at room temperature for 5 days. A further portion of OXONE® (0.51 g) was added and stirring continued overnight. Saturated sodium hydrogencarbonate solution was added and the suspension stirred for 45 minutes before being extracted with ethyl acetate (×2). The combined organic layers were washed with brine, dried over MgSO$_4$ and concentrated in vacuo while loading onto silica. Dry flash column chromatography using 5-15% ethyl acetate/isohexane gave 2-[(4-fluorophenyl)sulfonyl]-5-iodopyridine (0.17 g), a 3.6:1 mixture of 2-[(4-fluorophenyl)sulfonyl]-5-iodopyridine:2-[(4-fluorophenyl)sulfinyl]-5-iodopyridine (0.2 g) and a 1.15:1 mixture of 2-[(4-fluorophenyl)sulfinyl]-5-iodopyridine:2-[(4-fluorophenyl)sulfonyl]-5-iodo-pyridine (0.14 g).

2-[(4-fluorophenyl)sulfonyl]-5-iodopyridine: $\delta_H$ (500 MHz, d$^6$ DMSO): 8.94 (1H, d, J=1.4 Hz), 8.53 (1H, dd, J=2.0, 8.2 Hz), 8.04-8.00 (2H, m), 7.98 (1H, dd, J=0.4, 8.2 Hz), 7.51-7.45 (2H, m); m/z (ES$^+$) 364 [MH$^+$].

Step 2

The 1.15:1 mixture of 2-[(4-fluorophenyl)sulfinyl]-5-iodopyridine:2-[(4-fluorophenyl)sulfonyl]-5-iodo-pyridine (Step 1, 0.14 g) was treated according to Example 1 Step 4 using (4-fluorophenyl)vinyl boronic acid to give the title compounds which were separated by dry flash column chromatography using 10-20% ethyl acetate/isohexane.

2-[(4-fluorophenyl)sulfinyl]-5-[(E)-2-(4-fluorophenyl)vinyl]pyridine: $\delta_H$ (500 MHz, d$^6$ DMSO): 8.77 (1H, d, J=1.9 Hz), 8.26 (1H, dd, J=2.1, 8.3 Hz), 7.95 (1H, d, J=8.2 Hz), 7.79-7.77 (2H, m), 7.65 (2H, dd, J=5.6, 8.7 Hz), 7.46 (1H, d, J=16.5 Hz), 7.40-7.36 (2H, m), 7.26-7.20 (3H, m); m/z (ES$^+$) 342 [MH$^+$].

2-[(4-fluorophenyl)sulfonyl]-5-[(E)-2-(4-fluorophenyl)vinyl]pyridine: $\delta_H$ (500 MHz, d$^6$ DMSO): 8.86 (1H, d, J=1.9 Hz), 8.30 (1H, dd, J=2.1, 8.3 Hz), 8.19 (1H, d, J=8.2 Hz), 8.05-8.03 (2H, m), 7.69-7.66 (2H, m), 7.55 (1H, d, J=16.5 Hz), 7.50-7.46 (2H, m), 7.29 (1H, d, J=16.5 Hz), 7.24 (2H, t, J=8.8 Hz); m/z (ES$^+$) 358 [MH$^+$].

Example 38

2-[(2-fluorophenyl)sulfonyl]-5-[(E)-2-(2,4-difluorophenyl)vinyl]pyridine

Prepared according to the method of Example 37 using (2-fluorophenyl)vinyl boronic acid. In the final step. m/z (ES$^+$) 376 [MH$^+$].

Example 39

2-[2-(4-fluorophenyl)ethyl]-5-[(4-fluorophenyl)sulfonyl]pyridine

5-[(4-fluorophenyl)sulfonyl]-2-[(E)-2-(4-fluorophenyl)vinyl]-pyridine (Example 2, 0.42 g, 1.18 mmol) was taken up in ethanol (5 mL) and ethyl acetate (5 mL) and palladium (10% wt. on activated carbon, 60 mg) was added. The suspension was shaken in a Parr apparatus at 20 psi hydrogen for 6 hours, followed by 40 psi hydrogen for 3 days. The catalyst was removed by filtration and the solvent removed in vacuo. The residue was taken up in acetic acid (25 mL) and platinum (IV) oxide (20 mg) was added. The suspension was stirred under a balloon of hydrogen for 20 hours. Further platinum (IV) oxide (20 mg) was added and stirring under hydrogen continued for 24 hours. The catalyst was removed by filtration and most of the solvent removed in vacuo. The residue was partitioned between ethyl acetate and 4N sodium hydroxide solution. The organic phase was dried over MgSO$_4$ and concentrated in vacuo while loading onto silica. Eluting through a plug of silica using 20% ethyl acetate/isohexane gave the title compound as a yellow solid (0.26 g, 61%). $\delta_H$ (500 MHz, d$^6$ DMSO): 9.04 (1H, d, J=2.2 Hz), 8.23 (1H, dd, J=2.4, 8.3 Hz), 8.09-8.07 (2H, m), 7.49-7.45 (3H, m), 7.22-7.19 (2H, m), 7.04 (2H, t, J=8.8 Hz), 3.11-3.09 (2H, m), 2.98-2.95 (2H, m); m/z (ES$^+$) 360 [MH$^+$].

Example 40

2-[2-(2,4-difluorophenyl)ethyl]-5-[(2-fluorophenyl)sulfonyl]pyridine

2-Vinyl-5-[(2-fluorophenyl)sulfonyl]pyridine (Example 6 Step 1; 50 mg, 0.19 mmol), 2,4-difluorophenylboronic acid (75 mg, 0.475 mmol), chloro(1,5-cyclooctadiene)rhodium(I) dimer (2 mg, 0.004 mmol) and sodium carbonate (40 mg, 0.377 mmol) were taken up in water (1 mL) and heated in a microwave reactor at 150° C. for 10 minutes. The dark suspension was diluted with water and extracted with ethyl acetate (×2). The combined organic layers were washed with brine, dried over MgSO$_4$ and concentrated while loading onto silica. Eluting through a plug of silica using 20% ethyl acetate/isohexane followed by mass-triggered preparative HPLC gave the title compound as a pale yellow solid (10 mg, 14%). $\delta_H$ (500 MHz, d$^6$ DMSO): 8.99 (1H, s), 8.21 (1H, dd, J=1.8, 8.3 Hz), 8.06 (1H, td, J=1.6, 7.6 Hz), 7.84-7.78 (1H, m), 7.52-7.48 (2H, m), 7.43 (1H, t, J=9.5 Hz), 7.28 (1H, q, J=8.0 Hz), 7.11 (1H, td, J=2.4, 9.9 Hz), 6.94 (1H, td, J=2.1, 8.5 Hz), 3.12-3.10 (2H, m), 3.01-2.98 (2H, m); m/z (ES$^+$) 378 [MH$^+$].

Example 41

1-(2,4-difluorophenyl)-2-[5-(phenylsulfonyl)pyridin-2-yl]ethanol (Z)-1-(2,4-difluorophenyl)-2-[5-(phenylsulfonyl)pyridin-2-yl]ethylenol (Example 14, 50 mg, 0.134 mmol) and sodium borohydride (10 mg, 0.265 mmol) were stirred in ethanol (3 mL) at room temperature for 6 hours. Water was added and the products extracted into ethyl acetate (×2). The combined organic layers were washed with brine, dried over MgSO$_4$ and concentrated in vacuo while loading onto silica. Dry flash column chromatography using 20-40% ethyl acetate/isohexane gave the title compound as a white solid (40 mg, 80%). $\delta_H$ (500 MHz, d$^6$ DMSO): 9.02 (1H, d, J=2.1 Hz), 8.23 (1H, dd, J=2.4, 8.2 Hz), 8.00-7.98 (2H, m), 7.72-7.69 (1H, m), 7.65-7.61 (2H, m), 7.54-7.49 (1H, m), 7.46 (1H, d, J=8.2 Hz), 7.12-7.08 (1H, m), 7.05-7.03 (1H, m), 5.52 (1H, d, J=3.7 Hz), 5.23-5.20 (1H, m), 3.13-3.05 (2H, m); m/z (ES$^+$) 376 [MH$^+$].

Example 42

2-[2-(2-hydroxy-4-fluorophenyl)ethyl]-5-[(2-fluorophenyl)sulfonyl]pyridine

2-[(E)-2-(2-Hydroxy-4-fluorophenyl)vinyl]-5-[(2-fluorophenyl)sulfonyl]pyridine (Example 9, 55 mg, 0.15 mmol) was dissolved in ethyl acetate (3 mL) and degassed. Palladium (10% wt. on activated carbon, 15 mg) was added and the reaction stirred under a balloon of hydrogen overnight, then under a fresh balloon for 3 days. The catalyst was removed by filtration and the solvent removed in vacuo. The residue was purified by flash column chromatography on silica eluting with 2:1 isohexane:ethyl acetate to give the title compound (8 mg, 14%). $\delta_H$ (400 MHz, CDCl$_3$): 9.67 (1H, s), 9.08 (1H, s), 8.25-8.22 (1H, m), 8.11-8.07 (1H, m), 7.63-7.58 (1H, m), 7.37-7.32 (2H, m), 7.15-7.09 (1H, m), 7.05-7.00 (1H, m), 6.58-6.50 (2H, m), 3.32 (2H, t, J=5.8 Hz), 3.07 (2H, t, J=6.0 Hz); m/z (ES$^+$) 376 [MH$^+$].

Example 43

2-[1-chloro-2-(2,4-difluorophenyl)ethyl]-5-(phenylsulfonyl)pyridine

Step 1

2-[(E)-2-(2,4-difluorophenyl)vinyl]-5-(phenylsulfonyl)pyridine (Example 26, 0.52 g, 1.45 mmol) and palladium hydroxide (20% wt. Pd on carbon, 100 mg, 0.14 mmol) were stirred in acetic acid (10 mL) and ethyl acetate (5 mL) under a balloon of hydrogen for 3 hours. The catalyst was removed by filtration and the filtrate washed with 4N sodium hydroxide solution (×2). The aqueous layers were extracted with dichloromethane. The combined organic extracts were dried over MgSO$_4$ and concentrated in vacuo to give 2-[2-(2,4-difluorophenyl)ethyl]-5-(phenylsulfonyl)pyridine as a pale yellow solid (0.49 g, 94%). $\delta_H$ (500 MHz, d$^6$ DMSO): 9.02 (1H, s), 8.23 (1H, dd, J=2.2, 8.2 Hz), 7.99 (2H, d, J=7.4 Hz), 7.70 (1H, t, J=7.4 Hz), 7.63 (2H, t, J=7.7 Hz), 7.48 (1H, d, J=8.2 Hz), 7.27 (1H, q, J=8.0 Hz), 7.11 (1H, td, J=2.0, 9.9 Hz), 6.94 (1H, td, J=1.9, 8.6 Hz), 3.07 (2H, t, J=7.7 Hz), 2.97 (2H, t, J=7.7 Hz); m/z (ES$^+$) 360 [MH$^+$].

Step 2

2-[2-(2,4-difluorophenyl)ethyl]-5-(phenylsulfonyl)pyridine 1-oxide was prepared from 2-[2-(2,4-difluorophenyl)ethyl]-5-(phenylsulfonyl)pyridine (Step 1) according to the method of Example 29 Step 1. m/z (ES$^+$) 376 [MH$^+$].

Step 3

2-chloro-6-[2-(2,4-difluorophenyl)ethyl]-3-(phenylsulfonyl)pyridine and the title compound were prepared from 2-[2-(2,4-difluorophenyl)ethyl]-5-(phenylsulfonyl)pyridine 1-oxide according to the method of Example 29 Step 2, separating the products by dry flash column chromatography using toluene-5% ethyl acetate/toluene. m/z (ES$^+$) 394, 396 [MH$^+$].

Example 44

6-[2-(2,4-difluorophenyl)ethyl]-2-methoxy-3-(phenylsulfonyl)pyridine

2-Chloro-6-[2-(2,4-difluorophenyl)ethyl]-3-(phenylsulfonyl)pyridine (Example 43 Step 3, 0.21 g, 0.53 mmol) and potassium hydroxide (90 mg, 1.60 mmol) were stirred in refluxing methanol (10 ml) for 6 hours. The cooled reaction mixture was diluted with water and extracted with ethyl acetate (×2). The combined organic layers were washed with brine, dried over MgSO$_4$ and concentrated in vacuo while loading onto silica. Dry flash chromatography using 10-15% ethyl acetate/isohexane gave the title compound as a colourless gum (150 mg, 72%). $\delta_H$ (500 MHz, d$^6$ DMSO): 8.25 (1H, d, J=7.7 Hz), 7.88 (2H, d, J=7.5 Hz), 7.69 (1H, t, J=7.4 Hz), 7.60 (2H, t, J=7.7 Hz), 7.27 (1H, q, J=8.0 Hz), 7.13-7.07 (2H, m), 6.94 (1H, td, J=2.1, 8.5 Hz), 3.78 (3H, s), 2.99-2.59 (4H, m); m/z (ES$^+$) 390 [MH$^+$].

Example 45

5-[2-(4-fluorophenyl)ethyl]-2-[(4-fluorophenyl)sulfonyl]pyridine

2-[(4-Fluorophenyl)sulfonyl]-5-[(E)-2-(4-fluorophenyl)vinyl]pyridine (Example 37, 0.11 g, 0.308 mmol) and palladium (10% wt. on activated carbon, 32 mg) were suspended in ethyl acetate (5 mL) and acetic acid (5 mL) and shaken in a Parr apparatus at 50 psi hydrogen for 2 days. The catalyst was removed by filtration, fresh catalyst (80 mg) added and shaking at 50 psi hydrogen continued for 10 days. The catalyst was removed by filtration and the solvent removed in vacuo. The residue was partitioned between saturated sodium carbonate solution and ethyl acetate. The aqueous phase was extracted with further portions of ethyl acetate and the combined organic layers were washed with brine, dried over MgSO$_4$ and concentrated in vacuo. The residue was purified by mass-triggered preparative HPLC (Nebula) to give the title compound as a beige solid (19 mg, 17%). $\delta_H$ (500 MHz, d$^6$ DMSO): 8.52 (1H, s), 8.10 (1H, d, J=8.0 Hz), 8.02-7.99 (2H, m), 7.95 (1H, dd, J=1.9, 8.0 Hz), 7.46 (2H, t, J=8.8 Hz), 7.21 (2H, dd, J=5.7, 8.4 Hz), 7.05 (2H, t, J=8.9 Hz), 2.97-2.94 (2H, m), 2.89-2.85 (2H, m); m/z (ES$^+$) 360 [MH$^+$].

Example 46

1-((E)-2-{4-[(2-bromophenyl)sulfonyl]phenyl}vinyl)-2,4-difluorobenzene

Step 1

4-fluorobenzaldehyde (10 mL, 93 mmol), 2-bromobenzenethiol (12 mL, 102 mmol) and potassium carbonate (15.4 g, 111 mmol) were combined in dimethylsulfoxide (50 mL) under nitrogen and heated to 120° C. After 2 hours, the temperature had reached 210° C. so the reaction was stopped. The cooled reaction mixture was partitioned between water and ethyl acetate. The organic layer was dried over $Na_2SO_4$ and the solvent removed in vacuo. The residue was purified by flash column chromatography on silica, eluting with 10% ethyl acetate/isohexane, to give 4-[(2-bromophenyl)thio]benzaldehyde (23.83 g, 87%). $\delta_H$ (360 MHz, $d^6$ DMSO): 9.97 (1H, s), 7.89-7.82 (3H, m), 7.55-7.33 (5H, m).

Step 2

To a solution of 4-[(2-bromophenyl)thio]benzaldehyde (Step 1, 5 g, 12.7 mmol) in ethanol under nitrogen (63 mL) was added sodium borohydride (5.7 g, 127.2 mmol). The reaction was stirred at room temperature for 1 hour. The solvent was removed in vacuo and the residue partitioned between ethyl acetate and water. The organic layer was dried over $Na_2SO_4$ and the solvent removed in vacuo. The residue was purified by flash column chromatography on silica, eluting with 40% ethyl acetate/isohexane, to yield {4-[(2-bromophenyl)thio]phenyl}methanol as a colourless oil (5.0 g, 99%). $\delta_H$ (400 MHz, $d^6$ DMSO): 7.65-7.60 (1H, m), 7.41 (4H, s), 7.27-7.21 (1H, m), 7.14-7.08 (1H, m), 6.83 (1H, dd, J=1.4, 7.9 Hz), 5.32-5.28 (1H, m), 4.56-4.53 (2H, m).

Step 3

To a solution of {4-[(2-bromophenyl)thio]phenyl}methanol (Step 2, 5.0 g, 16.9 mmol) in acetic acid (32 mL) was added hydrogen peroxide (4.2 mL, 50.8 mmol) and the reaction stirred overnight at room temperature. Further hydrogen peroxide (4.2 mL, 50.8 mmol) and catalytic sodium tungstate were added and the reaction stirred overnight. Water and ethyl acetate were added and the aqueous layer extracted with ethyl acetate (×2). The combined organic layers were washed with sodium hydrogen carbonate and brine, dried over $MgSO_4$ and concentrated in vacuo. The residue was purified by flash column chromatography on silica, eluting with 60% ethyl acetate/isohexane, to give {4-[(2-bromophenyl)sulfonyl]phenyl}methanol as a white solid (4.0 g, 80%). $\delta_H$ (400 MHz, $d^6$ DMSO): 8.31 (1H, dd, J=1.5, 7.9 Hz), 7.85 (2H, d, J=8.3 Hz), 7.79 (1H, d, J=7.9 Hz), 7.70 (1H, t, J=7.6 Hz), 7.60 (1H, td, J=1.0, 7.7 Hz), 7.54 (2H, d, J=8.3 Hz), 5.42 (1H, t, J=5.7 Hz), 4.57 (2H, d, J=5.4 Hz); m/z (ES$^+$) 327, 329 [MH$^+$].

Step 4

To a solution of oxalyl chloride (2.7 mL, 30.58 mmol) in dichloromethane (73 mL) at −78° C. under nitrogen was added dimethylsulfoxide (4.4 mL, 56.88 mmol) over 30 minutes. The mixture was stirred vigorously for a further 30 minutes then a solution of {4-[(2-bromophenyl)sulfonyl]phenyl}methanol (Step 3, 4.0 g, 12.23 mmol) in dichloromethane (24 mL) was added over 15 minutes. The reaction was stirred at −78° C. for 1 hour. Triethylamine (11.99 mL, 85.61 mmol) was added and stirring continued at −78° C. for 1 hour then the reaction was allowed to warm to room temperature. The pale yellow solution was diluted with dichloromethane, washed with sodium hydrogencarbonate solution, water and brine, dried over $MgSO_4$ and evaporated in vacuo. The residue was purified by flash column chromatography on silica, eluting with 30% ethyl acetate/isohexane, to give 4-[(2-bromophenyl)sulfonyl]benzaldehyde (3.41 g, 85%). $\delta_H$ (400 MHz, $d^6$ DMSO): 10.09 (1H, s), 8.37 (1H, dd, J=1.7, 7.9 Hz), 8.10 (4H, s), 7.83 (1H, dd, J=1.2, 7.9 Hz), 7.75 (1H, td, J=1.4, 7.7 Hz), 7.66 (1H, td, J=1.8, 7.7 Hz).

Step 5

4-[(2-bromophenyl)sulfonyl]benzaldehyde (Step 4, 3.4 g, 10 46 mmol), dimethyl (2,4-difluorobenzyl)phosphonate (2.36 g, 11.51 mmol) and 15-crown-5 (0.23 mL, 1.15 mmol) were dissolved in tetrahydrofuran (21 mL) under nitrogen and cooled to 0° C. Sodium hydride (276 mg) was added and the reaction allowed to warm slowly to room temperature. Saturated sodium carbonate solution and ethyl acetate were added. The organic layer was washed with brine, dried over $Na_2SO_4$ and evaporated in vacuo. The residue was purified by flash column chromatography on silica, eluting with 35% ethyl acetate/isohexane, to give 1-((E)-2-{4-[(2-bromophenyl)sulfonyl]phenyl}vinyl)-2,4-difluorobenzene as a white solid (3.1 g, 69%). $\delta_H$ (400 MHz, $d^6$ DMSO): 8.33 (1H, dd, J=1.7, 7.9 Hz), 7.89-7.81 (6H, m), 7.72 (1H, td, J=1.2, 7.6 Hz), 7.62 (1H, td, J=1.8, 7.6 Hz), 7.45-7.35 (2H, m), 7.33-7.29 (1H, m), 7.16 (1H, td, J=2.5, 8.3 Hz).

Example 47

2-({4-[(E)-2-(2,4-difluorophenyl)vinyl]phenyl}sulfonyl)benzonitrile

The title compound was prepared from 1-((E)-2-{4-[(2-bromophenyl)sulfonyl]phenyl}vinyl)-2,4-difluorobenzene (Example 46, 1.5 g, 3.45 mmol) according to the method of Example 33, heating at 85° C. for 3 hours and purifying by flash column chromatography on silica, eluting with 35% ethyl acetate/isohexane, followed by recrystallisation from 40% ethyl acetate/isohexane, to give 700 mg (53%). $\delta_H$ (500 MHz, $d^6$ DMSO): 8.33 (1H, d, J=7.9 Hz), 8.11 (1H, d, J=6.8 Hz), 8.02-7.97 (3H, m), 7.90-7.83 (4H, m), 7.41 (2H, q, J=18.0 Hz), 7.32-7.28 (1H, m), 7.15 (1H, td, J=2.0, 8.5 Hz).

Example 48

2-({4-[(E)-2-(2,4-difluorophenyl)vinyl]phenyl}sulfonyl)benzamide 2-({4-[(E)-2-(2,4-Difluorophenyl)vinyl]phenyl}sulfonyl)benzonitrile (Example 47, 100 mg, 0.26 mmol) was dissolved in ethanol (0.26 mL) and 4N sodium hydroxide (0.11 mL, 0.26 mmol) was added. The reaction was heated to 78° C. for 12 hours. After cooling, water and ethyl acetate were added. The aqueous layer was acidified with HCl and extracted with ethyl acetate (×2). The combined organic layers were dried over $Na_2SO_4$ and concentrated in vacuo. The residue was purified by flash column chromatography on silica, eluting with ethyl acetate, to yield the title compound as a white solid (54 mg, 52%). $\delta_H$ (400 MHz, $d^6$ DMSO): 8.09 (1H, dd, J=0.9, 7.8 Hz), 7.99 (2H, d, J=8.5 Hz), 7.95 (1H, s), 7.86 (1H, q, J=8.2 Hz), 7.80 (2H, d, J=8.5 Hz), 7.74-7.62 (2H, m), 7.58 (1H, s), 7.47-7.27 (4H, m), 7.15 (1H, td, J=1.7, 8.5 Hz); m/z (ES$^+$) 400 [MH$^+$], 383 [(MH$^+$)−17].

Example 49

3-({4-[(E)-2-(2,4-difluorophenyl)vinyl]phenyl}sulfonyl)benzonitrile

Prepared from Example 109 according to the method of Example 33. m/z (ES+) 382 [MH+].

Example 50

4-[3-({4-[(E)-2-(2,4-difluorophenyl)vinyl]phenyl}sulfonyl)benzyl]morpholine

Step 1

To a solution of 3-({4-[(E)-2-(2,4-difluorophenyl)vinyl]phenyl}sulfonyl)benzonitrile (Example 49, 400 mg, 1.05 mmol) in dichloromethane (2.1 mL) at −78° C. was added diisobutylaluminium hydride (1.0M, 1.15 mL, 1.15 mmol) dropwise and the reaction was stirred for 45 minutes. The solution was warmed to 0° C. and HCl (2.2 mL) was added slowly. The mixture was allowed to warm to room temperature and water and ethyl acetate were added. The organic layer was washed with sodium hydrogencarbonate and brine, dried over $Na_2SO_4$ and concentrated in vacuo. As hydrolysis was incomplete, the residue was taken up in toluene (10 mL) and methanol (1 mL), 5N HCl (3 mL) was added and the solution stirred for 2 hours. Water and ethyl acetate were added and the organic layer separated, dried over $Na_2SO_4$ and evaporated in vacuo to give 3-({4-[E)-2-(2,4-difluorophenyl)vinyl]phenyl}sulfonyl)benzaldehyde (323 mg, 80%). $\delta_H$ (500 MHz, $d^6$ DMSO): 10.07 (1H, d, J=6.1 Hz), 8.44 (1H, s), 8.28-8.25 (1H, m), 8.18-8.16 (1H, m), 7.98 (2H, d, J=8.5 Hz), 7.89-7.83 (4H, m), 7.43-7.34 (2H, m), 7.31-7.27 (1H, m), 7.15 (1H, td, J=2.0, 8.7 Hz).

Step 2

The title compound was prepared from the product of Step 1 by the procedure of Example 35 Step 2 and purified by flash column chromatography on silica, eluting with 90% ethyl acetate/isohexane. Treatment with ethereal HCl gave the hydrochloride salt. $\delta_H$ (400 MHz, $d^6$ DMSO): 11.54 (1H, s), 8.30 (1H, s), 7.98 (4H, q, J=10.2 Hz), 7.89-7.83 (3H, m), 7.70 (1H, t, J=7.8 Hz), 7.44-7.26 (3H, m), 7.15 (1H, td, J=2.2, 8.5 Hz), 4.43 (2H, s), 3.92-3.75 (4H, m), 3.20-3.06 (4H, m); m/z (ES+) 456 [MH+].

Examples 51-55

The following 5 examples were prepared according to the method of Example 46, using the appropriate thiophenol and benzaldehyde in Step 1.

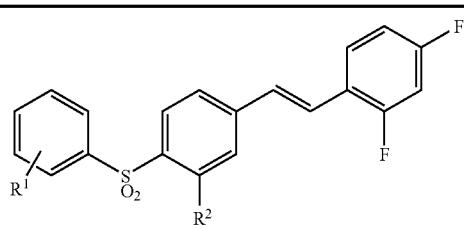

| Ex. | R¹ | R² | $\delta_H$ (400 MHz, $d^6$ DMSO) or m/z (ES+) |
|---|---|---|---|
| 51 | H | H | 7.96-7.92(4H m), 7.61-7.54(4H m), 7.53-7.50(2H m), 7.27(1H d, J=16.5Hz), 7.09(1H d, J=16.5Hz), 6.92-6.82 (2H m)(500 MHz, $CDCl_3$) |

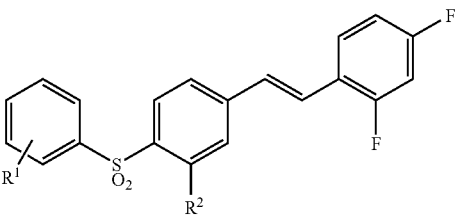

| Ex. | R¹ | R² | $\delta_H$ (400 MHz, $d^6$ DMSO) or m/z (ES+) |
|---|---|---|---|
| 52 | 3-F | H | 7.98(2H, d, J=8.5Hz), 7.89-7.81(5H, m), 7.71-7.65(1H, m), 7.58-7.54(1H, m), 7.39(2H, d, J=8.2Hz), 7.34-7.28 1H, m), 7.18-7.14(1H, m) |
| 53 | 4-CN | H | 8.15-8.13(2H, m), 8.10-8.08(2H, m), 7.98(2H, d, J=8.5 Hz), 7.89-7.83(3H, m), 7.45-7.35(2H, m), 7.33-7.27(1H, m), 7.15(1H, td, J=2.5, 8.5Hz) |
| 54 | 2-F | H | 8.06(1H, td, J=1.6, 7.7Hz), 7.93-7.85(5H, m), 7.81-7.75 (1H, m), 7.49(1H, td, J=1.0, 7.6Hz), 7.45-7.39(3H, m), 7.35-7.29(1H, m), 7.16(1H, td, J=2.3, 8.4Hz) |
| 55 | H | Br | 435, 437 [MH+] |

Example 56

2,4-difluoro-1-((E)-2-{4-[(4-fluorophenyl)sulfonyl]phenyl}vinyl)benzene

Butyllithium (1.6M in hexanes, 0.35 mL, 0.57 mmol) was added dropwise to a cooled (0° C.) suspension of (2,4-difluorobenzyl)triphenylphosphonium bromide (266 mg, 0.57 mmol) in tetrahydrofuran (2.5 mL). The orange suspension was allowed to warm to room temperature for 1 hour. A solution of 4-[(4-fluorophenyl)sulfonyl]benzaldehyde (prepared according to the method of Example 46 Steps 1-4 using 4-fluorobenzenethiol in Step 1, 150 mg, 0.57 mmol) in tetrahydrofuran (0.5 mL) was added and the reaction was stirred overnight at room temperature. Water and ethyl acetate were added and the organic layer was dried over $MgSO_4$ and evaporated in vacuo. The residue was purified by flash column chromatography on silica, eluting with 30% ethyl acetate/isohexane, followed by preparative HPLC to give the title compound (46 mg, 22%). 1H NMR δ (ppm)(DMSO): 8.01-7.99 (2H, m), 7.83 (2H, d, J=8.5 Hz), 7.47-7.42 (2H, m), 7.37 (2H, d, J=8.4 Hz), 7.27-7.17 (2H, m), 6.99 (1H, td, J=2.2, 8.6 Hz), 6.82 (1H, d, J=12.3 Hz), 6.70 (1H, d, J=12.0 Hz).

Example 57

4-({4-[(E)-2-(2,4-difluorophenyl)vinyl]phenyl}sulfonyl)benzamide

To a solution of 4-({4-[(E)-2-(2,4-difluorophenyl)vinyl]phenyl}sulfonyl)benzonitrile (Example 53, 50 mg, 0.13 mmol) in dimethylsulfoxide (1.3 mL) was added potassium carbonate (9 mg, 0.07 mmol) in water (0.65 mL) and the reaction stirred for 5 minutes. Hydrogen peroxide (0.06 mL) was added and the reaction stirred for 2 hours. Saturated aqueous sodium sufite solution was added and the products extracted into ethyl acetate. The organic layer was dried over $Na_2SO_4$ and evaporated in vacuo. The residue was purified by flash column chromatography on silica, eluting with ethyl acetate, to give the title compound as a white solid (51 mg, 98%). (400 MHz, $d^6$ DMSO): 8.15 (1H, s), 8.03 (4H, s), 7.96 (2H, d, J=8.5 Hz), 7.84 (3H, d, J=8.6 Hz), 7.61 (1H, s), 7.39 (2H, d, J=7.2 Hz), 7.33-7.27 (1H, m), 7.15 (1H, td, J=2.3, 8.6 Hz).

Example 58

5-[(E)-2-(2,4-difluorophenyl)vinyl]-2-(phenylsulfonyl)benzonitrile

2-Bromo-4-[(E)-2-(2,4-difluorophenyl)vinyl]-1-(phenylsulfonyl)benzene (Example 55, 130 mg, 0.3 mmol) and copper(I) cyanide (40 mg, 0.45 mmol) were combined in N,N-dimethylformamide (20 mL) and heated to 130° C. for 3 hours. Further copper(I) cyanide (40 mg, 0.45 mmol) was added and heating continued overnight. The cooled reaction mixture was diluted with water and extracted with ethyl acetate. The organic layer was washed with water (×3) and brine, dried over MgSO$_4$ and evaporated in vacuo. The residue was purified by flash column chromatography on silica, eluting with 20-30% ethyl acetate/isohexane, followed by trituration with diethyl ether to give the title compound (50 mg, 44%). $\delta_H$ (360 MHz, d$^6$ DMSO): 8.41 (1H, d, J=1.6 Hz), 8.28 (1H, d, J=8.4 Hz), 8.14 (1H, dd, J=1.7, 8.4 Hz), 8.01-7.98 (2H, m), 7.86-7.64 (4H, m), 7.58 (1H, d, J=16.6 Hz), 7.37 (1H, d, J=16.8 Hz), 7.32-7.28 (1H, m), 7.17 (1H, td, J=2.4, 8.5 Hz).

Example 59

1-fluoro-2-{(E)-2-[4-(phenylsulfonyl)phenyl]vinyl}benzene

Step 1

4-(Phenylsulfonyl)benzaldehyde (prepared according to the method of Ulman et al., *J. Org. Chem.* (1989), 54(19), 4691-2; 12.3 g, 50 mmol) was dissolved in tetrahydrofuran and methanol was added, followed by careful addition of sodium borohydride (2.0 g, 52.9 mmol). The reaction was stirred for 1 hour before pouring into water and extracting with ethyl acetate. The organic layer was dried over MgSO$_4$ and evaporated in vacuo to give [4-(phenylsulfonyl)phenyl]methanol. This was treated with phosphorus tribromide and heated to reflux for 16 hours. The cooled reaction mixture was poured onto ice and extracted with ethyl acetate. The organic layer was dried over MgSO$_4$ and evaporated in vacuo. The residue was purified by flash column chromatography on silica, eluting with dichloromethane, to give 1-(bromomethyl)-4-(phenylsulfonyl)benzene (10.1 g, 65%). $\delta_H$ (500 MHz, CDCl$_3$): 7.96-7.90 (4H, m), 7.59-7.56 (1H, m), 7.52-7.49 (4H, m).

Step 2

1-(Bromomethyl)-4-(phenylsulfonyl)benzene (Step 1, 10.1 g, 32.5 mmol) was heated to reflux in trimethylphosphite (40 mL) for 16 hours. The cooled reaction was azeotroped with xylene then purified by flash column chromatography on silica, eluting with ethyl acetate to give dimethyl[4-(phenylsulfonyl)benzyl]phosphonate (9.5 g, 86%). $\delta_H$ (360 z, CDCl$_3$): 7.92-7.84 (4H, m), 7.55-7.39 (5H, m), 3.64 (6H, d, J=10.9 Hz), 3.16 (2H, d, J=21.6 Hz).

Step 3

The title compound was prepared from dimethyl[4-(phenylsulfonyl)benzyl]phosphonate (Step 2) and 2-fluorobenzaldehyde according to the method of Example 46 Step 5. $\delta_H$ (500 MHz, CDCl$_3$): 7.97-7.92 (4H, m), 7.63-7.55 (4H, m), 7.52-7.49 (2H, m), 7.35 (1H, d, J=16.5 Hz), 7.30-7.25 (1H, m), 7.18-7.14 (2H, m), 7.10-7.06 (1H, m).

Examples 60-62

The following 3 examples were prepared according to the method of Example 59 using the appropriate benzaldehyde in the final step:

| Example | R | $\delta_H$ (500 MHz, CDCl$_3$) |
|---|---|---|
| 60 | F | 7.96-7.91(4H, m), 7.59-7.54(3H, m), 7.52-7.47(4H, m), 7.15(1H, d, J=16.3Hz), 7.08-7.01(2H, m), 6.99 (1H, d, J=16.3Hz) |
| 61 | CN | 7.95(4H, dd, J=6.6, 8.3Hz), 7.66-7.56(7H, m), 7.53-7.50(2H, m), 7.18(2H, s) |
| 62 | H | 7.97-7.91(4H, m), 7.61-7.54(3H, m), 7.52-7.49(4H, m), 7.39-7.36(2H, m), 7.32-7.29(1H, m), 7.20(1H, d, J=16.3Hz), 7.08(1H, d, J=16.3Hz) |

Example 63

5-[(E)-2-(2,4-difluorophenyl)vinyl]-2-(phenylsulfonyl)benzamide

Prepared from Example 58 according to the method of Example 57. m/z (ES$^+$) 400 [MH$^+$].

Example 64

1-{5-[(E)-2-(2,4-difluorophenyl)vinyl]-2-(phenylsulfonyl)phenyl}ethanol

A solution of 5-[(E)-2-(2,4-difluorophenyl)vinyl]-2-(phenylsulfonyl)benzaldehyde (prepared from Example 58 according to the method of Example 50 Step 1, 74 mg, 0.193 mmol) in tetrahydrofuran (2 mL) was cooled to −78° C. under nitrogen. Methylmagnesium chloride (3.0M in tetrahydrofuran, 0.15 mL, 0.424 mmol) was added and the reaction stirred for 30 minutes then quenched with 1N HCl (5 mL) and extracted with ethyl acetate. The organic layer was washed with brine, dried over MgSO$_4$ and evaporated in vacuo. The residue was purified by flash column chromatography on silica, eluting with 30% ethyl acetate/isohexane to obtain the title compound as a white solid (56 mg, 72%). $\delta_H$ (360 MHz, d$^6$ DMSO): 8.02 (1H, d, J=8.3 Hz), 7.95-7.59 (8H, m), 7.39 (2H, s), 7.33-7.27 (1H, m), 7.14 (1H, td, J=2.1, 8.5 Hz), 5.37 (2H, t, J=5.4 Hz), 1.07 (3H, d, J=5.9 Hz).

Example 65

[5-[(E)-2-(2,4-difluorophenyl)vinyl]-2-(phenylsulfonyl)benzyl]dimethylamine

A solution of 5-[(E)-2-(2,4-difluorophenyl)vinyl]-2-(phenylsulfonyl)benzaldehyde (prepared from Example 58 according to the method of Example 50 Step 1, 100 mg, 0.26 mmol), dimethylamine hydrochloride (50 mg, 0.62 mmol), titanium(IV) isopropoxide (0.2 mL, 0.62 mmol) and triethylamine (0.1 mL, 0.62 mmol) in ethanol (2 mL) was stirred at room temperature overnight. Sodium cyanoborohydride (35 mg, 0.56 mmol) was added and the reaction stirred for a further 3 hours. The solvent was removed in vacuo and the residue partitioned between water and ethyl acetate. The organic layer was washed with brine, dried over MgSO$_4$ and evaporated in vacuo. The residue was purified by flash column chromatography on silica, eluting with 0-3% methanol/dichloromethane, to give the title compound as a white solid. $\delta_H$ (360 MHz, d$^6$ DMSO): 8.12 (1H, d, J=8.2 Hz), 7.93-7.81 (5H, m), 7.68-7.56 (3H, m), 7.38 (2H, s), 7.33-7.27 (1H, m), 7.14 (1H, td, J=2.4, 8.5 Hz), 3.57 (2H, s), 1.88 (6H, s). m/z (ES$^+$) 414 [MH$^+$].

Example 66

2-bromo-1-[(E)-2-(2,4-difluorophenyl)vinyl]-4-(phenylsulfonyl)benzene

Prepared by analogy with Example 46. $\delta_H$ (360 MHz, CDCl$_3$): 8.14 (1H, d, J=1.8 Hz), 7.95 (2H, d, J=7.3 Hz), 7.84 (1H, dd, J=1.8, 8.4 Hz), 7.75 (1H, d, J=8.3 Hz), 7.63-7.51 (4H, m), 7.40 (1H, d, J=16.4 Hz), 7.19 (4H, d, J=16.3 Hz), 6.95-6.81 (2H, m).

Example 67

2-[(E)-2-(2,4-difluorophenyl)vinyl]-5-(phenylsulfonyl)benzonitrile

Prepared from Example 66 according to the method of Example 33. $\delta_H$ (360 MHz, CDCl$_3$): 8.19 (1H, d, J=1.8 Hz), 8.09 (1H, dd, J=1.9, 8.5 Hz), 7.97-7.89 (3H, m), 7.68-7.37 (6H, m), 6.96-6.82 (2H, m).

Example 68

3-({4-[(E)-2-(2,4-difluorophenyl)vinyl]phenyl}sulfonyl)benzamide

Prepared from Example 49 according to the method of Example 57. m/z (ES$^+$) 400 [MH$^+$].

Example 69

4-({4-[(E)-2-(2,4-difluorophenyl)vinyl]phenyl}sulfonyl)benzoic acid

Prepared by hydrolysis of 4-({4-[(E)-2-(2,4-difluorophenyl)vinyl]phenyl}sulfonyl)benzonitrile (Example 53) under the conditions of Example 48. $\delta_H$ (400 MHz, d$^6$ DMSO): 13.51 (1H, s), 8.15-8.08 (4H, m), 7.97 (2H, d, J=8.5 Hz), 7.91-7.86 (3H, m), 7.46-7.36 (2H, m), 7.34-7.29 (1H, m), 7.17 (1H, td, J=2.3, 8.5 Hz).

Examples 70-73

The following 4 examples were prepared according to the method of Example 50 starting from Example 47, using the appropriate amine in the last step:

| Example | NR$_2$ | m/z (ES$^+$) [MH$^+$] |
|---|---|---|
| 70 | pyrrolidinyl | 440 |
| 71 | NMe$_2$ | 414 |
| 72 | morpholinyl | 456 |
| 73 | 4-methylpiperazinyl | 469 |

Example 74

1-[3-({4-[(E)-2-(2,4-difluorophenyl)vinyl]phenyl}sulfonyl)benzyl]-4-(trifluoromethyl)piperidine To a solution of 3-({4-[E)-2-(2,4-difluorophenyl)vinyl]phenyl}sulfonyl)benzaldehyde (Example 50 Step 1, 100 mg, 0.26 mmol) and 4-(trifluoromethyl)piperidine (0.04 mL, 0.28 mmol) in tetrahydrofuran (1 mL) was added triacetoxyborohydride (83 mg, 0.39 mmol) in one portion and the reaction stirred overnight at room temperature. 4N sodium hydroxide was added and the products extracted into ethyl acetate. The combined organic layers were washed with saturated ammonium chloride solution and water, dried over Na$_2$SO$_4$ and concentrated in vacuo. The residue was purified by flash column chromatography on silica, eluting with 25% ethyl acetate/isohexane to yield the title compound as an oily solid which was treated with ethereal HCl to give the hydrochloride salt (96 mg, 66%). $\delta_H$ (400 MHz, d$^6$ DMSO): 8.26 (1H, s), 8.03-7.95 (3H, m), 7.89-7.83 (4H, m), 7.71 (1H, t, J=7.6 Hz), 7.44-7.28 (3H, m), 7.16 (1H, td, J=1.8, 8.3 Hz), 4.40 (2H, s), 3.43-3.38 (2H, m), 3.00-2.92 (1H, m), 2.67-2.60 (1H, m), 2.03-1.97 (2H, m), 1.86-1.80 (2H, m). m/z (ES$^+$) 522 [MH$^+$].

Example 75

4-[2-({4-[(E)-2-(4-fluorophenyl)vinyl]phenyl}sulfonyl)benzyl]morpholine

Step 1

2-Bromobenzaldehyde (1.55 g, 8.4 mmol), sodium 4-bromophenylsulfinate (2.79 g, 10 mmol) and copper(I) trifluoromethanesulfonate benzene complex (500 mg, 1 mmol)

were combined in dimethylsulfoxide (10 mL) under nitrogen and degassed. The suspension was heated to 110° C. and N,N-dimethylethylenediamine (176 mg, 2 mmol) was added. The reaction was heated until the colour became clear and pale yellow, then cooled and poured into water. The products were extracted into ethyl acetate. The organic layer was washed with water:brine (1:1, ×5), dried over MgSO$_4$ and evaporated in vacuo. The residue was triturated with isohexane to give 2-[(4-bromophenyl)sulfonyl]benzaldehyde (1.5 g, 55%). $\delta_H$ (400 MHz, CDCl$_3$): 10.76 (1H, s), 8.14-8.12 (1H, m), 7.98-7.96 (1H, m), 7.76-7.68 (4H, m), 7.64-7.62 (2H, m).

Step 2

2-[(4-Bromophenyl)sulfonyl]benzaldehyde (3 g, 9.23 mmol), bis(benzonitrile) dichloropalladium(II) (53 mg, 0.138 mmol), 1-ethenyl-4-fluorobenzene (1.6 g, 12.9 mmol), sodium acetate (1.52 g, 18.5 mmol) and N,N-dimethylglycine (28 mg, 0.277 mmol) were combined and degassed. 1-Methyl-2-pyrrolidinone (10 mL) was added while reagents were under nitrogen. The reaction was heated to 130° C. for 2 hours. The cooled reaction mixture was poured into water and extracted into ethyl acetate. The organic layer was washed with water:brine (1:1, ×5), dried over MgSO$_4$ and evaporated in vacuo. The residue was purified by flash column chromatography on silica, eluting with 25% ethyl acetate/isohexane, to give 2-({4-[E)-2-(4-fluorophenyl)vinyl]phenyl}sulfonyl) benzaldehyde (1.7 g, 50%). $\delta_H$ (500 MHz, CDCl$_3$): 10.89 (1H, s), 8.20 (1H, dd, J=1.3, 7.8 Hz), 8.03 (1H, dd, J=1.4, 7.4 Hz), 7.87 (2H, d, J=8.5 Hz), 7.79-7.72 (2H, m), 7.62 (2H, d, J=8.4 Hz), 7.52-7.48 (2H, m), 7.18 (1H, d, J=16.3 Hz), 7.08 (2H, t, J=8.6 Hz), 7.00 (1H, d, J=16.3 Hz).

Step 3

The title compound was prepared from 2-({4-[E)-2-(4-fluorophenyl)vinyl]phenyl}sulfonyl)benzaldehyde (Step 2) and morpholine according to the method of Example 74. m/z (ES$^+$) 438 [MH$^+$].

Examples 76-81

The following 6 examples were prepared according to the method of Example 75 using the appropriate amine in the last step:

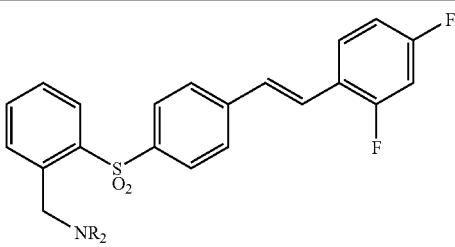

| Example | NR$_2$ | m/z (ES$^+$) [MH$^+$] |
|---|---|---|
| 76 | 4,4-difluoropiperidine | 472 |
| 77 | 3,3-difluoropiperidine | 472 |
| 78 | 4-methylpiperazine | 451 |
| 79 | 3-fluoropiperidine | 454 |
| 80 | 4-trifluoromethylpiperidine | 504 |
| 81 | 3-trifluoromethylpiperidine | 504 |

Example 83-98

The following 17 examples were prepared by analogy with Example 74:

| Example | Position | NR$_2$ | m/z (ES$^+$) [MH$^+$] |
|---|---|---|---|
| 82 | 3 | 4,4-difluoropiperidine | 490 |
| 83 | 3 | 4-trifluoromethyl-tetrahydropyridine | 520 |
| 84 | 3 | 3-fluoropyrrolidine | 458 |

-continued

| Example | Position | NR₂ | m/z (ES⁺) [MH⁺] |
|---|---|---|---|
| 85 | 3 | 2-(trifluoromethyl)pyrrolidin-1-yl | 508 |
| 86 | 3 | 3,3-difluoropyrrolidin-1-yl | 476 |
| 87 | 3 | thiomorpholine 1,1-dioxide | 504 |
| 88 | 3 | 3,3-difluoropiperidin-1-yl | 490 |
| 89 | 3 | 3-fluoropiperidin-1-yl | 472 |
| 90 | 3 | 3,3-difluoroazetidin-1-yl | 462 |
| 91 | 3 | 3-hydroxyazetidin-1-yl | 442 |
| 92 | 3 | (2-cyanoethyl)amino | 437 |
| 93 | 3 | 3-oxopiperazin-1-yl | 469 |
| 94 | 3 | 3-hydroxypyrrolidin-1-yl | 456 |
| 95 | 4 | morpholin-4-yl | 456 |
| 96 | 4 | 4-methylpiperazin-1-yl | 469 |
| 97 | 4 | 4-(trifluoromethyl)piperidin-1-yl | 522 |
| 98 | 4 | 4-(difluoromethyl)piperidin-1-yl | 490 |

In the case of the 4-substituted products (examples 95-98), the necessary aldehyde was prepared from Example 53 via the procedure of Example 50 Step 1.

Example 99

3-({4-[(Z)-2-(2,4-difluorophenyl)vinyl]phenyl}sulfonyl)benzonitrile

Prepared according to the method of Example 49; the mother liquors were purified by further successive recrystallisations (40% ethyl acetate/isohexane) and column chromatography (10-40% ethyl acetate/isohexane) to give the cis-isomer containing 10% trans-isomer. m/z (ES⁺) 382 [MH⁺].

Example 100

4-[3-({4-[(E)-2-phenylvinyl]phenyl}sulfonyl)benzyl]morpholine

Step 1

3-Iodobenzaldehyde (1.0 g, 4.3 mmol), copper(I) iodide (2.45 g, 12.9 mmol) and sodium 4-bromophenylsulfinate (1.55 g, 5.59 mmol) were combined in dimethylsulfoxide (8.6 mL) and heated to 110° C. for 4 hours. The cooled reaction mixture was diluted with ethyl acetate and filtered through Hyflo®. The filtrate was washed with water (×2) and brine and dried over MgSO₄. The solvent was removed in vacuo and the residue purified by flash column chromatography on silica, eluting with 25% ethyl acetate/isohexane, to give 3-[(4-bromophenyl)sulfonyl]benzaldehyde (0.5 g, 35%). $\delta_H$ (400 MHz, d⁶ DMSO): 10.09 (1H, s), 8.47-8.44 (1H, m), 8.29-8.25 (1H, m), 8.21 (1H, d, J=7.6 Hz), 7.96-7.94 (2H, m), 7.88-7.84 (3H, m).

Step 2

4-{3-[(4-Bromophenyl)sulfonyl]benzyl}morpholine was prepared from 3-[(4-bromophenyl)sulfonyl]benzaldehyde according to the method of Example 50 Step 2.

Step 3

The title compound was prepared from 4-{3-[(4-bromophenyl)sulfonyl]benzyl}morpholine and benzeneboronic acid according to the method of Example 1 Step 4. m/z (ES$^+$) 420 [MH$^+$].

Examples 101, 102

The following 2 examples were prepared according to the method of Example 100 using the appropriate boronic acid in Step 3:

| Example | R | m/z (ES$^+$) [MH$^+$] |
|---------|---|----------------------|
| 101 | F | 438 |
| 102 | Cl | 454 |

Example 103

2-[3-({4-[(E)-2-(2,4-difluorophenyl)vinyl]phenyl}sulfonyl)phenyl]pyridine

Butyllithium (1.6M in hexanes, 0.3 mL, 0.48 mmol) was added to a rapidly stirred solution of 2-bromopyridine (44 μL, 0.46 mmol) in tetrahydrofuran (1.2 mL) at −78° C. After 45 minutes, zinc chloride (1.0M in diethyl ether, 1.38 mL, 1.38 mmol) was added. The mixture was warmed to room temperature, tetrakis(triphenylphosphine)palladium(0) (27 mg) and 1-((E)-2-{4-[(3-bromophenyl)sulfonyl]phenyl}vinyl)-2,4-difluorobenzene (Example 109; 100 mg, 0.23 mmol) were added and the reaction heated to reflux overnight. The cooled reaction mixture was partitioned between ethyl acetate and 10% aqueous ethylenediaminetetraacetic acid, disodium salt. The organic layer was dried over Na$_2$SO$_4$ and concentrated in vacuo. The residue was purified by flash column chromatography on silica, eluting with 35% ethyl acetate/isohexane, to yield the title compound as a white solid (10 mg, 10%). δ$_H$ (400 MHz, CDCl$_3$): 8.69 (1H, d, J=4.7 Hz), 8.56 (1H, t, J=1.7 Hz), 8.23 (1H, d, J=7.8 Hz), 7.98-7.94 (3H, m), 7.80-7.74 (2H, m), 7.62-7.50 (4H, m), 7.29-7.23 (2H, m), 7.07 (1H, d, J=16.5 Hz), 6.90-6.80 (2H, m). m/z (ES$^+$) 434 [MH$^+$].

Example 104

3,3-difluoro-1-[2-({4-[(E)-2-(4-fluorophenyl)vinyl]phenyl}sulfonyl)benzyl]pyrrolidine Prepared by analogy with Example 75 using 3,3-difluoropyrrolidine in the last step. m/z (ES$^+$) 458[MH$^+$].

Example 105

(3R)-3-fluoro-1-[2-({4-[(E)-2-(4-fluorophenyl)vinyl]phenyl}sulfonyl)benzyl]pyrrolidine Prepared by analogy with Example 75 using (3R)-3-fluoropyrrolidine in the last step. m/z (ES$^+$) 440 [MH$^+$].

Example 106

3-fluoro-1-[2-({4-[(E)-2-(2,4-difluorophenyl)vinyl]phenyl}sulfonyl)benzyl]piperidine Prepared according to the methods of, sequentially, Example 75 Step 1, Example 74 using 3-fluoropiperidine and Example 1 Step 4.

Example 107

3-fluoro-1-[2-({4-[(E)-2-(2-fluorophenyl)vinyl]phenyl}sulfonyl)benzyl]piperidine 1-{2-[(4-Bromophenyl)sulfonyl]benzyl}-3-fluoropiperidine (prepared according to the methods of Example 75 Step 1 followed by Example 74 using 3-fluoropiperidine; 63 mg, 0.152 mmol), 2-fluorostyrene (36 μL, 0.3 mmol), sodium acetate (25 mg, 0.3 mmol) and palladium(I) chloride (1 mg) were combined in 1-methyl-2-pyrrolidinone (0.5 mL) and heated for 2 hours at 130° C. The cooled reaction mixture was partitioned between ethyl acetate and brine. The organic layer was washed further with brine, dried over Na$_2$SO$_4$ and concentrated in vacuo. The residue was purified by column chromatography on silica, eluting with 30% ethyl acetate/isohexane, to give the title compound. δ$_H$ (400 MHz, d$^6$ DMSO): 8.19 (1H, d, J=6.3 Hz), 8.00-7.97 (2H, m), 7.86-7.82 (2H, m), 7.77 (4H, s), 7.48-7.34 (3H, m), 7.23-7.19 (2H, m), 5.15 (1H, d, J=49 Hz), 4.72 (1H, d, J=13.4 Hz), 4.45-4.40 (1H, m), 3.79-3.73 (1H, m), 3.55-3.51 (1H, m), 3.45-3.32 (2H, m), 3.20-3.14 (1H, m), 1.99-1.93 (2H, m), 1.73 (1H, d, J=12.1 Hz). m/z (ES$^+$) 454 [MH$^+$].

Example 108

1-[2-({4-[(E)-2-(4-fluorophenyl)vinyl]phenyl}sulfonyl)benzyl]-2-(trifluoromethyl)pyrrolidine Prepared by analogy with Example 75 using 2-(trifluoromethyl)pyrrolidine in the last step. m/z (ES$^+$) 490 [MH$^+$].

Example 109

1-((E)-2-{4-[(3-bromophenyl)sulfonyl]phenyl}vinyl)-2,4-difluorobenzene

Prepared according to the method of Example 46 using 3-bromobenzenethiol in Step 1. δ$_H$ (400 MHz, d$^6$ DMSO): 8.12 (1H, t, J=1.8 Hz), 8.00-7.96 (3H, m), 7.91-7.83 (4H, m), 7.60-7.55 (1H, m), 7.44-7.34 (2H, m), 7.33-7.27 (1H, m), 7.15 (1H, td, J=2.6, 8.5 Hz).

Example 110

4-({4-[(E)-2-(2,4-difluorophenyl)vinyl]phenyl}sulfonyl)-N-methylbenzamide

To a solution of 4-({4-[(E)-2-(2,4-difluorophenyl)vinyl]phenyl}sulfonyl)benzoic acid (Example 69,40 mg, 0.1 mmol) in 1-methyl-2-pyrrolidinone (0.3 mL) was added 1,1'-carbonyldiimidazole (19.5 mg, 0.12 mmol). After stirring for 30 minutes, methylamine hydrochloride (8.1 mg, 0.12 mmol) was added and the reaction stirred for 4 hours. The mixture was partitioned between water and ethyl acetate. The organic layer was washed with brine, dried over MgSO$_4$ and concentrated in vacuo. The residue was purified by flash column chromatography on silica, eluting with 10% ethanol/ethyl acetate, to give the title compound. $\delta_H$ (500 MHz, d$^6$ DMSO): 8.63 (1H, d, J=4.5 Hz), 8.04-7.94 (6H, m), 7.88-7.82 (3H, m), 7.42-7.34 (2H, m), 7.32-7.26 (1H, m), 7.14 (1H, td, J=1.9, 8.4 Hz), 2.76 (3H, d, J=4.5 Hz); m/z (ES$^+$) 414 [MH$^+$].

Example 111

4-({4-[(E)-2-(2,4-difluorophenyl)vinyl]phenyl}sulfonyl)-N,N-dimethylbenzamide

Prepared according to the method of Example 110 using dimethylamine hydrochloride. m/z (ES$^+$) 428 [MH$^+$].

Example 112

2-fluoro-6-({4-[(E)-2-(4-fluorophenyl)vinyl]phenyl}sulfonyl)benzonitrile

Prepared according to the methods of, sequentially, Example 46 and Example 47 starting from 2-bromo-3-fluorobenzenethiol. $\delta_H$ (500 MHz, d$^6$ DMSO): 8.17 (1H, d, J=7.9 Hz), 8.09-8.03 (1H, m), 7.98 (2H, d, J=8.4 Hz), 7.90-7.86 (3H, m), 7.70-7.67 (2H, m), 7.49 (1H, d, J=16.4 Hz), 7.30 (1H, d, J=16.4 Hz), 7.23 (2H, t, J=8.8 Hz).

Example 113

1-(phenylethynyl)-4-(phenylsulfonyl)benzene

Step 1

Sodium phenylsulfinate (16.4 g, 0.1 mol) and 4-fluorobenzaldehyde (12.4 g, 0.1 mol) were combined in dimethylsulfoxide (100 mL) and heated at 120° C. for 4 days. The cooled reaction was poured into water. The resulting crystals were filtered off and washed with water, then dissolved in ethyl acetate/dichloromethane, dried and concentrated in vacuo until crystallisation ensued. The mixture was diluted with isohexane and the crystals filtered off and washed with further isohexane to yield 4-(phenylsulfonyl)benzaldehyde (19.6 g, 80%). $\delta_H$ (500 MHz, d$^6$ DMSO): 10.06 (1H, s), 8.16 (2H, d, J=8.3 Hz), 8.09 (2H, d, J=8.3 Hz), 7.99 (2H, d, J=7.7 Hz), 7.71 (1H, t, J=6.9 Hz), 7.63 (2H, t, J=7.7 Hz).

Step 2

To a mixture of 4-(phenylsulfonyl)benzaldehyde (8 g, 32.5 mmol) and potassium carbonate (8.97 g, 65 mmol) in methanol (400 mL) was added diethyl (1-diazo-2-oxopropyl)phosphonate (8.6 g, 39 mmol). The reaction was stirred at room temperature for 3 days then poured into water (600 mL) and extracted with ethyl acetate (×3). The combined organic layers were dried and evaporated. The residue was purified by flash column chromatography on silica, eluting with 5% ethyl acetate/isohexane, to give 1-ethynyl-4-(phenylsulfonyl)benzene (3.3 g, 42%). $\delta_H$ (500 MHz, CDCl$_3$): 7.94-7.88 (4H, m), 7.60-7.50 (5H, m), 3.23 (1H, s).

Step 3

A mixture of 1-ethynyl-4-(phenylsulfonyl)benzene (100 mg, 0.4 mmol), iodobenzene (0.05 mL, 0.44 mmol) and triethylamine (1 mL) in toluene (1 mL) was degassed. Copper(I) iodide (3 mg, 0.004 mmol) and dichlorobis(triphenylphosphine)-palladium(II) (3 mg, 0.004 mmol) were added and the reaction stirred at room temperature overnight. The mixture was poured into water and extracted with ethyl acetate. The organic layer was dried and concentrated in vacuo. The residue was purified by preparative HPLC to give the title compound (35 mg, 28%). $\delta_H$ (500 MHz, d$^6$ DMSO): 7.97 (4H, dd, J=2.6, 8.4 Hz), 7.77-7.69 (3H, m), 7.64-7.56 (4H, m), 7.43-7.41 (3H, m).

Examples 114-116

The following 3 examples were prepared according to the method of Example 113 using the appropriate iodobenzene derivative in Step 3:

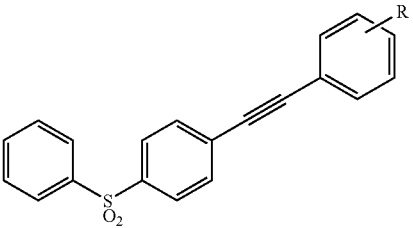

| Example | R | $\delta_H$ (500 MHz, CDCl$_3$) |
|---|---|---|
| 114 | 2-Cl | 7.96-7.92(4H, m), 7.67(2H, d, J=8.5Hz), 7.60-7.50 (4H, m), 7.44(1H, d, J=9.0Hz), 7.33-7.27(2H, m) |
| 115 | 3-Cl | 7.96-7.92(4H, m), 7.63-7.57(3H, m), 7.53-7.51 (3H, m), 7.41-7.39(1H, m), 7.36-7.34(1H, m), 7.29(1H, t, J=7.8Hz) |
| 116 | 4-Cl | 7.96-7.90(4H, m), 7.62-7.56(3H, m), 7.53-7.51(2H, m), 7.46-7.44(2H, m), 7.35-7.33(2H, m) |

Example 117

2,4-difluoro-1-{2-[4-(phenylsulfonyl)phenyl]ethyl}benzene 2,4-Difluoro-1-{(E)-2-[4-(phenylsulfonyl)phenyl]vinyl}benzene (Example 51, 57 mg, 0.16 mmol) and palladium (10% wt. on activated carbon, 20 mg) were combined in ethyl acetate (20 mL) and shaken in a Parr apparatus for 2 hours. The catalyst was removed by filtration and the filtrate evaporated in vacuo. The residue was purified by HPLC to yield the title compound as a white solid (23 mg, 40%). $\delta_H$ (400 z, CDCl$_3$): 7.93-7.91 (2H, m), 7.84-7.82 (2H, m), 7.56-7.46 (3H, m), 7.27-7.24 (2H, m), 7.00-6.94 (1H, m), 6.76-6.70 (2H, m), 2.92-2.84 (4H, m).

Example 118

2-(4-fluorophenyl)-1-[4-(phenylsulfonyl)phenyl]ethanol

Lithium chloride (0.57 g, 13.5 mmol, dried at 140° C. under vacuum) and copper(I) cyanide (0.605 g, 6.8 mmol)

were dissolved in tetrahydrofuran (5 mL) and cooled to −40° C. under nitrogen. 4-Fluorobenzylzinc chloride (0.5M in tetrahydrofuran, 15 mL) was added dropwise and the solution cooled to −20° C. for 5 minutes then to −78° C. Boron trifluoride diethyl etherate (1.7 mL, 13.5 mmol) and 4-(phenylsulfonyl)benzaldehyde (Example 113 Step 1, 300 mg, 1.2 mmol) in tetrahydrofuran (5 mL) were added and the reaction stirred at −78° C. for 30 minutes then warmed to 25° C. and quenched with saturated ammonium chloride solution. Ethyl acetate was added and the mixture stirred for 10 minutes then the layers separated. The organic layer was washed with brine, dried over MgSO$_4$ and evaporated. The residue was purified by flash column chromatography on silica, eluting with 40% ethyl acetate/isohexane, to give the title compound as a white solid (0.386 g, 90%). $\delta_H$ (360 MHz, CDCl$_3$): 7.94-7.88 (4H, m), 7.58-7.43 (5H, m), 7.10-7.02 (2H, m), 6.99-6.93 (2H, m), 4.92-4.88 (1H, m), 2.99-2.85 (2H, m), 2.01 (1H, d, J=3.2 Hz).

Example 119

1-fluoro-4-{2-fluoro-2-[4-(phenylsulfonyl)phenyl]ethyl}benzene 2-(4-Fluorophenyl)-1-[4-(phenylsulfonyl)phenyl]ethanol (Example 118, 100 mg, 0.28 mmol) was dissolved in dichloromethane (5 mL) and (diethylamino)sulfur trifluoride (0.05 mL, 0.32 mmol) added. The reaction was stirred at room temperature for 30 minutes. Saturated sodium hydrogencarbonate was added and the products extracted into ethyl acetate. The organic layer was dried over MgSO$_4$ and evaporated. The residue was triturated with diethyl ether/isohexane to give the title compound as a beige solid. $\delta_H$ (360 MHz, CDCl$_3$): 7.94-7.90 (4H, m), 7.58-7.48 (3H, m), 7.35 (2H, d, J=8.5 Hz), 7.08-7.00 (2H, m), 6.96-6.90 (2H, m), 5.69-5.53 (1H, m), 3.21-2.99 (2H, m).

Examples 120-126

The following 7 examples were prepared by analogy with Example 117:

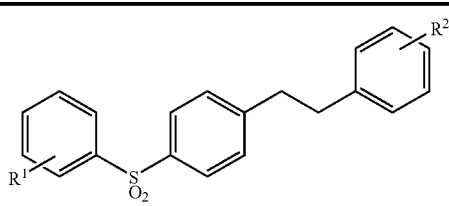

| Ex. | R$^1$ | R$^2$ | $\delta_H$ (400 MHz, d$^6$ DMSO) or m/z (ES$^+$) |
|---|---|---|---|
| 120 | H | 4-F | 7.93-7.91(2H, m), 7.84-7.82(2H, m), 7.57-7.47(3H, m), 7.26-7.23(2H, s), 7.05-7.01(2H, m), 6.95-6.89(2H, m), 2.95-2.83 (4H, m). (360 MHz, CDCl$_3$) |
| 121 | 3-F | 2,4-diF | 7.90-7.88(2H, m), 7.80-7.76(2H, m), 7.69-7.63(1H, m), 7.56-7.52(1H, m), 7.44(2H, d, J=8.4Hz), 7.32-7.26(1H, m), Ex7.15-7.09 (1H, m), 6.98-6.94(1H, m), 2.94-2.84 (4H, m) |
| 122 | 4-F | 2,4-diF | 8.02-7.98(2H, m), 7.86-7.83(2H, m), 7.47-7.41(4H, m), 7.32-7.26(1H, m), 7.15-7.11 (1H, m), 6.98-6.94 (1H, m), 2.93-2.85 (4H, m) |

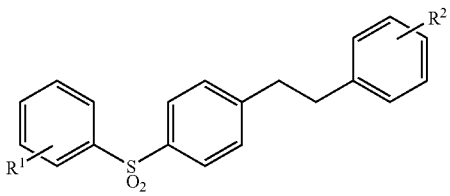

| Ex. | R$^1$ | R$^2$ | $\delta_H$ (400 MHz, d$^6$ DMSO) or m/z (ES$^+$) |
|---|---|---|---|
| 123 | 4-Me | 2,4-diF | 7.80(4H, t, J=8.2Hz), 7.41(4H, t, J=7.8Hz), 7.32-7.26(1H, m), 7.14-7.10(1H, m), 6.98-6.94(1H, m), 2.91-2.83(4H, m), 2.35(3H, s) |
| 124 | 2-F | 2,4-diF | 8.29-8.25(1H, m), 8.07(2H, d, J=7.0Hz), 8.03-7.99(1H, m), 7.73-7.69(3H, m), 7.66-7.62(1H, m), 7.56-7.50(1H, m), 7.39-7.33 (1H, m), 7.22-7.18(1H, m), 3.19-3.09 (4H, m) (400 MHz, d$^7$ DMF): |
| 125 | 2-CONH$_2$ | 2,4-diF | 385 [MH$^+$] |
| 126 | 2-CONH$_2$ | 2-F | 367 [MH$^+$] |

Example 127

4-({4-[2-(2,4-difluorophenyl)ethyl]phenyl}sulfonyl)benzonitrile 2,4-Difluoro-1-(2-{4-[(4-fluorophenyl)sulfonyl]phenyl}ethyl)benzene (Example 122, 20 mg, 0.053 mmol) was dissolved in dimethylsulfoxide (0.1 mL) and sodium cyanide (5.2 mg, 0.106 mmol) was added. The reaction was heated to 100° C. overnight. The cooled reaction mixture was partitioned between ethyl acetate and water. The organic layer was dried over Na$_2$SO$_4$ and evaporated in vacuo. The residue was purified by flash column chromatography on silica, eluting with 25% ethyl acetate/isohexane, to yield the title compound as a white solid (7 mg, 36%) $\delta_H$ (400 MHz, d$^6$ DMSO): 8.10-8.07 (4H, m), 7.89 (2H, d, J=8.4 Hz), 7.46 (2H, d, J=8.4 Hz), 7.29 (1H, q, J=7.6 Hz), 7.14-7.10 (1H, m), 6.98-6.94 (1H, m), 2.94-2.86 (4H, m).

Example 128

4-[3-({4-[2-(2,4-difluorophenyl)ethyl]phenyl}sulfonyl)benzyl]morpholine

Step 1

To a solution of [3-({4-[2-(2,4-difluorophenyl)ethyl]phenyl]sulfonyl)phenyl]methanol (prepared from 3-({4-[E)-2-(2,4-difluorophenyl)vinyl]phenyl}sulfonyl)benzaldehyde (Example 50 Step 1) according to the method of Example 117) in dichloromethane (4 mL) was added 4 Å molecular sieves (0.1 g) and the mixture stirred for 10 minutes. 4-Methylmorpholine N-oxide (68 mg, 0.58 mmol) was added in one portion and the reaction stirred for 10 minutes, then tetrapropylammonium perruthenate (6.9 mg, 0.02 mmol) added. The reaction was stirred for 30 minutes then diluted with ethyl acetate, filtered through a pad of silica and washed with further ethyl acetate. The filtrate was evaporated in vacuo. The residue was purified by flash column chromatography on silica, eluting with 25% ethyl acetate/isohexane, to yield 3-({4-[2-(2,4-difluorophenyl)ethyl]phenyl]sulfonyl)benzaldehyde (103 mg, 68%). $\delta_H$ (400 MHz, CDCl$_3$): 10.06 (1H, s), 8.40 (1H, s), 8.18 (1H, d, J=7.8 Hz), 8.07 (1H, d, J=7.6 Hz), 7.87 (2H, d, J=8.3 Hz), 7.69 (1H, t, J=7.7 Hz), 7.30

(2H, d, J=8.2 Hz), 6.99 (1H, q, J=7.9 Hz), 6.79-6.73 (2H, m), 2.95-2.87 (4H, m). m/z (ES$^+$) 387 [MH$^+$].

Step 2

The title compound was prepared from 3-({4-[2-(2,4-difluorophenyl)ethyl]phenyl}sulfonyl)benzaldehyde (Step 1) according to the method of Example 35 Step 2. m/z (ES$^+$) 458 [MH$^+$].

Example 129

1-[2-({4-[2-(2,4-difluorophenyl)ethyl]phenyl}sulfonyl)phenyl]-1H-imidazole 2,4-Difluoro-1-(2-{4-[(2-fluorophenyl)sulfonyl]phenyl}ethyl)benzene (Example 124, 100 mg, 0.26 mmol), potassium carbonate (126 mg, 0.39 mmol) and imidazole (26 mg, 0.39 mmol) were combined in dimethylsulfoxide (1.3 mL) and heated in a microwave reactor at 150° C. for 20 minutes. The reaction mixture was diluted with ethyl acetate, washed with water and brine, dried over Na$_2$SO$_4$ and evaporated in vacuo. The residue was purified by flash column chromatography on silica, eluting with 5% ethanol/ethyl acetate to yield the title compound as a white solid (85 mg, 77%). δ$_H$ (400 MHz, d$^6$ DMSO): 8.31-8.29 (1H, m), 7.87-7.79 (2H, m), 7.41-7.39 (2H, m), 7.31-7.23 (5H, m), 7.16-7.12 (1H, m), 6.99-6.95 (1H, m), 6.88 (1H, t, J=1.1 Hz), 6.85 (1H, t, J=1.3 Hz), 2.92-2.84 (4H, m). m/z (ES$^+$) 425 [MH$^+$].

Examples 130, 131

The following 2 examples were prepared according to the method of Example 129:

| Example | NR$_2$ | m/z (ES$^+$) [MH$^+$] |
|---|---|---|
| 130 |  | 428 |
| 131 |  | 414 |

Example 132

2-({4-[2-(2,4-difluorophenyl)-2-oxoethyl]phenyl}sulfonyl)benzonitrile

A mixture of 2-[(4-bromophenyl)sulfonyl]benzonitrile (prepared according to the methods of Example 1 Step 1 using 2-cyanobenzenethiol followed by Example 16 Step 1; 0.32 g, 0.993 mmol), 2',4'-difluoroacetophenone (0.31 g, 1.99 mmol), potassium phosphate (0.48 g, 2.26 mmol), tris(dibenzylideneacetone)dipalladium(0) (9 mg, 0.0098 mmol) and 4,5-bis(diphenylphosphino)-9,9-dimethylxanthene (13 mg, 0.022 mmol) in tetrahydrofuran (1 mL) was degassed then heated at 80° C. under nitrogen for 14 hours. Saturated ammonium chloride solution was added and the products extracted into ethyl acetate. The organic layer was dried over MgSO$_4$ and concentrated in vacuo while loading onto silica. Dry flash column chromatography eluting with 25-40% ethyl acetate/isohexane followed by recrystallisation from ethanol gave the title compound as a beige solid (0.22 g, 56%). δ$_H$ (500 MHz, CDCl$_3$): 8.33 (1H, d, J=8.0 Hz), 8.05 (2H, d, J=8.3 Hz), 7.95-7.89 (1H, m), 7.83-7.77 (2H, m), 7.70-7.68 (1H, m), 7.43 (2H, d, J=8.3 Hz), 7.00-6.96 (1H, m), 6.92-6.88 (1H, m), 4.33 (2H, d, J=2.7 Hz).

Example 133

2-({4-[2-(2,4-difluorophenyl)-2-hydroxyethyl]phenyl}sulfonyl)benzonitrile

Prepared from Example 132 according to the method of Example 41. δ$_H$ (500 MHz, d$^6$ DMSO): 8.29 (1H, d, J=7.9 Hz), 8.10 (1H, d, J=7.6 Hz), 7.99 (1H, t, J=7.8 Hz), 7.90-7.86 (3H, m), 7.48-7.42 (3H, m), 7.11-7.07 (1H, m), 7.02 (1H, td, J=2.2, 8.5 Hz), 5.55 (1H, d, J=4.9 Hz), 5.00 (1H, q, J=5.8 Hz), 2.97 (2H, d, J=6.3 Hz).

Example 134

2-({4-[2-(2,4-difluorophenyl)-2-fluoroethyl]phenyl}sulfonyl)benzonitrile

Prepared from Example 133 according to the method of Example 119. δ$_H$ (500, d$^6$ DMSO): 8.31 (1H, d, J=8.0 Hz), 8.10 (1H, d, J=7.6 Hz), 7.99 (1H, t, J=7.8 Hz), 7.93-7.87 (3H, m), 7.56-7.50 (3H, m), 7.26 (1H, t, J=9.2 Hz), 7.11 (1H, t, J=8.5 Hz), 6.03-5.91 (1H, m), 3.47-3.23 (2H, m).

Example 135

(1S)-1-[2-({4-[(E)-2-(4-fluorophenyl)vinyl]phenyl}sulfonyl)phenyl]ethanol

Step 1

To each of three identical Emrys microwave reaction vessels was added (S)-1-(2-bromophenyl)ethanol (1.67 g, 8.3 mmol), CuI (189 mg, 1.0 mmol), 1,4-dioxane (12.4 ml), N,N'-dimethylethylenediamine (0.18 ml, 1.7 mmol) and sodium iodide dihydrate (3.1 g, 16.6 mmol). Each vessel was sealed and heated in an Emrys microwave reactor to 150° C. for 2 h. On cooling, the mixtures were combined and partitioned between water (20 ml) and EtOAc (20 ml). The organic phase was washed with brine (20 ml), dried (MgSO$_4$), filtered, and concentrated in vacuo. The crude product was taken up in isohexane (50 ml) and the solution held at –15° C. for 16 h to afford (S)-1-(2-iodophenyl)ethanol as a white crystalline solid (4.95 g).

Step 2

A suspension of (S)-1-(2-iodophenyl)ethanol (Step 1; 4.4 g, 17.7 mmol), Intermediate 1 (5.54 g, 19.5 mmol), CuI (10.1 g, 53.0 mmol) and DMSO (80 ml) was degassed by repeated evacuation and release to N$_2$, then heated in an oil bath at 110° C. for 75 minutes. The cooled mixture was partitioned between concentrated ammonium hydroxide solution (100 ml) and EtOAc (100 ml), and the aqueous phase extracted with further EtOAc (50 ml). The combined organics were washed with water (2×100 ml) and brine (100 ml), dried (MgSO$_4$), filtered, and concentrated in vacuo. The crude product was purified by flash chromatography on silica (eluant 25 to 35 to 45% EtOAc/isohexane) and then again with 5% Et$_2$O/CH$_2$Cl$_2$. The resulting foam was stirred with pentane for 1 h to afford the pure product as a white amorphous solid (3.97 g). The material was recrystallised from a circa 90% MeOH/water mixture to afford colourless crystals; m.p. 75° C. δ$_H$ (500 MHz, d$^6$ DMSO): 8.02 (1H, d, J 7.3), 7.81-7.78 (5H, m), 7.73-7.67 (3H, m), 7.52 (1H, t, J 7.2), 7.43 (1H, d, J 16.5), 7.29 (1H, d, J 16.4), 7.22 (2H, t, J 8.8), 5.44-5.40 (1H, m), 5.28 (1H, d, J 4.0), 1.09 (3H, d, J 6.2); m/z (ES$^+$) 365 [(M-OH)$^+$].

Example 136

(1S)-1-[2-({4-[(E)-2-(2,4-difluorophenyl)vinyl]phenyl}sulfonyl)phenyl]ethanol

Prepared as described in Example 135, substituting Intermediate 2 for Intermediate 1 in Step 2.

δ$_H$ (500 MHz, d$^6$ DMSO): 8.03 (1H, d, J 7.9), 7.90-7.80 (6H, m), 7.72 (1H, t, J 7.4), 7.53 (1H, t, J 7.7), 7.40 (2H, q, J 12.7), 7.34-7.28 (1H, m), 7.16 (1H, t, J 8.5), 5.43-5.39 (1H, m), 5.30 (1H, d, J 4.0), 1.09 (3H, d, J 6.2). m/z (ES$^+$) 383 [(M-OH$^+$)]

Example 137

2-({4-[(E)-2-(2,4-difluorophenyl)vinyl]phenyl}sulfonyl)-3-methylbenzamide

Prepared from 2-bromo-3-methylbenzamide by the procedure of Example 135 using Intermediate 2 in Step 2. m/z (ES$^+$) 397 [(M-NH$_2$)$^+$].

Example 138

(1S)-1-[2-({4-[(E)-2-(4-fluorophenyl)vinyl]-3-methylphenyl}sulfonyl)phenyl]ethanol Step 1

4-Bromo-3-methylbenzenesulfonyl chloride (1.145 g, 4.25 mmol) was added portion wise to a solution of sodium sulfite (0.578 g, 2.29 mmol) and sodium hydrogen carbonate (0.749 g, 2.4 mmol) in water (10 mL) at 80° C. The reaction was heated to 90° C. for 3 h. The cooled reaction mixture was evaporated in vacuo to half-volume, at which point a precipitate appeared. This was removed by filtration. The filtrate was concentrated further then cooled to 5° C. and the precipitate removed by filtration. The combined residues were washed with water and dried to give sodium 4-bromo-3-methylbenzenesulfinate (0.54 g).

Step 2

(1S)-1-[2-({4-bromo-3-methylphenyl}sulfonyl)phenyl]ethanol was prepared as described in Example 135 Step 2 using sodium 4-bromo-3-methylbenzenesulfinate in place of Intermediate 1.

Step 3

An Emrys microwave vial containing (1S)-1-[2-({4-bromo-3-methylphenyl}sulfonyl)phenyl]ethanol (71 mg, 0.2 mmol), [(E)-2-(4-fluorophenyl)vinyl]boronic acid (43 mg, 0.26 mmol), tetrakis(triphenylphosphine) palladium (0) (23 mg, 0.020 mmol), THF (2 mL) and 2M aqueous sodium carbonate (1 mL) was heated in an Emrys microwave reactor at 150° C. for 10 minutes. On cooling, the mixture was partitioned between EtOAc (15 mL) and water (15 mL) and the organic phase was washed with brine, dried (MgSO$_4$), filtered and concentrated in vacuo. The crude material was purified by flash chromatography on silica (eluant 30% EtOAc/isohexane) to afford the title compound as a white solid (45 mg). δ$_H$ (500 MHz, d$^6$ DMSO): 8.01 (1H, d, J 7.9), 7.88 (1H, d, J 8.2), 7.80 (1H, d, J 7.8), 7.73-7.63 (5H, m), 7.52 (1H, t, J 7.6), 7.37 (1H, d, J 16.3), 7.29 (1H, d, J 16.2), 7.22 (2H, t, J 8.7), 5.45 (1H, s), 5.30 (1H, s), 2.46 (3H, s), 1.11 (3H, d, J 5.9). m/z (ES$^+$) 379 [(M-OH)$^+$].

Example 139

[2-({4-[(E)-2-(2,4-difluorophenyl)vinyl]phenyl}sulfonyl)phenyl]methanol

Step 1

2-({4-[(E)-2-(2,4-difluorophenyl)vinyl]phenyl}sulfonyl)benzaldehyde was prepared according to the method of Example 135, Step 2 using 2-iodobenzaldehyde in place of (S)-1-(2-iodophenyl)ethanol and Intermediate 2 in place of Intermediate 1.

Step 2

Sodium borohydride (89 mg, 1.8 mmol) was added to a solution of 2-({4-[(E)-2-(2,4-difluorophenyl)vinyl]phenyl}sulfonyl)benzaldehyde (Step 1; 233 mg, 0.61 mmol) in MeOH (7 mL) and CH$_2$Cl$_2$ (3 mL). After 2 h, the mixture was partitioned between CH$_2$Cl$_2$ (10 mL) and water (10 mL), the phases were separated and the aqueous portion extracted with further CH$_2$Cl$_2$ (10 mL). The combined organics were then dried (MgSO$_4$), filtered and concentrated in vacuo. Purification by flash chromatography (eluant 40% EtOAc/isohexane) gave the title compound as a white solid (208 mg). δ$_H$ (500 MHz, d$^6$ DMSO): 8.08 (1H, d, J 7.7), 7.89-7.83 (5H, m), 7.77 (1H, d, J 7.6), 7.72 (1H, t, J 7.4), 7.55 (1H, t, J 7.5), 7.42-7.34 (2H, m), 7.33-7.27 (1H, m), 7.15 (1H, td, J 2.1, 8.4), 5.39 (1H, t, J 5.7), 4.69 (2H, d, J 5.7). m/z (ES$^+$) 369 [(M-OH)$^+$].

Example 140

[2-({4-[(E)-2-(4-fluorophenyl)vinyl]phenyl}sulfonyl)phenyl]methanol

Prepared according to the method of Example 139 using Intermediate 1 in place of Intermediate 2. δ$_H$ (400, d$^6$ DMSO): 8.10 (1H, dd, J 1.0, 7.8), 7.86-7.68 (8H, m), 7.57-7.55 (1H, m), 7.44 (1H, d, J 16.5), 7.32-7.22 (3H, m), 5.41 (1H, t, J 5.7), 4.72 (2H, d, J 5.7). m/z (ES$^+$) 351 [(M-OH)$^+$].

Example 141

2-[2-({4-[(E)-2-(4-fluorophenyl)vinyl]phenyl}sulfonyl)phenyl]ethanone (1S)-1-[2-({4-[(E)-2-(4-fluorophenyl)vinyl]phenyl}sulfonyl)phenyl]ethanol (Example 135; 100 mg, 0.26 mmol), N-methylmorpholine-N-oxide (46 mg, 0.39 mmol), 4 Å activated molecular sieves (100 mg) and CH$_2$Cl$_2$ (2.6 mL) were combined under N$_2$ and stirred for 20 minutes prior to addition of tetra(n-propyl)ammonium perruthenate (4.6 mg, 0.013 mmol). After a further 20 minutes, the mixture purified by flash chromatography (eluant 40% EtOAc/isohexane) to afford 1-[2-({4-[(E)-2-(4-fluorophenyl)vinyl]phenyl}sulfonyl)phenyl]ethanone as a white solid (84 mg). δ$_H$ (400 MHz, d$^6$ DMSO): 8.10 (1H, d, J 7.8), 7.88 (2H, d, J 8.5), 7.80 (3H, dd, J 0.0, 8.7), 7.72-7.68 (3H, m), 7.62 (1H, d, J 6.6), 7.46 (1H, d, J 16.5), 7.32-7.22 (3H, m), 2.61 (3H, s). m/z (ES$^+$) 380 [MH$^+$].

Example 142

2-[2-({4-[(E)-2-(4-fluorophenyl)vinyl]phenyl}sulfonyl)phenyl]propan-2-ol

A stirred THF (1 mL) solution of 1-[2-({4-[(E)-2-(2,4-difluorophenyl)vinyl]phenyl}sulfonyl)phenyl]ethanone (Example 141; 65 mg, 0.17 mmol) was treated with methyl magnesium bromide (3 N in Et$_2$O; 0.17 mL, 0.51 mmol) at ambient temperature. After 75 minutes, the mixture was partitioned between water (20 mL) and EtOAc (20 mL). The phases were separated and the organic phase dried (MgSO$_4$), filtered and concentrated in vacuo. The crude material was purified by flash chromatography on silica (eluant 35% EtOAc/isohexane). The material thus obtained was washed with hexane to afford the title compound as a white solid (53 mg). $\delta_H$ (500 MHz, d$^6$ DMSO): 8.25 (1H, d, J 8.1), 7.71-7.64 (8H, m), 7.53 (1H, t, J 6.1), 7.40 (1H, d, J 16.4), 7.30-7.22 (3H, m), 4.98 (1H, s), 1.56 (6H, s). m/z (ES$^+$) 419 [(M+Na)$^+$].

Example 143

2-[2-({4-[(E)-2-(4-fluorophenyl)vinyl]phenyl}sulfonyl)phenyl]ethanol

Step 1

In each of two identical vessels, a mixture of 2-(2-bromophenyl)ethanol (750 mg, 3.7 mmol), sodium iodide dihydrate (1.39 g, 7.5 mmol), CuI (71.0 mg, 0.37 mmol) and N,N'-dimethylethylenediamine (79.4 μL, 65.8 mg, 0.75 mmol) in 1,4-dioxane (8 mL) was heated to 150° C. in a microwave reactor for 4 h. The two reaction mixtures were combined, diluted with water (90 mL) and concentrated ammonium hydroxide (20 mL), then extracted with EtOAc (3×50 mL). The combined organic layers were washed with water (50 mL) then brine (50 mL), dried (MgSO$_4$) and concentrated in vacuo. The resulting pale yellow oil (1.62 g) was found to be a 3:1 mixture of 2-(2-iodophenyl)ethanol:2-(2-bromophenyl)ethanol and was used without further purification. Data for major compound: $\delta_H$ (360 MHz, CDCl$_3$): 7.84 (1H, d, J 8.2), 7.32-7.24 (2H, m), 6.94-6.86 (1H, m), 3.87 (2H, br s), 3.02 (2H, t, J 7.0), 1.43 (1H, s).

Step 2

The 3:1 mixture of 2-(2-iodophenyl)ethanol:2-(2-bromophenyl)ethanol (Step 1; 200 mg) was reacted with Intermediate 1 (275 mg, 0.97 mmol) and CuI (461 mg, 2.4 mmol) in DMSO (5 mL) by the procedure of Example 135 Step 2. The crude product was purified by flash chromatography on silica (eluant 25% then 40% EtOAc/isohexane) yielding the title compound as a white solid (65 mg): $\delta_H$ (400 MHz, CDCl$_3$): 8.16 (1H, d, J 8.0), 7.84 (2H, d, J 8.4), 7.61-7.37 (7H, m), 7.17 (1H, d, J 16.3), 7.07 (2H, t, J 8.6), 7.00 (1H, d, J 16.3), 3.83 (2H, q, J 6.2), 3.14 (2H, t, J 6.5), 1.99 (1H, t, J 5.7). m/z (ES$^+$) 365 [(M-OH)$^+$].

Example 144

Methyl 2-({4-[(E)-2-(2,4-difluorophenyl)vinyl]phenyl}sulfonyl)benzoate

Step 1

Methyl 2-[(4-bromophenyl)sulfonyl]benzoate was prepared according to the method of Example 135, Step 2 using methyl 2-bromobenzoate (2.8 mL, 20 mmol) in place of (S)-1-(2-iodophenyl)ethanol and sodium 4-bromophenylsulfinate dihydrate (5.6 g, 20 mmol) in place of Intermediate 1, together with CuI (19 g, 100 mmol) and DMSO (40 mL), affording product as a white solid (3.8 g).

Step 2

1-Ethynyl-2,4-difluorobenzene (9.6 g, 69.5 mmol) was warmed to 40° C. and catechol borane (8.3 g, 69.2 mmol) was added. The dark reaction mixture was stirred at 40° C. for 3 h before stirring at 80° C. for 24 h. Room temperature was attained and the mixture left to stand for 2 days. Water was added and the resulting dark solid collected by filtration. The solid was washed on the sinter with toluene to leave a beige solid, identified as [(E)-2-(2,4-difluorophenyl)vinyl]boronic acid and a mixture of anhydrides (3.8 g).

Step 3

The title compound was prepared according to the method described in Example 138, Step 3 using methyl 2-[(4-bromophenyl)sulfonyl]benzoate (Step 1) in place of (1S)-1-[2-({4-bromo-3-methylphenyl}sulfonyl)phenyl]ethanol and [(E)-2-(2,4-difluorophenyl)vinyl]boronic acid (Step 2) in place of [(E)-2-(4-fluorophenyl)vinyl]boronic acid. $\delta_H$ (500 MHz, d$^6$ DMSO): 8.22-8.20 (1H, m), 7.94-7.80 (7H, m), 7.69-7.63 (1H, m), 7.44 (1H, d, J 16.4), 7.39 (1H, d, J 16.4), 7.35-7.30 (1H, m), 7.19-7.15 (1H, m), 3.87 (3H, s). m/z (ES$^+$) 383 [(M-MeO)$^+$].

Example 145

Methyl 2-({4-[(E)-2-(4-fluorophenyl)vinyl]phenyl}sulfonyl)benzoate

A suspension of the methyl 2-iodobenzoate (8.8 mL, 60 mmol), Intermediate 1 (20.4 g, 72 mmol) and CuI (17.1 g, 90 mmol) in DMSO (300 ml) was degassed by repeated evacuation and release to N$_2$, then heated in an oil bath at 100° C. for 4 h. The cooled mixture was partitioned between water (1 L) and EtOAc (600 mL) and the dense suspension stirred for 10 minutes before being filtered through a plug of Hyflo®. The residue was extracted with EtOAc (400 mL) and the filtrate transferred to a separating funnel containing aqueous ammonium hydroxide solution (200 mL). The phases were separated and the aqueous phase extracted with EtOAc (twice). The combined organic fractions were washed with water, then brine, dried (MgSO$_4$), filtered and concentrated in vacuo. The crude product loaded onto silica and purified by flash chromatography (eluant 1% Et$_2$O/CH$_2$Cl$_2$) and the resulting material recrystallised from 50% EtOAc/hexane to afford the title compound as colourless crystals (13.9 g); m.p. 125° C. $\delta_H$ (500 MHz, d$^6$ DMSO): 8.22-8.20 (1H, m), 7.93 (2H, d, J 8.5), 7.84-7.78 (4H, m), 7.72-7.66 (3H, m), 7.46 (1H, d, J 16.4), 7.30 (1H, d, J 16.4) 7.27-7.21 (2H, m), 3.86 (3H, s). m/z (ES$^+$) 365 [(M-MeO)$^+$].

Example 146

Methyl 3-({4-[(E)-2-(4-fluorophenyl)vinyl]phenyl}sulfonyl)benzoate

Prepared according to the method of Example 144, Step 1 using methyl 3-bromobenzoate, in place of methyl 2-bromobenzoate, and Intermediate 1 in place of sodium 4-bromophenylsulfinate dihydrate. $\delta_H$ (500 MHz, d$^6$ DMSO): 8.42 (1H, s), 8.25 (2H, dd, J 8.0, 12.9), 7.98 (2H, t, J 8.0), 7.83-7.79 (3H, m), 7.70 (2H, dd, J 5.7, 8.7), 7.45 (1H, d, J 16.4), 7.31-7.23 (3H, m), 3.90 (3H, s). m/z (ES$^+$) 397 [MH$^+$].

Example 147

Methyl 2-({4-[(E)-2-(4-fluorophenyl)vinyl]phenyl}sulfonyl)-3-methylbenzoate

Prepared according to the method of Example 145 using methyl 2-iodo-3-methylbenzoate in place of methyl 2-iodobenzoate. $\delta_H$ (400 MHz, $d^6$ DMSO): 7.95 (2H, d, J 8.5), 7.85 (2H, d, J 8.6), 7.71-7.67 (3H, m), 7.48 (3H, dd, J 6.7, 12.9), 7.31 (1H, d, J 16.5), 7.25 (2H, t, J 8.9), 3.89 (3H, s), 2.43 (3H, s). m/z (ES$^+$) 433 [(M+Na)$^+$].

Example 148

2-[2-({4-[(E)-2-(2,4-difluorophenyl)vinyl]phenyl}sulfonyl)phenyl]-1H-imidazole

Step 1

2-(2-bromophenyl)-1H-imidazole (WO 9407486; 1.0 g, 4.48 mmol) was dissolved in THF (11 mL) and DMF (11 mL) and cooled to 0° C. Sodium hydride (60% dispersion in mineral oil, 197 mg, 4.93 mol) was added and the reaction stirred for 20 minutes. 2-(Trimethylsilyl)ethoxymethyl chloride (0.79 mL, 4.93 mmol) was added and the reaction stirred overnight at room temperature. The reaction was quenched with MeOH then partitioned between water and Et$_2$O. The organic layer was dried (MgSO$_4$) and concentrated in vacuo and the residue was purified by flash column chromatography to afford 2-(2-bromophenyl)-1-{[2-(trimethylsilyl)ethoxy]methyl}-1H-imidazole as an off-white solid (1.5 g).

Step 2

2-[2-({4-[(E)-2-(2,4-Difluorophenyl)vinyl]phenyl}sulfonyl)phenyl]-1-({[2-(trimethylsilyl)ethoxy]methyl}-1H-imidazole was prepared according to the method of Example 135 Step 2 using 2-(2-bromophenyl)-1-{[2-(trimethylsilyl)ethoxy]methyl}-1H-imidazole (Step 1) in place of (S)-1-(2-iodophenyl)ethanol and Intermediate 2 in place of Intermediate 1.

Step 3

A solution of 2-[2-({4-[(E)-2-(2,4-difluorophenyl)vinyl]phenyl}sulfonyl)phenyl]-1-{[2-(trimethylsilyl)ethoxy]methyl}-1H-imidazole (Step 2, 110 mg) in CH$_2$Cl$_2$ (5 mL) was treated with trifluoroacetic acid (5 mL) and the solution stirred for 16 h, then concentrated in vacuo and partitioned between saturated aqueous NaHCO$_3$ (20 mL) and EtOAc (20 mL). The phases were separated and the organic phase dried (MgSO$_4$), filtered and concentrated in vacuo. The residue was purified by flash chromatography on silica (eluant 75% EtOAc/isohexane) to afford a colourless oil, which solidified on treatment with Et$_2$O. The solid was washed with 50% EtOAc/isohexane and dried, to afford the title compound as a white solid (47 mg). $\delta_H$ (500 MHz, $d^6$ DMSO): 12.11 (1H, s), 8.25 (1H, t, J 4.6), 7.85 (1H, q, J 8.1), 7.77-7.71 (2H, m), 7.69 (2H, d, J 8.4), 7.58 (2H, d, J 8.4), 7.51 (1H, t, J 4.4), 7.39-7.29 (3H, m), 7.23 (1H, s), 7.15 (1H, td, J 2.5, 8.5), 6.94 (1H, s); m/z (ES$^+$) 422 [MH$^+$].

Example 149

2-[2-({4-[(E)-2-(4-fluorophenyl)vinyl]phenyl}sulfonyl)phenyl]-1H-imidazole

Prepared according to the method of Example 145 using 2-(2-bromophenyl)-1H-imidazole (WO 9407486; 1.0 g, 4.48 mmol) in place of methyl 2-iodobenzoate. $\delta_H$ (500 MHz, CDCl$_3$): 11.08 (1H, s), 8.35 (1H, d, J 8.0), 8.02 (1H, d, J 7.7), 7.69-7.67 (1H, m), 7.60 (1H, t, J 7.7), 7.46-7.38 (6H, m), 7.18 (1H, s), 7.10-7.03 (4H, m), 6.89 (1H, d, J 16.3). m/z (ES$^+$) 405 [MH$^+$].

Example 150

2-[2-({4-[(E)-2-(2,4-difluorophenyl)vinyl]phenyl}sulfonyl)phenyl]-1,3,4-oxadiazole Step 1

Methyl 2-[(4-bromophenyl)sulfonyl]benzoate (Example 144 Step 1; 150 mg, 0.46 mmol) and hydrazine hydrate (0.06 mL, 2.32 mmol) were stirred together at room temperature for 1.5 h then at 90° C. for 2 h. The excess hydrazine was removed in vacuo and the residue was dissolved in triethylorthoformate (4.6 mL) with catalytic camphorsulfonic acid and the mixture heated at 90° C. overnight. The cooled reaction mixture was partitioned between EtOAc and water and the organic layer was washed with brine and evaporated in vacuo. The residue was purified by flash column chromatography on silica (eluant 50% EtOAc/isohexane) to yield 2-{2-[(4-bromophenyl)sulfonyl]phenyl}-1,3,4-oxadiazole (60 mg, 35%). $\delta_H$ (400 MHz, $d^6$ DMSO): 9.42 (1H, s), 8.35-8.33 (1H, m), 7.97-7.91 (2H, m), 7.86-7.84 (3H, m), 7.80-7.78 (2H, m).

Step 2

The title compound was prepared according to the method of preparation of Intermediate 1, Step 2, using 2-{2-[(4-bromophenyl)sulfonyl]phenyl}-1,3,4-oxadiazole (Step 1) in place of 3-[(4-bromophenyl)sulfonyl]propanenitrile and 2,4-difluorostyrene in place of 4-fluorostyrene. $\delta_H$ (500 MHz, $d^6$ DMSO): 9.45 (1H, s), 8.35 (1H, d, J 7.8), 7.97-7.85 (8H, m), 7.47-7.31 (3H, m), 7.17 (1H, t, J 8.6). m/z (ES$^+$) 425 [MH$^+$].

Example 151

2-[2-({4-[(E)-2-(4-fluorophenyl)vinyl]phenyl}sulfonyl)phenyl]-1,3,4-oxadiazole

Prepared from methyl 2-({4-[(E)-2-(4-fluorophenyl)vinyl]phenyl}sulfonyl)benzoate (Example 145) according to the method of Example 150 Step 1. $\delta_H$ (400 MHz, $d^6$ DMSO): 9.48 (1H, s), 8.36 (1H, dd, J 1.3, 8.0), 8.00-7.82 (7H, m), 7.74-7.70 (2H, m), 7.49 (1H, d, J 16.5), 7.34-7.24 (3H, m); m/z (ES$^+$) 407 [MH$^+$].

Examples 152-161

The following were prepared by methods analogous to those of Examples 148 and 149:

| Example | R$^1$ | Z | m/z (ES$^+$) [MH$^+$] |
|---|---|---|---|
| 152 | H | thiazol-2-yl | 422 |
| 153 | H | 1-Me-imidazol-2-yl | 437 |

-continued

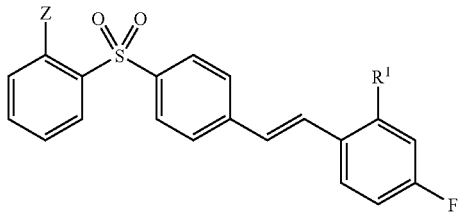

| Example | R¹ | Z | m/z (ES⁺) [MH⁺] |
|---|---|---|---|
| 154 | H | pyrazol-3-yl | 405 |
| 155 | F | pyrazol-3-yl | 423 |
| 156 | F | 1,2,4-triazol-3-yl | 424 |
| 157 | H | 1,2,4-triazol-3-yl | 406 |
| 158 | F | oxazol-2-yl | 424 |
| 159 | F | 1,2,3-triazol-4-yl | 424 |
| 160 | F | 2-pyridyl | 434 |
| 161 | H | 3-pyridyl | 416 |

Example 162

1-({4-[(E)-2-(4-fluorophenyl)vinyl]phenyl}sulfonyl)-2-(methylsulfinyl)benzene

Step 1
2-Iodothioanisole was reacted with sodium 4-bromophhenylsulfinate by the procedure of Example 100 Step 1.

Step 2
The thioether from Step 1 was oxidised to the corresponding sulfoxide by the procedure of Example 16 Step 1.

Step 3
The product of Step 2 was coupled with 4-fluorostyrene by the procedure of Example 107 to give the title compound. $\delta_H$ (500 MHz, d⁶ DMSO): 8.16 (2H, dd, J=7.8, 15.3 Hz), 7.99 (1H, t, J=7.4 Hz), 7.94 (2H, d, J=8.4 Hz), 7.84-7.81 (3H, m), 7.68 (2H, dd, J=5.8, 8.3 Hz), 7.44 (1H, d, J=16.5 Hz), 7.28 (1H, d, J=16.5 Hz), 7.22 (2H, t, J=8.7 Hz), 2.85 (3H, s).

Example 163

1-(2,4-difluorophenyl)-2-(4-{[2-(hydroxymethyl)phenyl]sulfonyl}phenyl)ethanone

2-Fluorobenzaldehyde was reacted with sodium 4-bromophhenylsulfinate by the procedure of Example 113 Step 1, then the aldehyde group reduced using sodium borohydride by the procedure of Example 41. The resulting bromophenylsulfonylbenzyl alcohol was reacted with 2',4'-difluoroacetophenone as described in Example 132 to provide the title compound. $\delta_H$ (500 MHz, d⁶ DMSO): 8.07 (1H, d, J=7.8 Hz), 7.96 (1H, q, J=8.0 Hz), 7.82-7.77 (3H, m), 7.72 (1H, t, J=7.5 Hz), 7.54 (1H, t, J=7.5 Hz), 7.48 (2H, d, J=8.2 Hz), 7.45-7.41 (1H, m), 7.23 (1H, td, J=2.2, 7.7 Hz), 5.41 (1H, t, J=5.7 Hz), 4.69 (2H, d, J=5.7 Hz), 4.45 (2H, s).

Example 164

2-({4-[(E)-2-(4-fluorophenyl)vinyl]phenyl}sulfinyl)benzenesulfonamide

2-Fluorobenzenesulfonamide was reacted with 4-bromothiophenol according to the method of Example 46 Step 1 using 1-methyl-2-pyrrolidinone as solvent. The resulting thioether was oxidised to the corresponding sulfoxide by the procedure of Example 16 Step 1. This was coupled with 4-fluorostyrene by the procedure of Example 107 to give the title compound. $\delta_H$ (500 MHz, d⁶ DMSO): 8.10 (1H, d, J=7.8 Hz), 7.91 (1H, d, J=7.7 Hz), 7.87 (2H, s), 7.81 (1H, t, J=7.4 Hz), 7.71-7.63 (7H, m), 7.31 (1H, d, J=16.5 Hz), 7.22-7.18 (3H, m).

Example 165

6-({4-[(E)-2-(4-fluorophenyl)vinyl]phenyl}sulfonyl)-3,4-dihydroisoquinolin-1(2H)-one Step 1
A suspension of 5-bromo-1-indanone (15 g, 71 mmol) in concentrated sulfuric acid (75 mL) was cooled to 0° C. Sodium azide (6.5 g, 100 mmol) was added portionwise over 1 hour. The reaction was allowed to warm to room temperature and stirred for 24 hours. The mixture was poured onto ice, neutralised with 4N sodium hydroxide and extracted with ethyl acetate. The organic layer was washed with brine, dried over MgSO₄ and concentrated in vacuo. The residue was purified by dry flash chromatography using 50-100% ethyl acetate/isohexane to give 6-bromo-3,4-dihydroisoquinolin-1(2H)-one (1.1 g, 7%). $\delta_H$ (500 MHz, CDCl₃): 7.92 (1H, d, J=8.3 Hz), 7.49 (1H, dd, J=1.4, 8.3 Hz), 7.39 (1H, d, J=0.9 Hz), 6.46 (1H, s), 3.57-3.55 (2H, m), 2.98 (2H, t, J=6.6 Hz).

Step 2
6-Bromo-3,4-dihydroisoquinolin-1(2H)-one (Step 1) was converted to the corresponding 6-iodo-derivative by the procedure of Example 135 Step 1. $\delta_H$ (400 MHz, CDCl₃): 7.75 (1H, d, J=8.2 Hz), 7.69 (1H, dd, J=1.5, 8.2 Hz), 7.60 (1H, d, J=1.0 Hz), 6.08 (1H, s), 3.56-3.52 (2H, m), 2.95 (2H, t, J=6.6 Hz).

Step 3
6-Iodo-3,4-dihydroisoquinolin-1(2H)-one (Step 2) was reacted with sodium 4-bromophhenylsulfinate by the procedure of Example 100 Step 1 and the product coupled with 4-fluorostyrene by the method of Example 107 to give the title compound. $\delta_H$ (500 MHz, d⁶ DMSO): 8.17 (1H, s), 8.01 (1H, d, J=8.1 Hz), 7.97-7.89 (4H, m), 7.80 (2H, d, J=8.4 Hz), 7.68 (2H, dd, J=5.6, 8.5 Hz), 7.44 (1H, d, J=16.4 Hz), 7.28 (1H, d, J=16.4 Hz), 7.22 (2H, t, J=8.8 Hz), 3.38-3.35 (2H, m), 2.99 (2H, t, J=6.4 Hz).

Example 166

7-({4-[(E)-2-(4-Fluorophenyl)vinyl]phenyl}sulfonyl)-1H-benzimidazole

Step 1
To a stirring slurry of tin(II) chloride dihydrate (8.28 g, 37 mmol) in conc. hydrochloric acid (40 mL) was added 2-bromo-6-nitroaniline (prepared as described in WO 02/22600, 1.99 g, 9.2 mmol), and the resulting mixture was stirred at room temperature for 5 min—an exotherm was observed. The mixture was stirred at reflux for 30 min, then allowed to cool to room temperature. The resulting slurry was poured onto crushed ice (~100 mL), and the pH was adjusted to 14 by addition of sodium hydroxide pellets. The mixture was washed with diethyl ether (5×100 mL), then the combined organic layers were dried over magnesium sulfate and concentrated in vacuo. The crude product was purified on a Biotage SP1 apparatus, using a 2%-20% ethyl acetate in dichloromethane eluant system on a 25M silica column, yielding 1,2-diamino-3-bromobenzene as a brown oil, which solidified upon standing (1.50 g, 87%) m/z (ES$^+$) 187, 189 [MH]$^+$.

Step 2

A solution of 1,2-diamino-3-bromobenzene (750 mg, 4.0 mmol) in formic acid (4 mL) was heated at 100° C. for 1 h. The mixture was allowed to cool to room temperature, then was basified (pH ~14) by the addition of 4 N sodium hydroxide solution. The product 4-bromo-1H-benzimidazole precipitated as an off-white solid, and was separated by filtration, washed with water and dried in a drying pistol under vacuum at 50° C. (654 mg, 83%). m/z (ES$^+$) 197, 199 [MH]$^+$.

Step 3

4-Bromo-1H-benzimidazole (285 mg, 1.5 mmol) was converted to 4-iodo-1H-benzimidazole by the procedure of Example 135 Step 1 yielding the product as an off-white solid (290 mg, 82%). m/z (ES$^+$) 245 [MH]$^+$.

Step 4

A mixture of 4-iodo-1H-benzimidazole (241 mg, 0.99 mmol), Intermediate 1 (309 mg, 1.1 mmol) and copper(I) iodide (564 mg, 3.0 mmol) in DMSO (8 mL) was degassed via three evacuation/nitrogen refill cycles, then was plunged into an oil bath pre-heated to 110° C., and was stirred under nitrogen for 2 h. The resulting mixture was diluted with ethyl acetate (40 mL) and was washed with conc. ammonia (1×20 mL). The aqueous phase was washed with ethyl acetate (2×40 mL), then the combined organic layers were washed with water (1×40 mL), with saturated sodium chloride solution (1×40 mL), then were dried over magnesium sulfate and concentrated in vacuo. The crude product was purified by flash chromatography on silica gel, eluting with 2.5% methanol in dichloromethane, then was further purified on another silica gel column, eluting initially with 50% diethyl ether in dichloromethane, then with neat diethyl ether, yielding the title compound as a white solid (37 mg, 10%). $^1$H NMR (500 MHz, d$^6$ DMSO): $\delta_H$ 12.96 (1H, s), 8.40 (1H, s), 8.13 (2H, d, J=8.4 Hz), 7.95 (1H, d, J=8.0 Hz), 7.88 (1H, d, J=7.5 Hz), 7.78 (2H, d, J=8.4 Hz), 7.68 (2H, dd, J=5.7, 8.7 Hz), 7.45-7.41 (2H, m), 7.28-7.22 (3H, m). m/z (ES$^+$) 379 [MH]$^+$.

Example 167

1-[2-({4-[(E)-2-(4-fluorophenyl)vinyl]phenyl}sulfonyl)phenyl]-2-hydroxyethanone

Step 1

A mixture of 2-iodoacetophenone (1 g, 4.1 mmol) and hydroxy(tosyloxy)iodobenzene (1.86 g, 4.92 mmol) in dimethylsulfoxide:water (40 mL:2 mL) was stirred at room temperature overnight. The reaction mixture was partitioned between water and ethyl acetate. The organic layer was washed with brine, dried over MgSO$_4$ and concentrated in vacuo. The residue was purified by flash column chromatography on silica, eluting with 40% ethyl acetate/isohexane, to give 2-hydroxy-1-(2-iodophenyl)ethanone (126 mg, 12%). $\delta_H$ (400 MHz, d$^6$ DMSO): 7.94 (1H, dd, J=0.9, 7.8 Hz), 7.54 (1H, dd, J=1.8, 7.7 Hz), 7.49-7.45 (1H, m), 7.25-7.21 (1H, m), 5.37 (1H, t, J=6.0 Hz), 4.52 (2H, d, J=6.0 Hz).

Step 2

The title compound was prepared from 2-hydroxy-1-(2-iodophenyl)ethanone (Step 1) and sodium 4-[(E)-2-(4-fluorophenyl)vinyl]benzenesulfinate according to the method of Example 135 Step 2. $\delta_H$ (500 MHz, d$^6$ DMSO): 8.07 (1H, d, J=7.8 Hz), 7.88 (2H, d, J=8.4 Hz), 7.80 (2H, d, J=8.4 Hz), 7.76-7.66 (4H, m), 7.54 (1H, d, J=7.4 Hz), 7.45 (1H, d, J=16.4 Hz), 7.28 (1H, d, J=16.4 Hz), 7.23 (2H, t, J=8.7 Hz), 5.47 (1H, t, J=5.9 Hz), 4.54 (2H, d, J=5.9 Hz).

Example 168

1-[2-({4-[(E)-2-(4-fluorophenyl)vinyl]phenyl}sulfonyl)phenyl]ethane-1,2-diol

A mixture of 1-[2-({4-[(E)-2-(4-fluorophenyl)vinyl]phenyl}sulfonyl)phenyl]-2-hydroxyethanone (Example 167, 20 mg, 0.05 mmol) and sodium borohydride (10 mg, 0.26 mmol) in methanol (2 mL) and dichloromethane (0.5 mL) was stirred at room temperature for 30 minutes. The reaction was quenched with water and concentrated in vacuo. The residue was partitioned between ethyl acetate and water. The organic layer was washed with brine, dried over MgSO$_4$ and concentrated in vacuo. $\delta_H$ (500 MHz, d$^6$ DMSO): 8.04 (1H, d, J=7.9 Hz), 7.84-7.79 (4H, m), 7.74 (1H, d, J=7.7 Hz), 7.70-7.67 (3H, m), 7.53 (1H, t, J=7.3 Hz), 7.44 (1H, d, J=16.3 Hz), 7.29 (1H, d, J=16.4 Hz), 7.23 (2H, t, J=8.6 Hz), 5.36 (2H, s), 4.71 (1H, s), 3.32 (1H, s), 3.17 (1H, s).

Examples 169-175

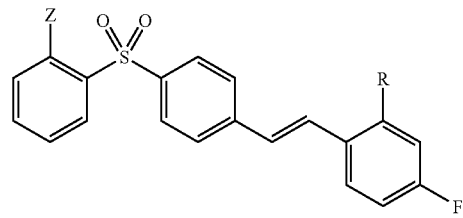

The following were prepared from the appropriate iodobenzene derivative and Intermediate 1 or Intermediate 2 by the procedure of Example 135 Step 2.

In the case of Examples 169-174, the relevant iodobenzene derivatives were obtained by alkylation of 2-iodoaniline or 2-iodophenol with bromoacetonitrile, bromoacetamide or methyl bromoacetate as appropriate.

| Example | Z | R | $\delta_H$(500MHz, d$^6$ DMSO) or m/z(ES$^+$) |
|---|---|---|---|
| 169 | —NHCH$_2$CH$_2$CN | H | 7.97(2H, d, J=8.3Hz), 7.90(1H, d, J=7.6Hz), 7.78(2H, d, J=8.3Hz), 7.69(2H, t, J=7.0Hz), 7.57(1H, t, J=7.4Hz), 7.45(1H, d, J=16.4Hz), 7.30–7.22(3H, m), 6.96–6.93(2H, m), 6.85(1H, t, J=6.4Hz), 4.45(2H, d, J=6.4Hz). |

-continued

| Example | Z | R | $\delta_H$(500MHz, d⁶ DMSO) or m/z(ES⁺) |
|---|---|---|---|
| 170* | —NHCH₂CONH₂ | H | 7.92(2H, d, J=8.4Hz), 7.80(1H, dd, J=1.4, 8.0Hz), 7.74(2H, d, J=8.5Hz), 7.66(2H, dd, J=5.6, 8.6Hz), 7.48(1H, s), 7.42(2H, dd, J=4.3, 16.4Hz), 7.26–7.20(4H, m), 6.87(1H, t, J=4.5Hz), 6.76(1H, t, J=7.5Hz), 6.53(1H, d, J=8.3Hz), 3.74(2H, d, J=4.5Hz). |
| 171 | —NHCH₂CO₂Me | H | 7.93(3H, t, J=8.8Hz), 7.55(2H, d, J=7.8Hz), 7.47(2H, t, J=5.9Hz), 7.37(1H, t, J=7.1Hz), 7.14–6.96(4H, m), 6.90(1H, s), 6.80(1H, s), 6.50(1H, d, J=8.1Hz), 3.93(2H, d, J=4.7Hz), 3.80(3H, s). |
| 172 | —OCH₂CO₂Me | H | 8.03(1H, d, J=7.7Hz), 7.95(2H, d, J=7.9Hz), 7.73(2H, d, J=8.0Hz), 7.68(2H, t, J=6.7Hz), 7.62(1H, t, J=7.8Hz), 7.42(1H, d, J=16.4Hz), 7.28(1H, d, J=16.5Hz), 7.24–7.18(3H, m), 7.09(1H, d, J=8.4Hz), 4.84(2H, s), 3.63(3H, s). |
| 173 | —OCH₂CONH₂ | H | 7.77(1H, dd, J=1.6, 7.7Hz), 7.53(1H, s), 7.36–7.32(1H, m), 7.16(1H, s), 6.91(1H, dd, J=1.2, 8.3Hz), 6.79–6.75(1H, m), 4.51(2H, s). |
| 174 | —OCH₂CONH₂ | F | 8.02(1H, d, J=7.8Hz), 7.90–7.79(5H, m), 7.67(1H, t, J=7.8Hz), 7.59(1H, s), 7.41–7.23(5H, m), 7.16–7.13(2H, m), 4.54(2H, s). |
| 175 | —SO₂Me | H | 417[MH⁺]. |

*prepared by hydrolysis of Example 169 by the procedure of Example 57.

Example 176

2-({4-[(E)-2-(2,4-difluorophenyl)vinyl]phenyl}sulfonyl)benzaldehyde see Example 139 Step 1.

$\delta_H$ (500 MHz, d⁶ DMSO): 10.68 (1H, s), 8.18 (1H, d, J=7.6 Hz), 7.98-7.83 (8H, m), 7.40 (2H, q, J=14.5 Hz), 7.32-7.26 (1H, m), 7.17-7.13 (1H, m).

Example 177

2-methyl-N-[2-({4-[(E)-2-(4-fluorophenyl)vinyl]phenyl}sulfonyl)benzyl]propane-2-sulfinamide A mixture of 2-({4-[(E)-2-(2,4-difluorophenyl)vinyl]phenyl}sulfonyl)benzaldehyde (Example 176, 500 mg, 1.44 mmol), 2-methyl-2-propanesulfinamide (192 mg, 1.58 mmol) and titanium(IV) ethoxide (0.6 mL, 2.88 mmol) in tetrahydrofuran (7 mL) was heated to reflux for 4 hours. The cooled reaction mixture was partitioned between ethyl acetate and brine. The organic layer was dried over MgSO₄ and evaporated in vacuo. The residue was taken up in methanol/dichloromethane (3:1, 16 mL) and sodium borohydride (424 mg, 8.64 mmol) added portionwise. After stirring at room temperature for 10 minutes, water and dichloromethane were added. The organic layer was dried over MgSO₄ and concentrated in vacuo. The residue was purified by flash column chromatography on silica, eluting with 50-90% ethyl acetate/isohexane, followed by recrystallisation to give the title compound as a white solid. $\delta_H$ (500 MHz, d⁶ DMSO): 8.11 (1H, d, J=7.8 Hz), 7.84-7.80 (4H, m), 7.73-7.66 (4H, m), 7.59-7.57 (1H, m), 7.45 (1H, d, J=16.4 Hz), 7.30 (1H, d, J=16.5 Hz), 7.23 (2H, t, J=8.8 Hz), 5.78 (1H, t, J=6.4 Hz), 4.45-4.35 (2H, m), 1.07 (9H, s).

Example 178

[2-({4-[(E)-2-(4-fluorophenyl)vinyl]phenyl}sulfonyl)benzyl]amine

2-Methyl-N-[2-({4-[(E)-2-(4-fluorophenyl)vinyl]phenyl}sulfonyl)benzyl]propane-2-sulfinamide (Example 177, 285 mg, 0.6 mmol) was dissolved in methanol (5 mL) and 4N HCl in dioxane (5 mL) and stirred overnight at room temperature. The solvent was removed in vacuo and the residue triturated with diethyl ether to give the title compound as the hydrochloride salt (221 mg, 90%). $\delta_H$ (500 MHz, d⁶ DMSO): 8.46-8.38 (3H, m), 8.13 (1H, d, J=7.8 Hz), 7.89 (2H, d, J=8.3 Hz), 7.84-7.78 (3H, m), 7.71-7.67 (4H, m), 7.45 (1H, d, J=16.5 Hz), 7.30 (1H, d, J=16.5 Hz), 7.23 (2H, t, J=8.7 Hz), 4.28 (2H, s).

Example 179

N-[2-({4-[(E)-2-(4-fluorophenyl)vinyl]phenyl}sulfonyl)benzyl]methanesulfonamide

[2-({4-[(E)-2-(4-Fluorophenyl)vinyl]phenyl}sulfonyl)benzyl]amine hydrochloride (Example 178, 120 mg, 0.3 mmol) was added to a rapidly stirred mixture of methanesulfonyl chloride (50 μL, 0.6 mmol) in 1M sodium hydroxide (3 mL) and dichloromethane (3 mL). After 30 minutes, further methanesulfonyl chloride (100 μL, 1.2 mmol) and 4M sodium hydroxide (1 mL) were added and the reaction stirred for 30 minutes. The layers were separated and the organic layer washed with 1N HCl, dried over MgSO₄ and concentrated in vacuo. The residue was purified by flash column chromatography on silica, eluting with 60% ethyl acetate/isohexane to give the title compound as a white solid (30 mg, 22%). $\delta_H$ (500 MHz, d⁶ DMSO): 8.10 (1H, d, J=7.9 Hz), 7.90 (2H, d, J=8.4 Hz), 7.80 (2H, d, J=8.4 Hz), 7.75-7.67 (4H, m), 7.59 (1H, t, J=7.3 Hz), 7.55 (1H, s), 7.44 (1H, d, J=16.4 Hz), 7.29 (1H, d, J=16.5 Hz), 7.22 (2H, t, J=8.8 Hz), 4.44 (2H, s), 2.89 (3H, s).

Example 180

[2-({4-[(E)-2-(2,4-difluorophenyl)vinyl]phenyl}sulfonyl)phenyl]amine 2,4-Difluoro-1-((E)-2-{4-[(2-nitrophenyl)sulfonyl]phenyl}vinyl)benzene was prepared according to the method of Example 135 Step 2 using 2-iodonitrobenzene and Intermediate 2.

Iron powder (808 mg, 14.45 mmol) was added portionwise to a stirred suspension of this product (1.16 g, 2.89 mmol) in acetic acid (9 mL). The reaction was heated at 70° C. for 3 hours then cooled and concentrated under a stream of nitrogen overnight. The residue was partitioned between water and ethyl acetate and the mixture filtered through Hyflo®. The organic layer was washed with brine, dried over $MgSO_4$ and concentrated in vacuo to give the title compound (977 mg, 91%). $\delta_H$ (500 MHz, $d^6$ DMSO): 7.90-7.78 (5H, m), 7.68 (1H, d, J=7.0 Hz), 7.40-7.26 (4H, m), 7.14 (1H, t, J=8.3 Hz), 6.77 (1H, d, J=8.2 Hz), 6.67 (1H, t, J=7.5 Hz), 6.14 (2H, s).

Example 181

1-({4-[(E)-2-(4-fluorophenyl]vinyl]phenyl}sulfonyl)-2-(2,2,2-trifluoroethoxy)benzene 1-Fluoro-2-({4-[(E)-2-(4-fluorophenyl]vinyl]phenyl}sulfonyl)benzene was prepared from 2-fluoroiodobenzene according to the method of Example 135 step 2.

To sodium hydride (60% dispersion in mineral oil, 10 mg, 0.21 mmol) was added 2,2,2-trifluoroethanol (23 μL, 0.21 mmol) followed immediately by N,N-dimethylformamide (0.5 mL). The reagents were heated to 50° C. in a sealed tube for 1 hour, then the fluorophenyl sulfone (50 mg, 0.14 mmol) was added and the reaction heated to 50° C. for 24 hours. Water and dichloromethane were added and the organic layer evaporated under a stream of nitrogen. The residue was recrystallised from dichloromethane/isopropyl alcohol to give the title compound as a colourless solid (34 mg, 56%). $\delta_H$ (500 MHz, $d^6$ DMSO): 8.08 (1H, dd, J=1.5, 7.9 Hz), 7.82 (2H, d, J=8.4 Hz), 7.75 (2H, d, J=8.4 Hz), 7.72-7.66 (3H, m), 7.43 (1H, d, J=16.4 Hz), 7.29 (2H, t, J=7.6 Hz), 7.26-7.20 (3H, m), 4.80 (2H, q, J=8.7 Hz).

Examples 182-186

The following 5 compounds were prepared according to the method of Example 181 using the appropriate alcohol in place of trifluoroethanol.

| Example | R | $\delta_H$ (500 MHz, $d^6$ DMSO) |
|---|---|---|
| 182 | pyridin-3-ylmethyl | 8.82(1H, s), 8.77(1H, s), 8.12(1H, d, J=7.4Hz), 8.06(1H, d, J=7.9Hz), 7.85(1H, t, J=6.1Hz), 7.71-7.63(7H, m), 7.40(1H, d, J=16.5Hz), 7.31-7.21(5H, m), 5.31 (2H, s). |
| 183 | pyridin-4-ylmethyl | 8.85(2H, s), 8.08(1H, d, J=7.8Hz), 7.80 (2H, d, J=8.3Hz), 7.75 (2H, d, J=5.1Hz), 7.71-7.65(5H, m), 7.38(1H, d, J=16.4Hz), 7.28-7.20(5H, m), 5.45(2H, s). |
| 184 | 2-(dimethylamino)ethyl | 10.60(1H, s), 8.05(1H, d, J=7.7Hz), 7.87 (2H, d, J=8.3Hz), 7.78(2H, d, J=8.4Hz), 7.73–7.67(3H, m), 7.41(1H, d, J=16.4Hz), 7.29(1H, d, J=16.4Hz), 7.27-7.21(4H, m), 4.40(2H, t, J=4.7Hz), 3.40(2H, t, J=4.6Hz), 2.83(6H, s). |
| 185 | pyridin-2-ylmethyl | 8.61(1H, s), 8.05(1H, dd, J=1.4, 7.8Hz), 7.91-7.88(1H, m), 7.75(2H, d, J=8.4Hz), 7.69-7.63(5H, m), 7.46-7.43(1H, m), 7.38(1H, d, J=16.4Hz), 7.28-7.20(6H, m), 5.25(2H,s). |
| 186 | 3-(dimethylamino)propyl | 8.03(1H, d, J=7.6Hz), 7.85(2H, d, J=8.4 Hz), 7.80(2H, d, J=8.5Hz), 7.70-7.66(3H, m), 7.42(1H, d, J=16.4Hz), 7.29(1H, d, J=16.5Hz), 7.25-7.19(3H, m), 7.16(1H, d, J=8.5Hz), 4.07(2H, t, J=5.8Hz), 3.10(2H, s), 2.76(6H, s), 2.07-2.01(2H, m). |

Example 187

2-({4-[(E)-2-(4-fluorophenyl)vinyl]-3-methylphenyl}sulfonyl)benzamide

Step 1

2-[(4-Bromo-3-methylphenyl)sulfonyl]benzamide was prepared from sodium 4-bromo-3-methylbenzenesulfinate (Example 139 Step 1) and 2-iodobenzamide according to the method of Example 135 Step 2.

Step 2

The title compound was prepared from 2-[(4-bromo-3-methylphenyl)sulfonyl]benzamide (Step 1) and [(E)-2-(4-fluorophenyl)vinyl]boronic acid according to the method of Example 1 Step 4. m/z ($ES^+$) 379 [$(M-NH_2)^+$].

Example 188

2-({4-[(E)-2-(2,4-difluorophenyl)vinyl]-3-methylphenyl}sulfonyl)benzamide

Prepared according to the method of Example 187 using [(E)-2-(2,4-difluorophenyl)vinyl]boronic acid in Step 2. m/z ($ES^+$) 397 [$(M-NH_2)^+$].

Example 189

1-({4-[(E)-2-(4-fluorophenyl)vinyl]phenyl}sulfinyl)-2-(methylsulfonyl)benzene

Prepared from 1-iodo-2-(methylsulfonyl)benzene by reaction with 4-chlorobenzenethiol by the method of Example 1 Step 1, followed by oxidation according to Example 16 Step 1 and coupling with 4-fluorostyrene by the method of Example 107. m/z (ES+) 401 [MH+].

Examples 190-205

The following compounds were prepared from the relevant aryl bromide and Intermediate 1 or Intermediate 2 as appropriate, according to the method of Example 135:

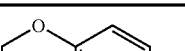

| Example | Ar | R¹ | δ_H (500 MHz, d⁶ DMSO) or m/z (ES+) [MH+] |
|---|---|---|---|
| 190 | 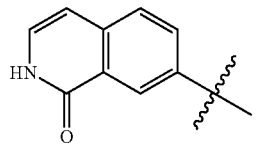 | H | 7.88(2H, d, J=8.4Hz), 7.57(2H, d, J=8.4Hz), 7.49-7.42(4H, m), 7.14(1H, d, J=16.3Hz), 7.06(2H, t, J=8.6Hz), 6.99(1H, d, J=16.3Hz), 6.94(1H, d, J=8.4Hz), 4.28-4.26(4H, m) (CDCl₃) |
| 191 | 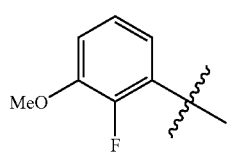 | H | 8.64(1H, d, J=1.8Hz), 8.15(1H, dd, J=2.1, 8.5Hz), 7.96(2H, d, J=8.5Hz), 7.86(1H, d, J=8.5Hz), 7.80(2H, d, J=8.4Hz), 7.67(2H, dd, J=5.6, 8.7Hz), 7.42(1H, d, J=16.5Hz), 7.36(1H, d, J=7.0Hz), 7.27(1H, d, J=16.4Hz), 7.22(2H, t, J=8.8Hz), 6.63(1H, d, J=7.1Hz), 5.73(1H, s) |
| 192 | 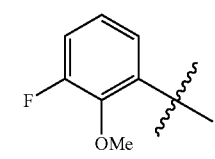 | H | 7.93(2H, d, J=8.5Hz), 7.83(1H, dd, J=2.2, 10.6Hz), 7.78(3H, d, J=8.6Hz), 7.68(2H, dd, J=5.6, 8.7Hz), 7.43(1H, d, J=16.5Hz), 7.37(1H, t, J=8.5Hz), 7.27(1H, d, J=16.5Hz), 7.22(2H, t, J=8.9Hz), 3.90(3H, s) |
| 193 | 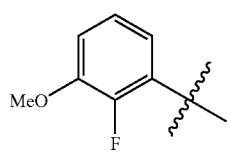 | F | 7.89-7.83(6H, m), 7.68-7.63(1H, m), 7.43-7.35(3H, m), 7.32-7.28(1H, m), 7.16-7.14(1H, m), 3.75(3H, d, J=1.9Hz) |
| 194 |  | F | 7.92(2H, t, J=7.3Hz), 7.87-7.80(4H, m), 7.77(1H, dd, J=8.7, 1.3Hz), 7.41-7.33(3H, m), 7.33-7.27(1H, m), 7.17-7.13(1H, m), 3.89(3H, s) |

-continued

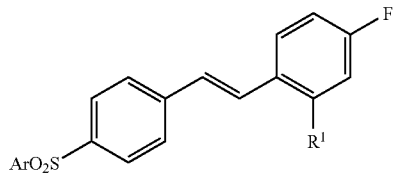

| Example | Ar | R¹ | δ_H (500 MHz, d⁶ DMSO) or m/z (ES+) [MH+] |
|---|---|---|---|
| 195 | | F | 8.25(1H, dd, J=1.6, 7.9Hz), 7.95(2H, d, J=8.4Hz), 7.62-7.54(4H, m), 7.43(1H, t, J=7.7Hz), 7.29(1H, d, J=16.5Hz), 7.22(1H, d, J=8.1Hz), 7.11(1H, d, J=16.5Hz), 6.93-6.89(1H, m), 6.87-6.83(1H, m), 6.53(1H, t, J=74.2 Hz) (CDCl₃) |
| 196 | | F | 7.98-7.82(5H, m), 7.76-7.70(2H, m), 7.46-7.36(3H, m), 7.33-7.27(1H, m), 7.18-7.09(1H, m) |
| 197 | | F | 7.94(2H, d, J=8.4Hz), 7.89-7.81(5H, m), 7.52-7.50(1H, m), 7.41(2H, q, J=14.7Hz), 7.33-7.27(1H, m), 7.16(1H, t, J=8.5Hz) |
| 198 | | H | 7.89(2H, d, J=8.4Hz), 7.78(2H, d, J=8.4 Hz), 7.69(2H, dd, J=5.6, 8.6Hz), 7.66-7.60(1H, m), 7.43(1H, d, J=16.4 Hz), 7.29(1H, d, J=16.5 Hz), 7.23(2H, t, J=8.8 Hz), 6.99-6.95(2H, m), 3.72(3H, s) |
| 199 | 2-MeO—Ph | H | 8.00(1H, dd, J=1.6, 7.8 Hz), 7.85(2H, d, J=8.5 Hz), 7.76(2H, d, J=8.4 Hz), 7.70-7.64(3H, m), 7.42(1H, d, J=16.4Hz), 7.28(1H, d, J=16.5Hz), 7.24-7.14(4H, m), 3.73 (3H, s) |
| 200 | 2-OH—Ph | H | 7.90(2H, d, J=8.4Hz), 7.67(1H, dd, J=1.5, 8.0 Hz), 7.59(2H, d, J=8.4 Hz), 7.48(2H, dd, J=5.4, 8.6Hz), 7.45-7.43(1H, m), 7.15(1H, d, J=16.3 Hz), 7.06(2H, t, J=8.6 Hz), 7.00-6.94(3H, m) |
| 201 | 2-MeO—Ph | F | 8.00(1H, dd, J=1.5, 7.8Hz), 7.88-7.84(3H, m), 7.80(2H, d, J=8.5 Hz), 7.67-7.65(1H, m), 7.37(2H, q, J=13.3Hz), 7.31-7.27(1H, m), 7.19-7.13(3H, m), 3.73(3H, s) |

-continued

| Example | Ar | R$^1$ | $\delta_H$ (500 MHz, d$^6$ DMSO) or m/z (ES$^+$) [MH$^+$] |
|---|---|---|---|
| 202 | 2-OH—Ph | F | 10.75(1H, s), 7.92-7.84 (4H, m), 7.79(2H, d, J=8.2Hz), 7.48(1H, t, J=7.2Hz), 7.40-7.28 (3H, m), 7.15(1H, t, J=7.6Hz), 7.00(1H, t, J=7.5Hz), 6.89(1H, d, J=8.1Hz) |
| 203 | 2-CHO—Ph | H | 367 |
| 204 | 2-MeCO—Ph | F | 8.08(1H, d, J=7.9Hz), 7.89-7.83(5H, m), 7.77 (1H, t, J=7.4Hz), 7.69 (1H, t, J=7.7Hz), 7.61 (1H, d, J=7.4Hz), 7.39 (2H, q, J=15.8Hz), 7.32-7.28(1H, m), 7.15(1H, t, J=8.5Hz), 2.59(3H, s) |
| 205 | 2-MeOCH$_2$—Ph | F | 8.11(1H, d, J=7.9Hz), 7.88-7.81(5H, m), 7.72 (1H, t, J=7.5Hz), 7.64-7.58(2H, m), 7.38 (2H, q, J=13.4Hz), 7.29(1H, t, J=10.1Hz), 7.15(1H, t, J=8.4Hz), 4.66(2H, s), 3.20(3H, s) |

Example 206

2-({4-[(E)-2-(2,4-difluorophenyl]vinyl]phenyl}sulfonyl)-3-methoxybenzamide

Prepared by analogy with Example 198 (using Intermediate 2 in place of Intermediate 1), followed by displacement of the fluorine substituent with CN according to the method of Example 127, then hydrolysis of the nitrile group as in Example 57. m/z (ES$^+$) 412 [(M-NH$_2$)$^+$].

Example 207

2-({4-[(E)-2-(2-chlorophenyl]vinyl]phenyl}sulfonyl)benzamide

Prepared by reaction of 2-iodo-benzamide with 4-chlorobenzenethiol by the method of Example 1 Step 1, followed by reaction with tributyl(vinyl)tin as in Example 6 Step 1 and coupling with 2-chloroiodobenzene by the method of Example 6 Step 2. m/z (ES$^+$) 398 [MH$^+$].

Example 208

2-({4-[(E)-2-(2-chloro-4-fluorophenyl]vinyl]phenyl}sulfonyl)benzamide

Prepared as in Example 207 using 2-chloro-4-fluoroiodobenzene in the last step. m/z (ES$^+$) 416 [MH$^+$].

Example 209

1-({4-[(E)-2-(4-fluorophenyl)vinyl]phenyl}sulfonyl)-2,3-dimethoxybenzene

A mixture of 2-fluoro-1-({4-[(E)-2-(4-fluorophenyl)vinyl]phenyl}sulfonyl)-3-methoxybenzene (Example 192, 45 mg, 0.116 mmol) and sodium methoxide (0.5M in methanol, 1 mL) was heated to 150° C. for 10 minutes in a microwave reactor. A further 0.5 mL sodium methoxide was added and heating continued at 150° C. for 30 minutes. The cooled reaction mixture was partitioned between water and ethyl acetate. The organic layer was washed with brine, dried over MgSO$_4$ and concentrated in vacuo. The residue was purified by flash column chromatography on silica, eluting with 20% ethyl acetate/isohexane, to give the title compound. $\delta_H$ (500 MHz, d$^6$ DMSO): 7.91 (2H, d, J=8.5 Hz), 7.76 (2H, d, J=8.4 Hz), 7.67 (2H, dd, J=5.7, 8.7 Hz), 7.52 (1H, dd, J=2.2, 8.5 Hz), 7.39 (2H, d, J=2.3 Hz), 7.28 (1H, s), 7.25-7.19 (2H, m), 7.14 (1H, d, J=8.6 Hz), 3.82 (3H, s), 3.80 (3H, s).

Example 210

4-({4-[(E)-2-(4-fluorophenyl)vinyl]phenyl}sulfonyl)-1H-isoindole-1,3(2H)-dione Step 1

A solution of 3-iodophthalic acid (0.9 g, 3.08 mmol) in acetic anhydride (5 mL) was heated to reflux under nitrogen overnight. After cooling, the solvent was removed in vacuo and the residue purified by trituration with ethanol to give 4-iodo-2-benzofuran-1,3-dione (0.55 g, 65%).

Step 2

A solution of 4-iodo-2-benzofuran-1,3-dione (0.55 g, 2.01 mmol) and urea (0.24 g, 3.99 mmol) in xylene (5 mL) was heated to reflux overnight. After cooling, the solvent was removed in vacuo and the residue partitioned between water and ethyl acetate. The aqueous phase was extracted with ethyl acetate and the combined organic layers washed with brine, dried over MgSO$_4$ and concentrated in vacuo while loading onto silica. Dry flash column chromatography using 5-10% ethyl acetate/isohexane gave 4-iodo-1H-isoindole-1,3(2H)-dione as a pale yellow solid (330 mg, 60%).

Step 3

The title compound was prepared from 4-iodo-1H-isoindole-1,3(2H)-dione according to the method of Example 135 Step 2. $\delta_H$ (500 MHz, d$^6$ DMSO): 11.55 (1H, s), 8.47 (1H, dd, J=1.3, 7.5 Hz), 8.13-8.07 (2H, m), 8.00 (2H, d, J=8.5 Hz), 7.77 (2H, d, J=8.5 Hz), 7.67 (2H, dd, J=5.6, 8.7 Hz), 7.44 (1H, d, J=16.4 Hz), 7.27 (1H, d, J=16.4 Hz), 7.22 (2H, t, J=8.9 Hz).

Example 211

7-({4-[(E)-2-(4-fluorophenyl)vinyl]phenyl}sulfonyl)isoindolin-1-one

7-Bromoisoindolin-1-one was prepared by bromination of methyl 2-bromo-6-methyl benzoate (using N-bromosuccinimide and benzoyl peroxide in refluxing CCl$_4$) and treatment of the resulting benzyl bromide with ammonia gas in refluxing ethanol. Further elaboration via the procedure of Example 135 gave the title compound. $\delta_H$ (500 MHz, d$^6$ DMSO): 8.62 (1H, s), 8.24 (1H, d, J=7.3 Hz), 7.96 (2H, d, J=8.4 Hz), 7.91-7.85 (2H, m), 7.71-7.64 (4H, m), 7.40 (1H, d, J=16.5 Hz), 7.25 (2H, d, J=16.2 Hz), 7.21 (1H, d, J=8.8 Hz), 4.36 (2H, s).

Example 212

[3-({4-[(E)-2-(4-fluorophenyl)vinyl]phenyl}sulfonyl)phenyl]amine hydrochloride

Prepared by analogy with Example 180.
$\delta_H$(500 MHz, d$^6$ DMSO): 7.85 (2H, d, J=8.4 Hz), 7.79 (2H, d, J=8.4 Hz), 7.67 (2H, dd, J=5.6, 8.5 Hz), 7.42 (1H, d, J=16.5 Hz), 7.34-7.18 (6H, m), 6.94 (1H, d, J=7.3 Hz); m/z (ES$^+$) 354 [MH$^+$].

Example 213

N-[3-({4-[(E)-2-(4-fluorophenyl)vinyl]phenyl}sulfonyl)phenyl]sulfamide

To dichloromethane (1 mL) at 0° C. was added chlorosulfonyl isocyanate (0.03 mL, 0.26 mmol) and tert-butanol (0.03 mL, 0.26 mmol). The mixture was stirred for 10 minutes then triethylamine (0.054 mL, 0.39 mmol) was added followed by [3-({4-[(E)-2-(4-fluorophenyl)vinyl]phenyl}sulfonyl)phenyl]amine hydrochloride (Example 212, 100 mg, 0.26 mmol). The reaction was allowed to warm to room temperature and stirred for 2 hours. The mixture was partitioned between ethyl acetate and water. The organic layer was washed with brine, dried over MgSO$_4$ and evaporated. The residue was treated with trifluoroacetic acid for 15 minutes then evaporated. The residue was partitioned between ethyl acetate and 1M sodium hydroxide. The organic layer was washed with brine, dried over MgSO$_4$ and evaporated. The residue was purified by flash column chromatography on silica, eluting with 50% ethyl acetate/isohexane to give the title compound (40 mg, 36%). $\delta_H$ (500 MHz, d$^6$ DMSO): 9.94 (1H, s), 7.89 (2H, d, J=8.4 Hz), 7.79 (2H, d, J=8.4 Hz), 7.71-7.65 (3H, m), 7.51-7.48 (2H, m), 7.44-7.38 (2H, m), 7.30-7.20 (5H, m); m/z (ES$^+$) 431 [MH$^+$].

Example 214

N-[3-({4-[(E)-2-(4-fluorophenyl)vinyl]phenyl}sulfonyl)phenyl]urea

A mixture of [3-({4-[(E)-2-(4-fluorophenyl)vinyl]phenyl}sulfonyl)phenyl]amine hydrochloride (Example 212, 100 mg, 0.26 mmol) and potassium cyanate (63 mg, 0.78 mol) in acetic acid (3 mL) and water (0.5 mL) was stirred at room temperature for 16 hours. The acetic acid was removed in vacuo and the residue partitioned between ethyl acetate and water. The organic layer was washed with aqueous sodium hydrogencarbonate solution and brine, dried over MgSO$_4$ and evaporated in vacuo. The residue was purified by flash column chromatography on silica, eluting with 20% ethyl acetate/isohexane then 40% ethyl acetate/isohexane, to give the title compound. $\delta_H$ (500 MHz, d$^6$ DMSO): 8.96 (1H, s), 8.13 (1H, s), 7.86 (2H, d, J=8.5 Hz), 7.79 (2H, d, J=8.5 Hz), 7.67 (2H, dd, J=5.6, 8.7 Hz), 7.54-7.52 (1H, m), 7.44-7.40 (3H, m), 7.27 (1H, d, J=16.4 Hz), 7.22 (2H, t, J=8.8 Hz), 5.98 (2H, s).

Example 215

N-ethyl-N'-[3-({4-[(E)-2-(4-fluorophenyl)vinyl]phenyl}sulfonyl)phenyl]urea

A mixture of [3-({4-[(E)-2-(4-fluorophenyl)vinyl]phenyl}sulfonyl)phenyl]amine hydrochloride (Example 212, 100 mg, 0.26 mmol) and triethylamine (0.05 mL, 0.36 mmol) in tetrahydrofuran (2 mL) was cooled to 0° C. and ethyl isocyanate (0.08 mL, 0.31 mmol) added. The reaction was allowed to warm to room temperature and stirred for 3 hours. The reaction mixture was partitioned between ethyl acetate and water. The organic layer was washed with brine, dried over MgSO$_4$ and evaporated. The residue was purified by flash column chromatography on silica, eluting with 40% ethyl acetate/isohexane, followed by trituration with diethyl ether to give the title compound as a white solid (27 mg, 24%).
$\delta_H$(500 MHz, d$^6$ DMSO): 8.85 (1H, s), 8.15 (1H, s), 7.86 (2H, d, J=8.4 Hz), 7.79 (2H, d, J=8.4 Hz), 7.67 (2H, dd, J=5.7, 8.5 Hz), 7.50-7.48 (1H, m), 7.43-7.40 (3H, m), 7.27 (1H, d, J=16.5 Hz), 7.22 (2H, t, J=8.8 Hz), 6.20 (1H, t, J=5.4 Hz), 3.12-3.06 (2H, m), 1.03 (3H, t, J=7.1 Hz).

Example 216

4-({4-[(E)-2-(4-fluorophenyl)vinyl]phenyl}sulfonyl)-1,2-benzisoxazol-3-amine

A solution of acetohydroxamic acid (75 mg, 1 mmol) in N,N-dimethylformamide was treated at room temperature with potassium tert-butoxide and stirred for 30 minutes. 2-fluoro-6-({4-[(E)-2-(4-fluorophenyl)vinyl]phenyl}sulfonyl)benzonitrile (Example 112, 100 mg, 0.26 mmol) was added and the reaction stirred for 5 hours. The reaction mixture was poured into water and extracted with ethyl acetate. The organic layer was washed with brine (×5), dried over MgSO$_4$ and evaporated. The residue was purified by flash column chromatography on silica to give the title compound (30 mg, 29%).
$\delta_H$ (500 Hz, CDCl$_3$): 8.00 (2H, d, J=8.6 Hz), 7.92 (1H, dd, J=7.3, 0.85 Hz), 7.68-7.58 (4H, m), 7.49-7.46 (2H, m), 7.15 (1H, d, J=16.3 Hz), 7.06 (2H, t, J=8.6 Hz), 6.98 (1H, d, J=16.3 Hz).

What is claimed is:
1. A compound of formula I:

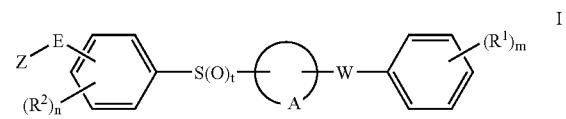

wherein:
m is 0, 1, 2 or 3;
n is 0, 1 or 2;
t is 1 or 2;
A represents a phenyl ring optionally bearing up to 2 additional substituents selected from halogen, CN, CF$_3$, OR$^a$, CO$_2$R$^a$, CONR$^a$R$^b$, NR$^a$R$^b$ and C$_{1-4}$alkyl which is optionally substituted with halogen, CN, CF$_3$, OR$^a$, CO$_2$R$^a$, CONR$^a$R$^b$ or NR$^a$R$^b$;
W represents —CR$^3$=CR$^5$, where R$^3$ and R$^5$ are selected from H, OH and F but mot more than one of R$^3$ and R$^5$ is other than H;
E represents a chemical bond or a straight or branched alkylene chain containing from 1 to 4 carbon atoms, optionally incorporating an oxygen atom to form an ether linkage and optionally comprising a hydroxy substituent;
Z is selected from H, halogen, CN, nitro, CF$_3$, OCF$_3$, —R$^a$, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —NR$^a$CONR$^a$R$^b$, NR$^a$SOR$^b$, NR$^a$SO$_2$R$^b$, CONHCOR$^a$, NHCH$_2$CO$_2$R$^a$, NHCH$_2$CONR$^a$R$^b$, —NR$^a$SO$_2$NR$^a$R$^b$, —COR$^a$, —CO$_2$R$^a$, —CONR$^a$R$^b$, —CH=NOR$^a$ or a five- or six-membered heteroaromatic ring optionally bearing up to 2 substituents selected from halogen, CN, CF$_3$, C$_{1-6}$alkyl, C$_{1-6}$alkoxy, C$_{1-6}$alkylthio, amino, C$_{1-6}$alkylamino and di(C$_{1-6}$)alkylamino;

or the moiety -E-Z may combine with an adjacent R$^2$ group as defined below;

R$^a$ and R$^b$ independently represent H or a hydrocarbon group of up to 7 carbon atoms which is optionally substituted with up to 3 halogen atoms or with CN, OH, C$_{1-4}$alkoxy, C$_{1-4}$alkylthio, amino, C$_{1-4}$alkylamino or di(C$_{1-4}$)alkylamino; or R$^a$ and R$^b$, when linked through a nitrogen atom, together represent a heterocyclic ring of 4, 5 or 6 members, optionally bearing up to 3 substituents selected from halogen, CN, CF$_3$, oxo, OH, C$_{1-4}$alkyl and C$_{1-4}$alkoxy;

each R$^1$ independently represents halogen, CN, CF$_3$, OCF$_3$, C$_{1-6}$ alkyl, OH, benzylthio, C$_{1-6}$ alkoxy or hydroxymethyl; and each R$^2$ independently represents halogen, CN, CONH$_2$, C$_{1-4}$alkyl or C$_{1-4}$alkoxy; or an R$^2$ group and the moiety -E-Z when attached to adjacent ring positions may complete a fused 5- or 6-membered carbocyclic or heterocyclic ring optionally bearing up to 3 substituents selected from halogen, CN, CF$_3$, oxo, R$^a$ and amino; with the proviso that when A represents the residue of a phenyl ring and W represents —CH=CH—, m is not zero and at least one R$^1$ represents F;

or a pharmaceutically acceptable salt or hydrate thereof.

2. The compound of claim 1 wherein W is selected from: —CH=CH—, —CF=CH—, —CH=CF—, —C(OH)=CH—, and —CH=C(OH)—.

3. The compound of claim 1 wherein (R$^1$)$_m$ and the phenyl ring to which it is attached are a 4-fluorophenyl or 2,4-difluorophenyl group.

4. The compound of claim 1 of the formula II:

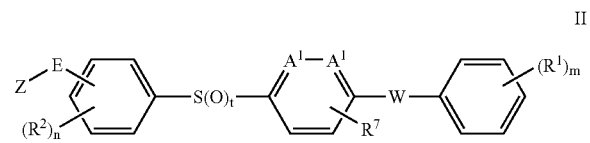

wherein each A$^1$ represents CH;

R$^7$ represents H, halogen, CN, CF$_3$, OR$^a$, CO$^2$R$^a$, CONR$^a$R$^b$, NR$^a$R$^b$ or C$_{1-4}$alkyl which is optionally substituted with halogen, CN, CF$_3$, OR$^a$, CO$_2$R$^a$, CONR$^a$R$^b$ or NR$^a$R$^b$; or pharmaceutically acceptable salt.

5. The compound of claim 1 wherein Z represents SOR$^a$, SO$_2$R$^a$, CONHCOR$^a$, NHCH$_2$CO$_2$R$^a$ or CO$_2$R$^a$ and R$^a$ represents C$_{1-6}$alkyl.

6. The compound of claim 1 of the formula IV:

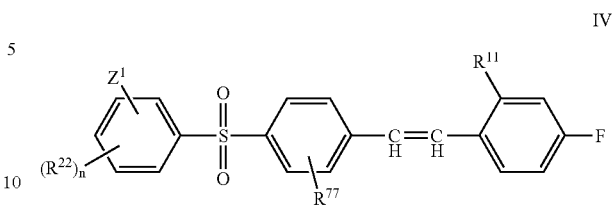

wherein:
n is 0 or 1;
R$^{11}$ represents H or F;
R$^{22}$ represents halogen, CN, CONH$_2$, C$_{1-4}$alkyl or C$_{1-4}$alkoxy;
R$^{77}$ represents H or C$_{1-4}$alkyl; and
Z represents C$_{1-6}$oxycarbonyl, or a 5- or 6-membered heteroaromatic ring which optionally bears a methyl substituent;

or a pharmaceutically acceptable salt.

7. The compound of claim 6 wherein Z$^1$ is ortho to the sulfone moiety in formula IV.

8. The compound of claim 6 wherein R$^{11}$ represents H.

9. The compound of claim 6 wherein Z$^1$ represents C$_{1-6}$alkoxycarbonyl.

10. The compound of claim 6 wherein Z$^1$ represents a 5- or 6-membered heteroaromatic ring which optionally bears a methyl substituent.

11. The compound of which is selected from the group consisting of:
methyl 2-({4-[(E)-2-(2,4-difluorophenyl)vinyl]phenyl}sulfonyl)benzoate;
methyl 2-({4-[(E)-2-(4-fluorophenyl)vinyl]phenyl}sulfonyl)benzoate;
methyl 3-({4-[(E)-2-(4-fluorophenyl)vinyl]phenyl}sulfonyl)benzoate; and
methyl 2-({4-[(E)-2-(4-fluorophenyl)vinyl]phenyl}sulfonyl)-3-methylbenzoate;
or a pharmaceutically acceptable salt.

12. The compound which is methyl 2-({4-[(E)-2-(4-fluorophenyl)vinyl]phenyl}sulfonyl)benzoate, or a pharmaceutically acceptable salt.

13. The compound of claim 12 which is methyl 2-({4-[(E)-2-(4-fluorophenyl)vinyl]phenyl}sulfonyl)benzoate.

14. A pharmaceutical composition which comprises an inert carrier and compound of claim 1 or a pharmaceutically acceptable salt.

15. A pharmaceutical composition which comprises an inert carrier and the compound of claim 11 or a pharmaceutically acceptable salt.

16. A pharmaceutical composition which comprises an inert carrier and the compound of claim 12 or a pharmaceutically acceptable salt.

17. A pharmaceutical composition which comprises an inert carrier and the compound claim 13 or a pharmaceutically acceptable salt.

* * * * *